US012583837B2

(12) United States Patent
Huang et al.

(10) Patent No.: US 12,583,837 B2
(45) Date of Patent: Mar. 24, 2026

(54) SOLID FORMS COMPRISING (S)-2-(2,6-DIOXOPIPERIDIN-3-YL)-4-((2-FLUORO-4-((3-MORPHOLINOAZETIDIN-1-YL)METHYL)BENZYL)AMINO) ISOINDOLINE-1,3-DIONE AND SALTS THEREOF, AND COMPOSITIONS COMPRISING AND METHODS OF USING THE SAME

(71) Applicant: Celgene Corporation, Summit, NJ (US)

(72) Inventors: Lianfeng Huang, Basking Ridge, NJ (US); Wenju Wu, Warren, NJ (US)

(73) Assignee: Celgene Corporation, Summit, NJ (US)

( * ) Notice: Subject to any disclaimer, the term of this patent is extended or adjusted under 35 U.S.C. 154(b) by 502 days.

(21) Appl. No.: 18/100,412

(22) Filed: Jan. 23, 2023

(65) Prior Publication Data

US 2023/0339901 A1 Oct. 26, 2023

Related U.S. Application Data

(63) Continuation of application No. 17/075,359, filed on Oct. 20, 2020, now Pat. No. 11,578,056.

(60) Provisional application No. 62/923,972, filed on Oct. 21, 2019.

(51) Int. Cl.

| | |
|---|---|
| ***A61K 31/5377*** | (2006.01) |
| ***A61P 35/00*** | (2006.01) |
| ***A61P 35/02*** | (2006.01) |
| ***C07D 401/14*** | (2006.01) |

(52) U.S. Cl.
CPC ............ *C07D 401/14* (2013.01); *A61P 35/00* (2018.01); *A61P 35/02* (2018.01); *C07B 2200/13* (2013.01)

(58) Field of Classification Search
None
See application file for complete search history.

(56) References Cited

U.S. PATENT DOCUMENTS

| | | | | |
|---|---|---|---|---|
| 2016/0045484 A1 | 2/2016 | Tun | | |
| 2017/0313676 A1 | 11/2017 | Ge et al. | | |
| 2019/0322647 A1* | 10/2019 | Alexander | ........... | C07D 403/14 |
| 2020/0039950 A1 | 2/2020 | Lee et al. | | |
| 2021/0113575 A1* | 4/2021 | Bhat | .................... | A61K 9/4858 |

FOREIGN PATENT DOCUMENTS

| | | | |
|---|---|---|---|
| EP | 3524598 A1 | 8/2019 |
| WO | WO 2002/059106 A1 | 8/2002 |
| WO | WO 2008/033567 A1 | 3/2008 |
| WO | WO 2011/100380 A1 | 8/2011 |
| WO | WO 2011/162515 A2 | 12/2011 |
| WO | WO 2017/176958 A1 | 10/2017 |
| WO | WO 2019/209692 A1 | 10/2019 |
| WO | WO 2020/210418 A1 | 10/2020 |
| WO | WO 2021/080935 A1 | 4/2021 |
| WO | WO 2021/080936 A1 | 4/2021 |
| WO | WO 2021/080937 A1 | 4/2021 |

OTHER PUBLICATIONS

Stieger (Stieger et al., Recrystallization of Active Pharmaceutical Ingredients, Crystallization Science and Technology, 2012 (Year: 2012).*

Rodriguez-Abreu et al., Epidemiology of hematological malignancies, Annals of Oncology 18 (Supplement 1): i3-i8, 2007 (Year: 2007).*

Berge et al., "Pharmaceutical salts", Journal of Pharmaceutical Sciences, 66(1), 1-19 (1977).

Helin-Tanninen and Pinto, "Oral solids", *Practical Pharmaceutics*, Springer, Cham, 2015, 51-52.

Hallek et al. "iwCLL guidelines for diagnosis, indications for treatment, response assessment, and supportive management of CLL", *Blood*, 131(25), 2745-2760 (2018)).

* cited by examiner

*Primary Examiner* — Kortney L. Klinkel
*Assistant Examiner* — Alison Azar Salamatian
(74) *Attorney, Agent, or Firm* — Jones Day

(57) ABSTRACT

Provided herein are formulations, processes, solid forms and methods of use (e.g., methods of treating a hematological malignancy) relating to salts of and solid forms comprising free base or salts of (S)-2-(2,6-dioxopiperidin-3-yl)-4-((2-fluoro-4-((3-morpholinoazetidin-1-yl)methyl)benzyl) amino)isoindoline-1,3-dione.

14 Claims, 12 Drawing Sheets

Figure 1:
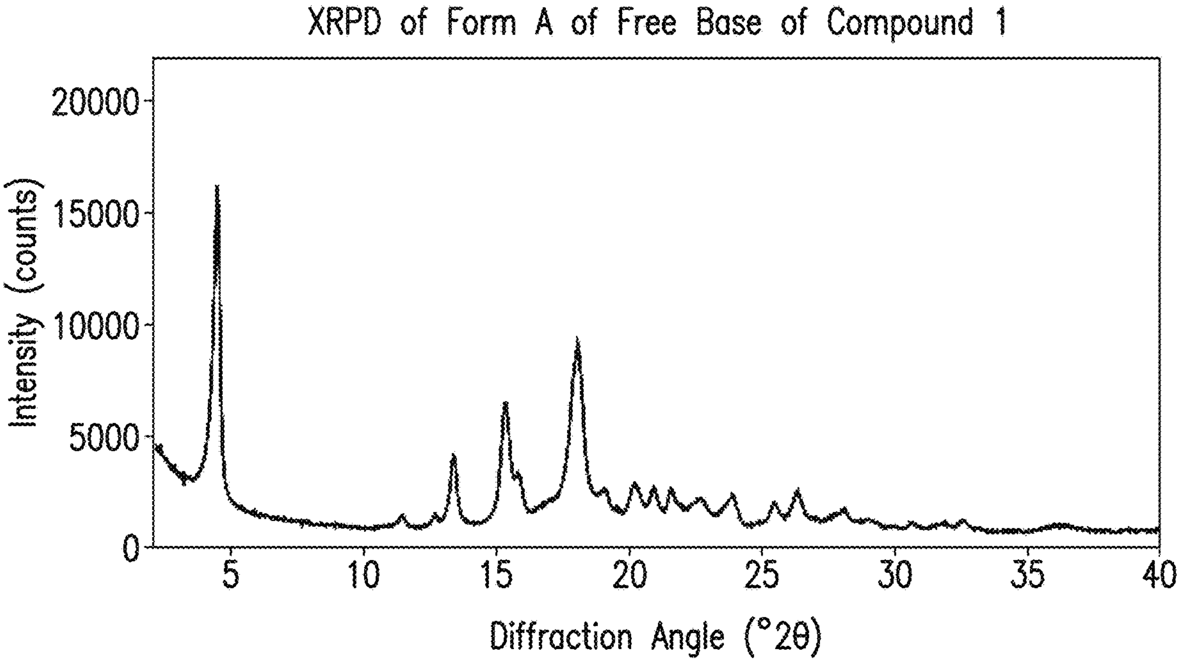

SEM of Form A of a Hydrochloride Salt of Compound 1

Overlay Plot of Forms A, B, C, and D of a Tosylate Salt of Compound 1

SOLID FORMS COMPRISING (S)-2-(2,6-DIOXOPIPERIDIN-3-YL)-4-((2-FLUORO-4-((3-MORPHOLINOAZETIDIN-1-YL)METHYL)BENZYL)AMINO)ISOINDOLINE-1,3-DIONE AND SALTS THEREOF, AND COMPOSITIONS COMPRISING AND METHODS OF USING THE SAME

This application is a continuation application of U.S. application Ser. No. 17/075,359, filed Oct. 20, 2020, which claims priority to U.S. Provisional Application No. 62/923,972, filed on Oct. 21, 2019, the entireties of which are incorporated herein by reference.

1. FIELD

Provided herein are salts of and solid forms comprising free base or salts of (S)-2-(2,6-dioxopiperidin-3-yl)-4-((2-fluoro-4-((3-morpholinoazetidin-1-yl)methyl)benzyl) amino)isoindoline-1,3-dione. Pharmaceutical compositions comprising such salts and solid forms and methods of use of such salts and solid forms for treating, preventing, and managing various disorders are also provided herein.

2. BACKGROUND

Alternative solid forms of pharmaceutical compounds have emerged as a possible approach to modulate or enhance the physical and chemical properties of drug products. The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solid forms include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The type of salt form of a particular active pharmaceutical ingredient may affect certain properties of the active pharmaceutical ingredient. These properties include solubility, stability, and bioavailability.

The variety of possible solid forms, including both free base forms and salt forms, creates potential diversity in physical and chemical properties for a given pharmaceutical compound. The discovery and selection of solid forms are of great importance in the development of an effective, stable and marketable pharmaceutical product.

3. SUMMARY

Provided herein are solid forms (e.g., crystalline forms, amorphous forms, polymorphs or mixtures thereof) comprising Compound 1:

1

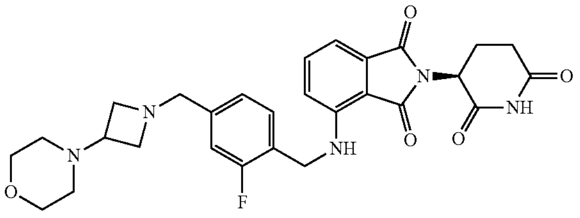

having the chemical name (S)-2-(2,6-dioxopiperidin-3-yl)-4-((2-fluoro-4-((3-morpholinoazetidin-1-yl) methyl)benzyl)amino)isoindoline-1,3-dione. Also provided herein are methods of preparing, isolating, and characterizing the solid forms.

In one embodiment, the solid form comprises a free base of Compound 1. In one embodiment, the solid form is Form A or Form B of a free base of Compound 1, as provided herein.

In one embodiment, the solid form comprises a salt of Compound 1.

In one embodiment, the solid form comprises a hydrochloride salt of Compound 1. In one embodiment, the solid form is Form A or Form B of a hydrochloride salt of Compound 1, as provided herein.

In one embodiment, the solid form comprises a fumarate salt of Compound 1. In one embodiment, the solid form is Form A of a fumarate salt of Compound 1, as provided herein.

In one embodiment, the solid form comprises a tosylate salt of Compound 1. In one embodiment, the solid form is Form A of a tosylate salt of Compound 1, as provided herein.

In one embodiment, the solid form comprises a maleate salt of Compound 1. In one embodiment, the solid form is Form A of a maleate salt of Compound 1, as provided herein.

In one embodiment, the solid form comprises a besylate salt of Compound 1. In one embodiment, the solid form is Form A of a besylate salt of Compound 1, as provided herein.

Also provided herein are salts of Compound 1. In one embodiment, the salt is a hydrochloride salt, a fumarate salt, a tosylate salt, a maleate salt, or a besylate salt. In one embodiment, the salt is crystalline. In one embodiment, the salt is amorphous.

The solid forms provided herein are useful as active pharmaceutical ingredients for the preparation of formulations for use in animals or humans. Thus, embodiments herein encompass the use of these solid forms as a final drug substance. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising Compound 1 and a pharmaceutically acceptable diluent, excipient or carrier.

Also provided are pharmaceutical compositions formulated for administration by an appropriate route and means containing effective concentrations of a solid form comprising Compound 1 provided herein, and optionally comprising at least one pharmaceutical carrier.

Also provided herein are methods of using a solid form comprising Compound 1 provided herein for treating, preventing or managing a hematological malignancy. In one embodiment, the method is for treating a hematological malignancy. In one embodiment, the method is for preventing a hematological malignancy. In one embodiment, the method is for managing a hematological malignancy.

In one embodiment, the hematological malignancy is acute myeloid leukemia (AML), acute lymphocytic leukemia (ALL), multiple myeloma (MM), non-Hodgkin's lymphoma (NHL), diffuse large B-cell lymphoma (DLBCL), Hodgkin's lymphoma (HL), T-cell lymphoma (TCL), Burkitt lymphoma (BL), chronic lymphocytic leukemia/small lymphocytic lymphoma (CLL/SLL), marginal zone lymphoma (MZL), or myelodysplastic syndromes (MDS).

Also provided herein are methods of using a solid form comprising Compound 1 provided herein, alone or in combination with rituximab, for treating, preventing or managing non-Hodgkin lymphoma (NHL). In one embodiment, the method is for treating NHL. In one embodiment, the method is for preventing NHL. In one embodiment, the method is for managing NHL.

In certain embodiments, the NHL is diffuse large B-cell lymphoma (DLBCL), follicular lymphoma (FL), mantle cell lymphoma (MCL), or primary central nervous system lymphoma (PCNSL).

Also provided herein are methods of using a solid form comprising Compound 1 provided herein, alone or in combination with obinutuzumab, for treating, preventing or managing chronic lymphocytic leukemia (CLL). In one embodiment, the method is for treating CLL. In one embodiment, the method is for preventing CLL. In one embodiment, the method is for managing CLL.

Also provided herein are methods of using a solid form comprising Compound 1 provided herein, alone or in combination with obinutuzumab, for treating, preventing or managing small lymphocytic lymphoma (SLL). In one embodiment, the method is for treating SLL. In one embodiment, the method is for preventing SLL. In one embodiment, the method is for managing SLL.

Also provided herein is a solid form or salt of Compound 1 for use in a method of treating a disease provided herein, wherein the method comprises administering to a patient a therapeutically effective amount of the solid form or salt of Compound 1. Also provided herein is a pharmaceutical composition comprising the solid form or salt of Compound 1 for use in a method of treating a disease provided herein.

These and other aspects of the subject matter described herein will become evident upon reference to the following detailed description.

4. BRIEF DESCRIPTION OF THE DRAWINGS

FIG. 1 provides a representative X-ray powder diffraction (XRPD) pattern of Form A of a free base of Compound 1.

Figure 2:
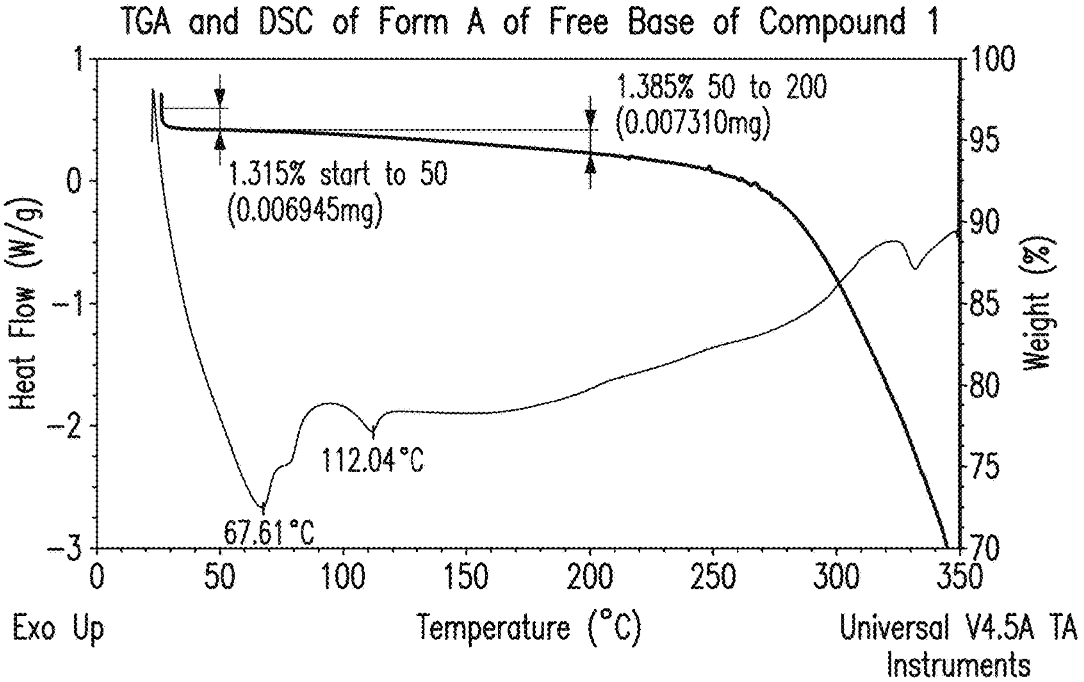

FIG. 2 provides representative thermal gravimetric analysis (TGA) and differential scanning calorimetry (DSC) thermograms of Form A of a free base of Compound 1.

Figure 3:
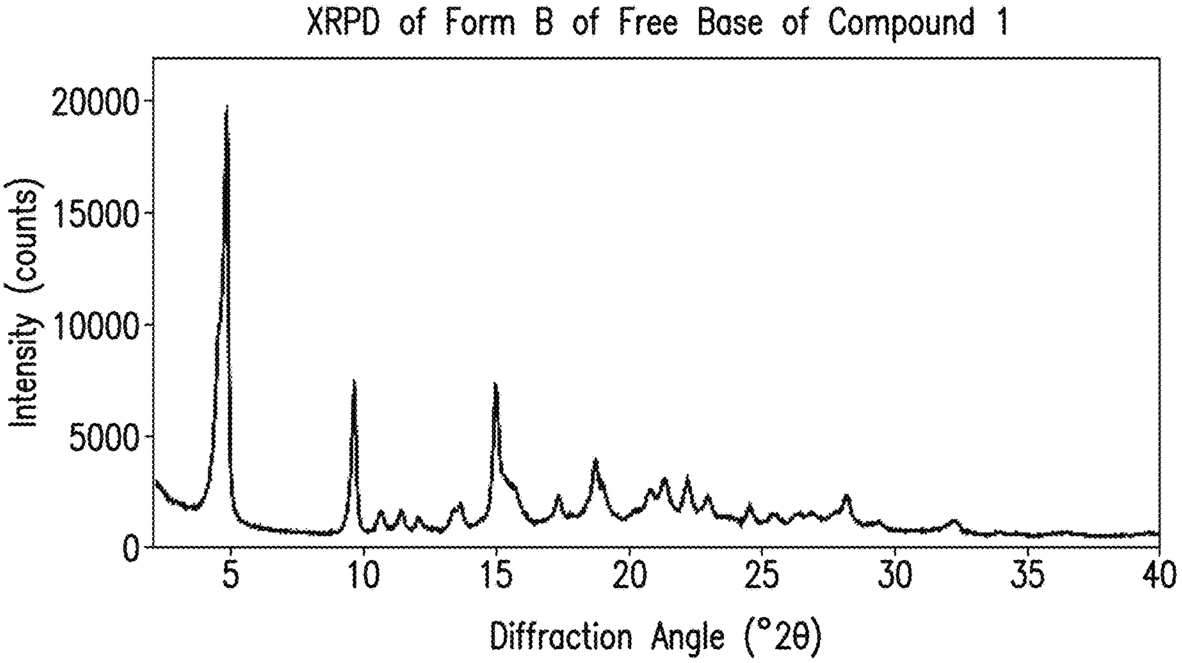

FIG. 3 provides a representative XRPD pattern of Form B of a free base of Compound 1.

Figure 4:
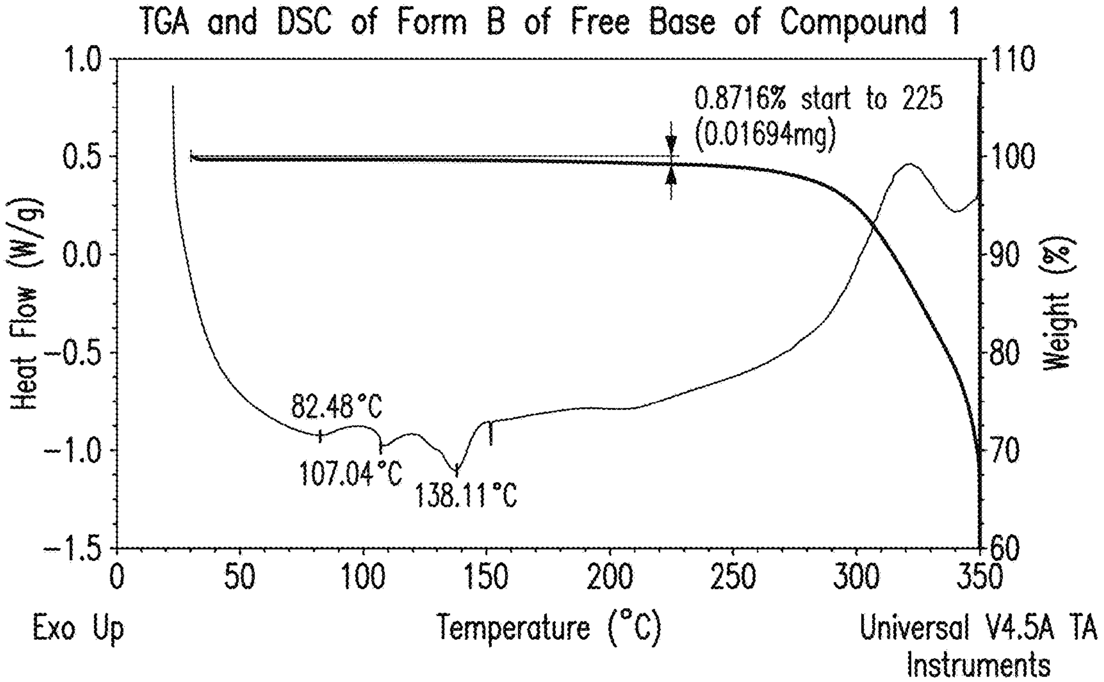

FIG. 4 provides representative TGA and DSC thermograms of Form B of a free base of Compound 1.

Figure 5:
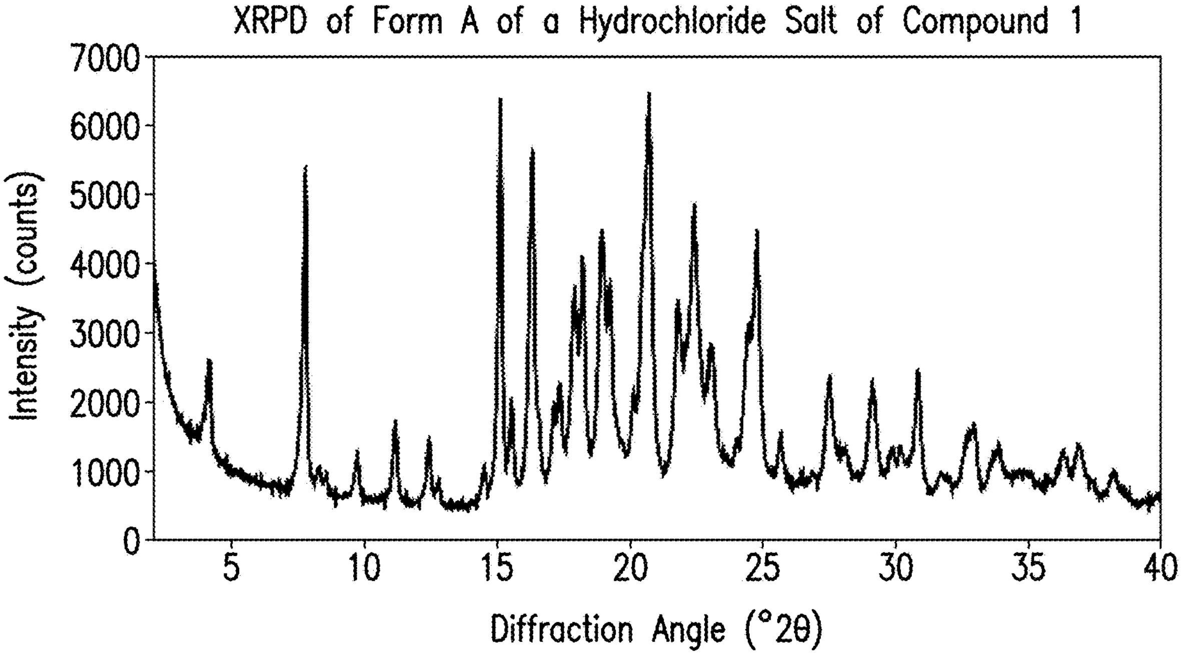

FIG. 5 provides a representative XRPD pattern of Form A of a hydrochloride salt of Compound 1.

Figure 6:
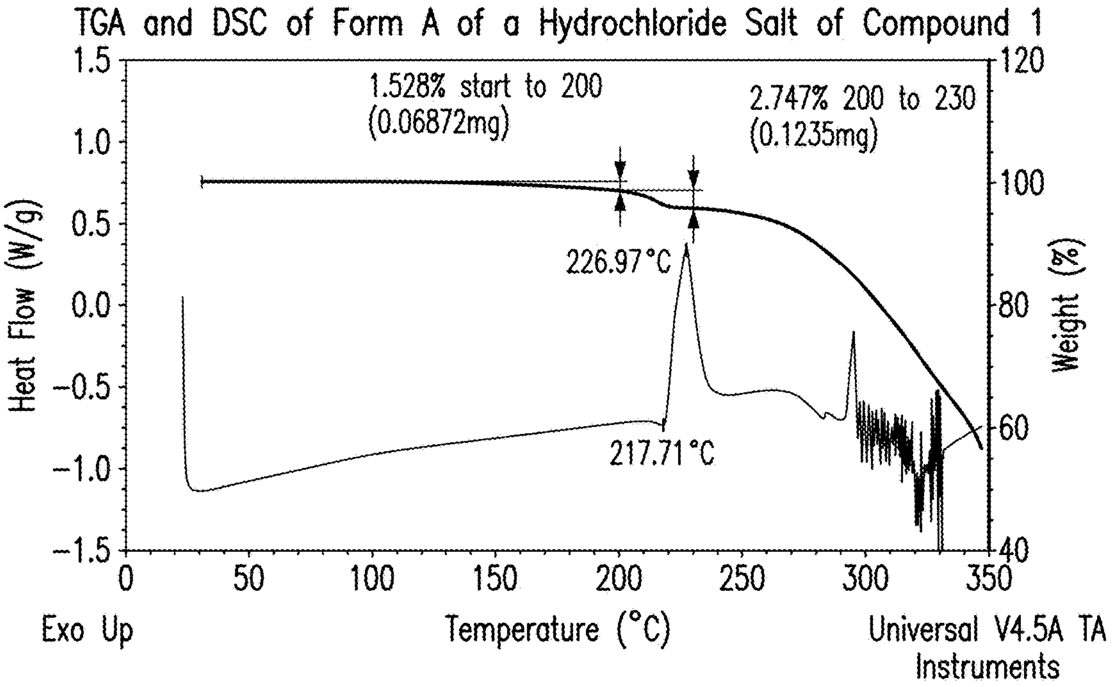

FIG. 6 provides representative TGA and DSC thermograms of Form A of a hydrochloride salt of Compound 1.

Figure 7:
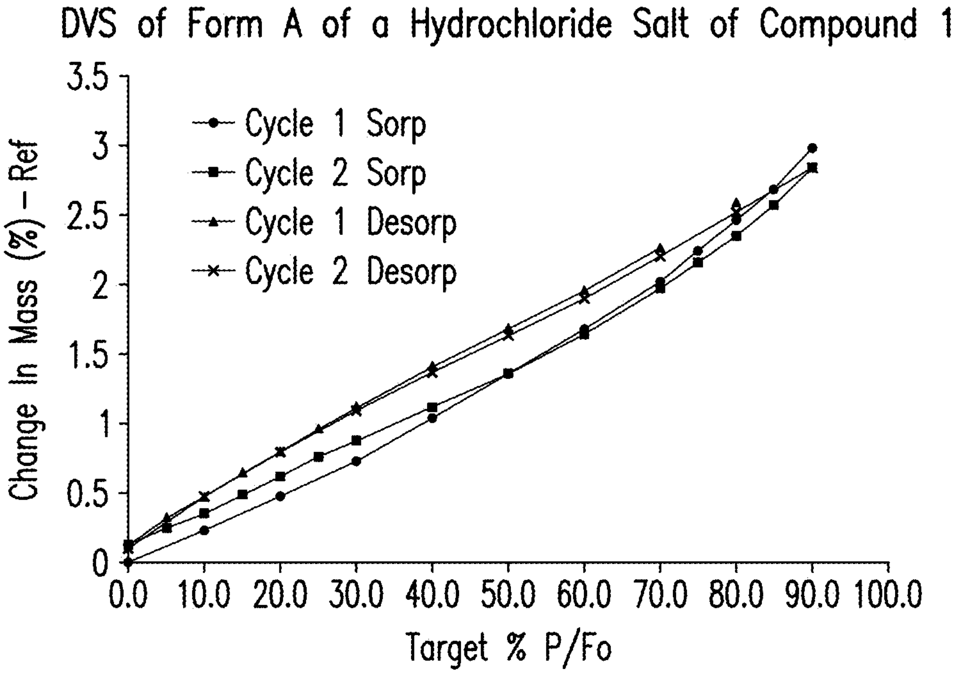

FIG. 7 provides a representative dynamic vapor sorption (DVS) isotherm plot of Form A of a hydrochloride salt of Compound 1.

Figure 8:
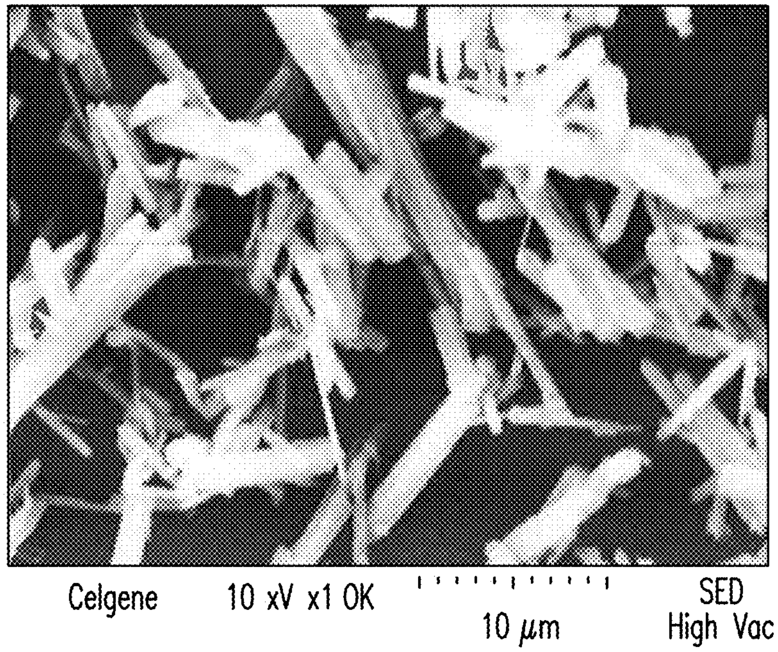

FIG. 8 provides a representative SEM image of Form A of a hydrochloride salt of Compound 1.

Figure 9:
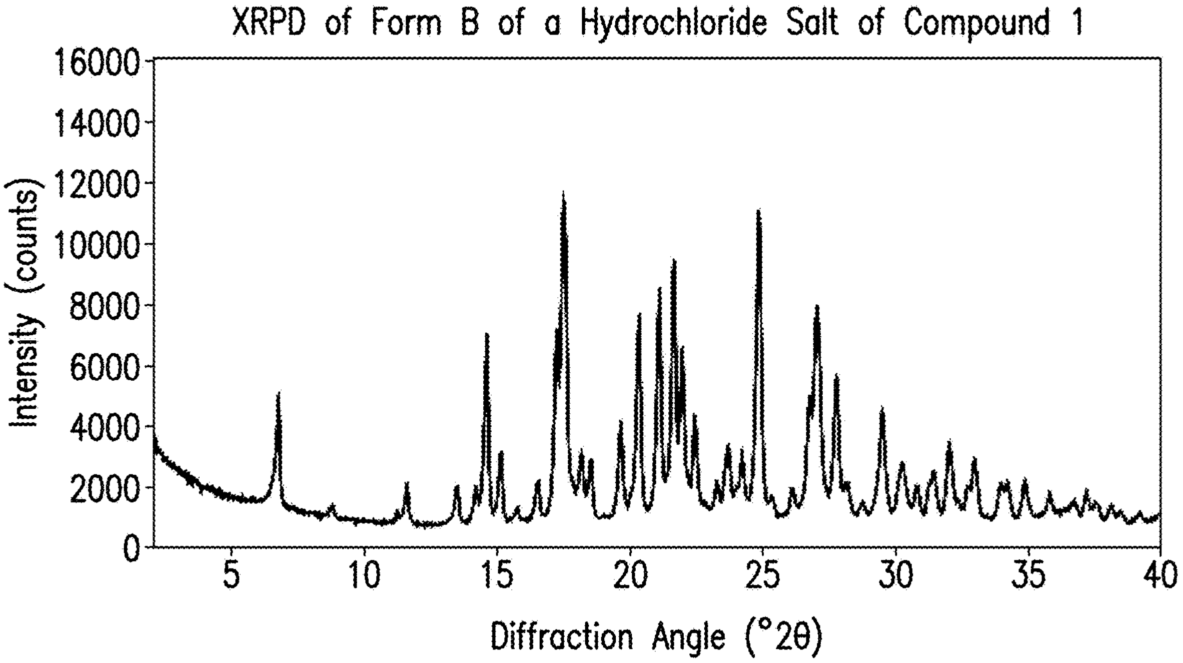

FIG. 9 provides a representative XRPD pattern of Form B of a hydrochloride salt of Compound 1.

Figure 10:
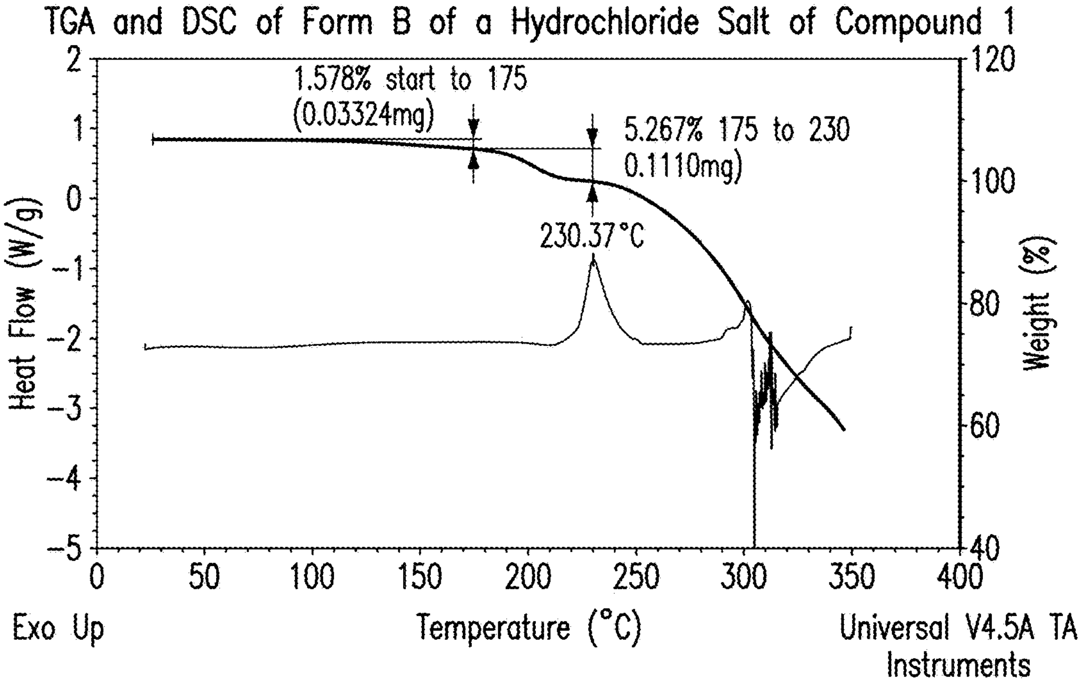

FIG. 10 provides representative TGA and DSC thermograms of Form B of a hydrochloride salt of Compound 1.

Figure 11:
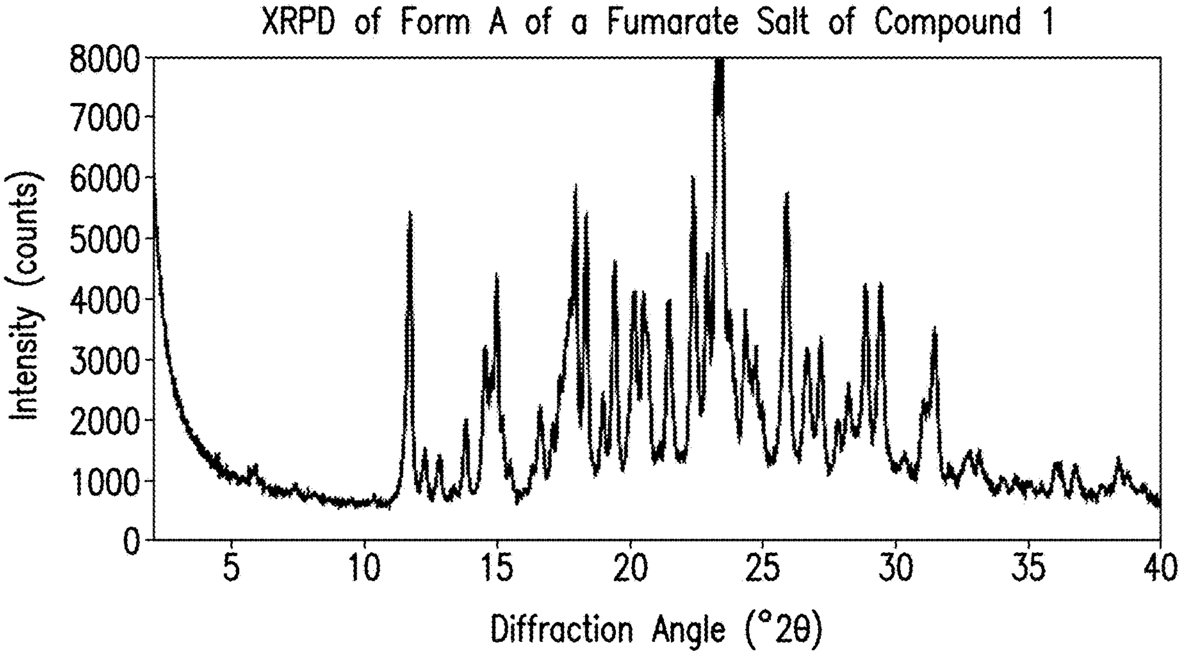

FIG. 11 provides a representative XRPD pattern of Form A of a fumarate salt of Compound 1.

Figure 12:
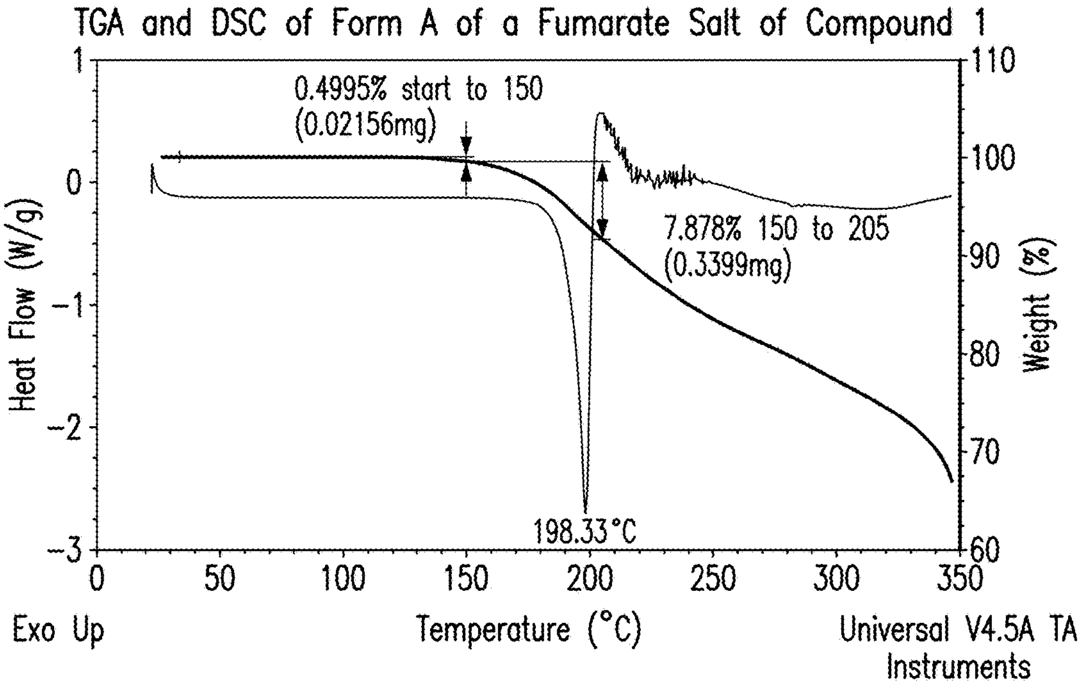

FIG. 12 provides representative TGA and DSC thermograms of Form A of a fumarate salt of Compound 1.

Figure 13:
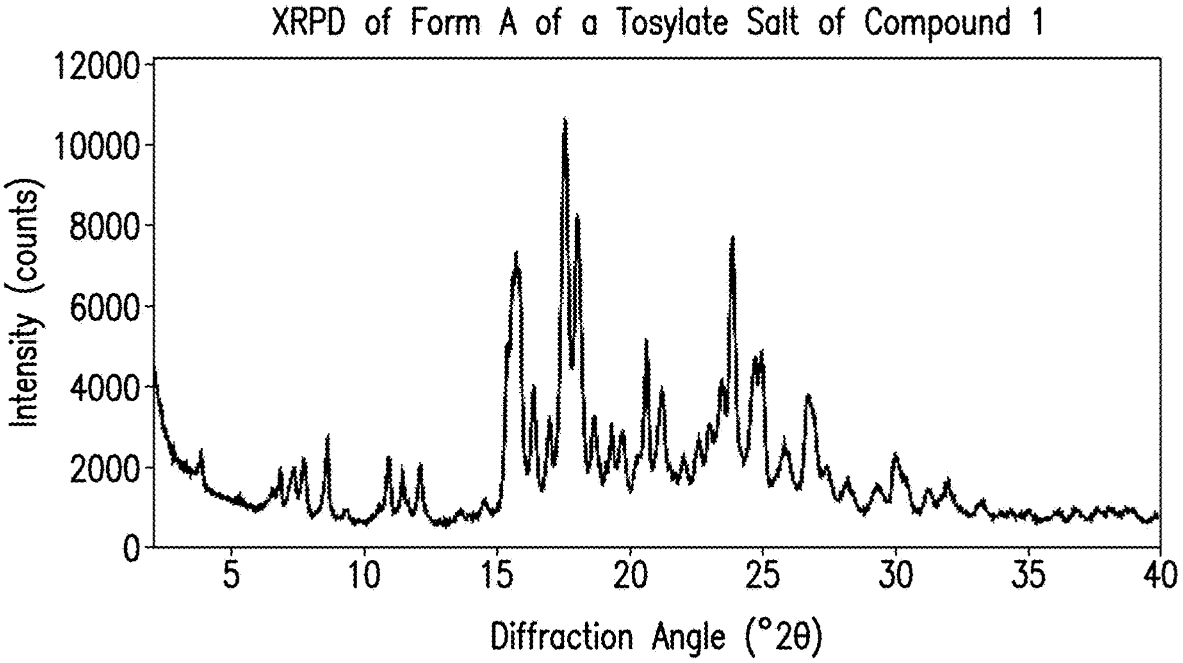

FIG. 13 provides a representative XRPD pattern of Form A of a tosylate salt of Compound 1.

Figure 14:
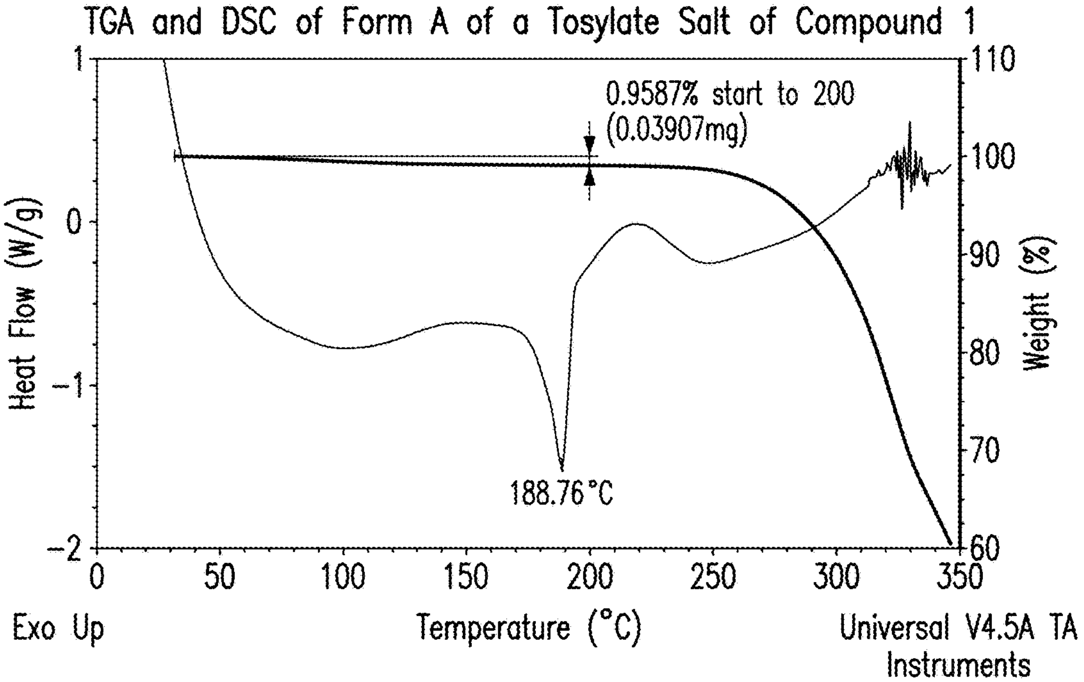

FIG. 14 provides representative TGA and DSC thermograms of Form A of a tosylate salt of Compound 1.

Figure 15:
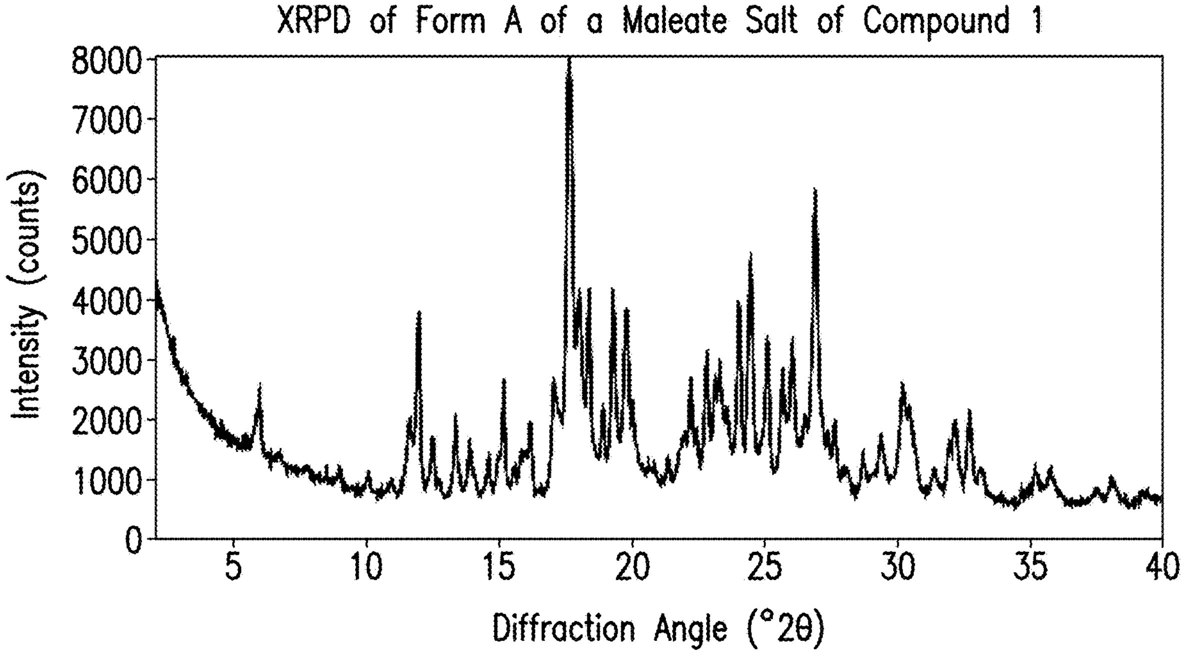

FIG. 15 provides a representative XRPD pattern of Form A of a maleate salt of Compound 1.

Figure 16:
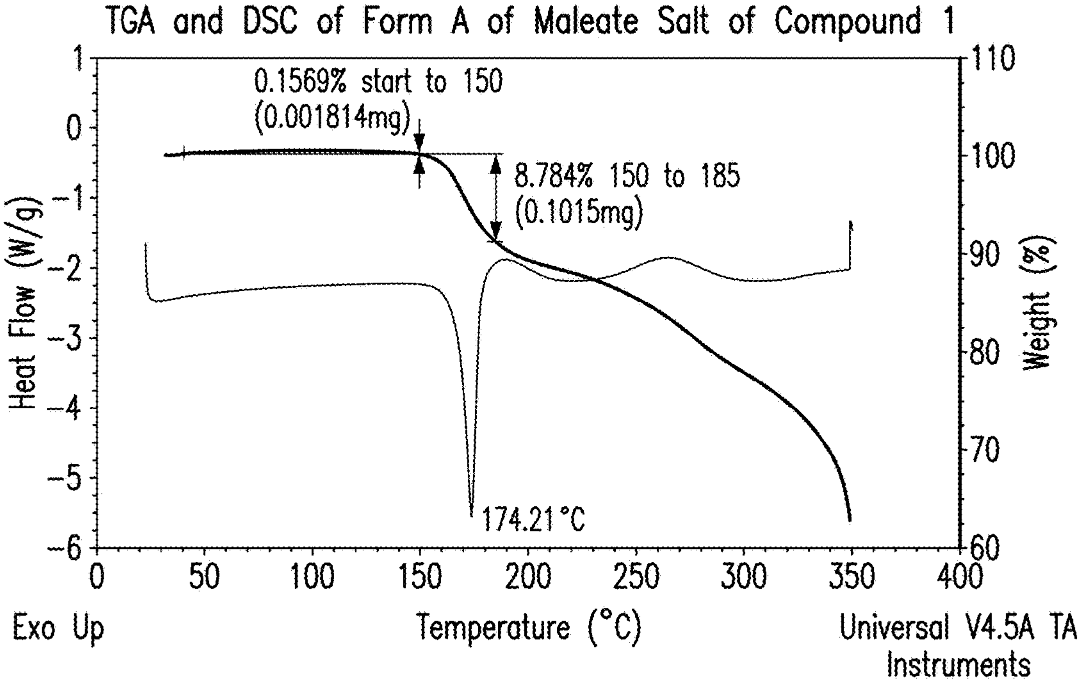

FIG. 16 provides representative TGA and DSC thermograms of Form A of a maleate salt of Compound 1.

Figure 17:
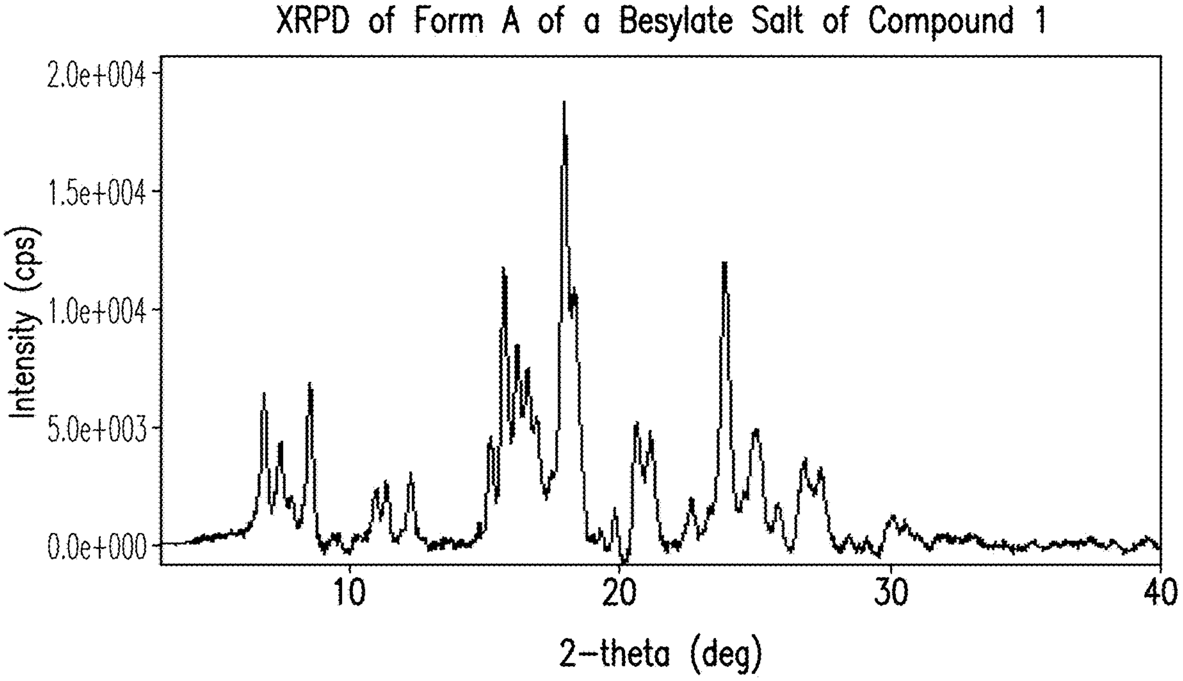

FIG. 17 provides a representative XRPD pattern of Form A of a besylate salt of Compound 1.

Figure 18:
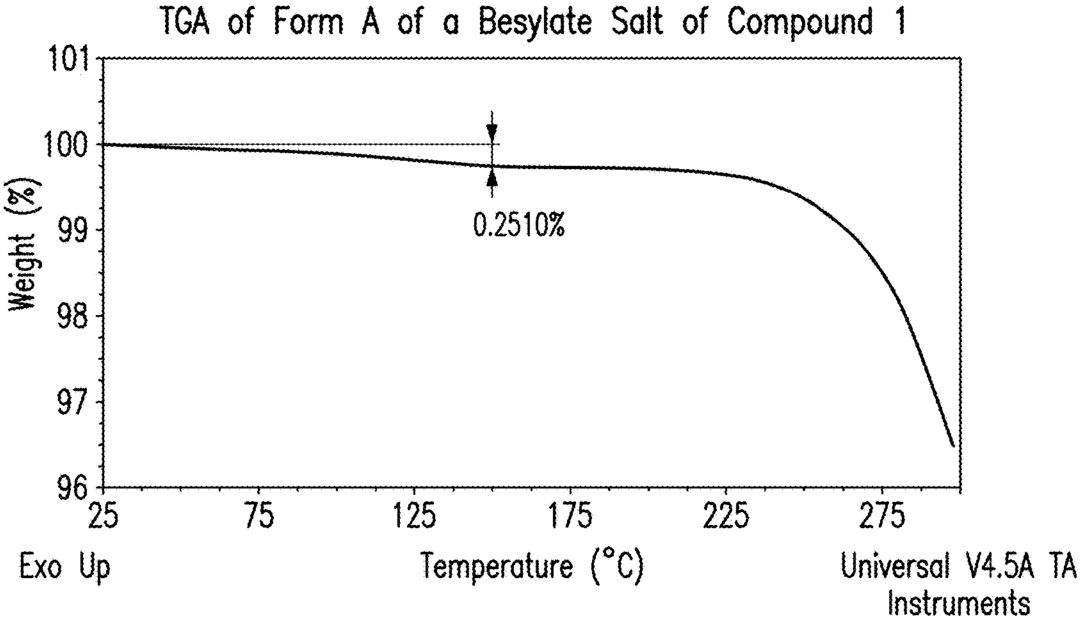

FIG. 18 provides a representative TGA thermogram of Form A of a besylate salt of Compound 1.

Figure 19:
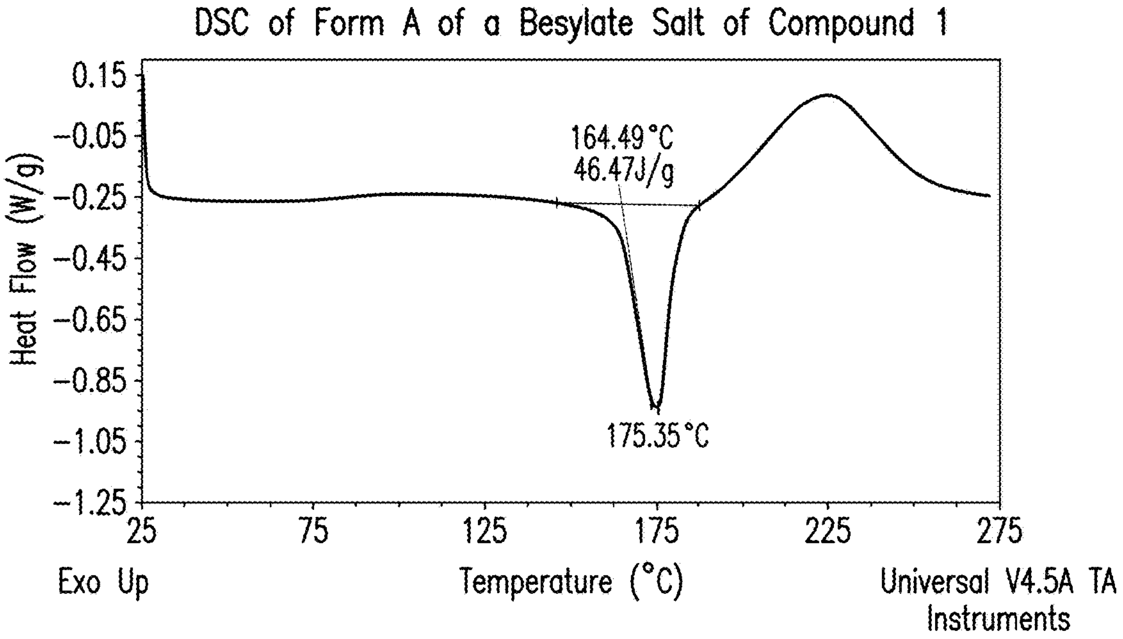

FIG. 19 provides a representative DCS thermogram of Form A of a besylate salt of Compound 1.

Figure 20:
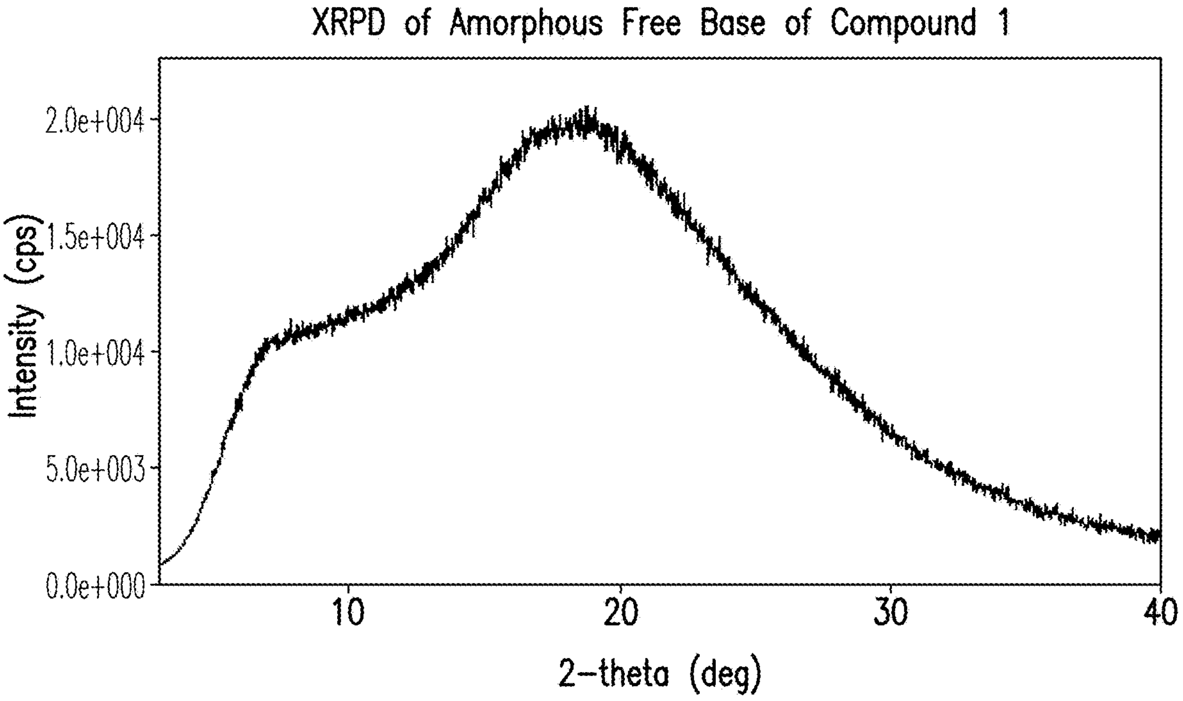

FIG. 20 provides a representative XRPD pattern of amorphous starting material of free base of Compound 1.

Figure 21:
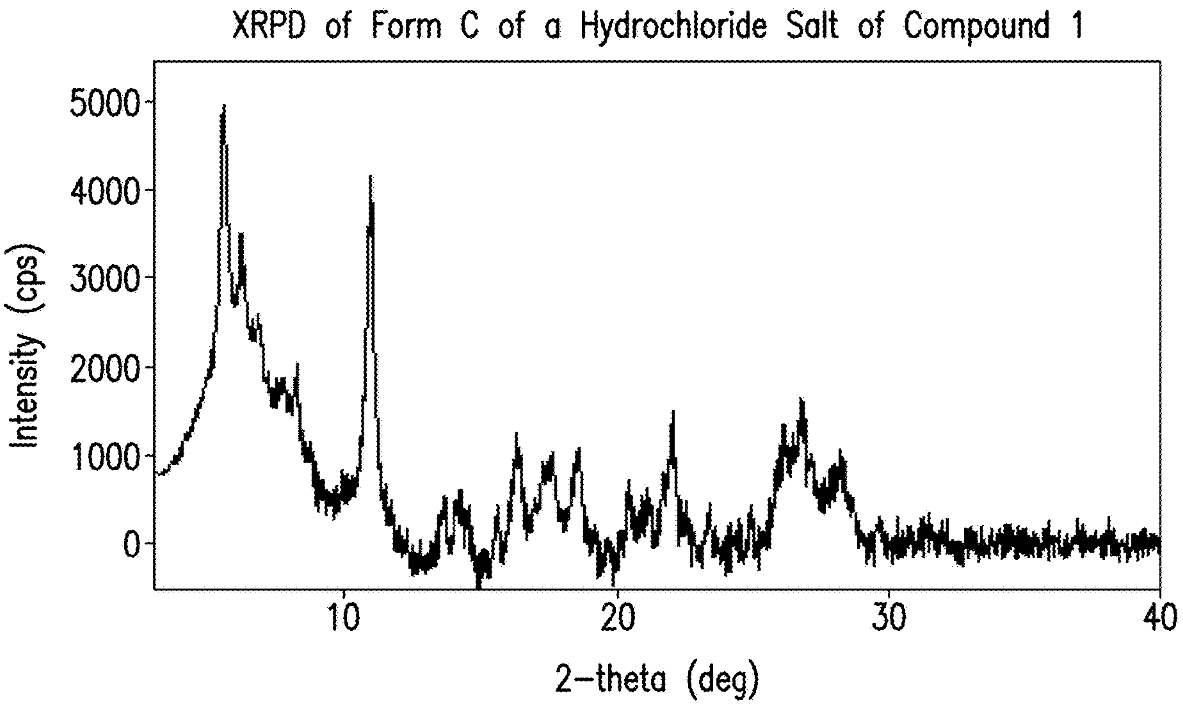

FIG. 21 provides a representative XRPD pattern of Form C of a hydrochloride salt of Compound 1.

Figure 22:
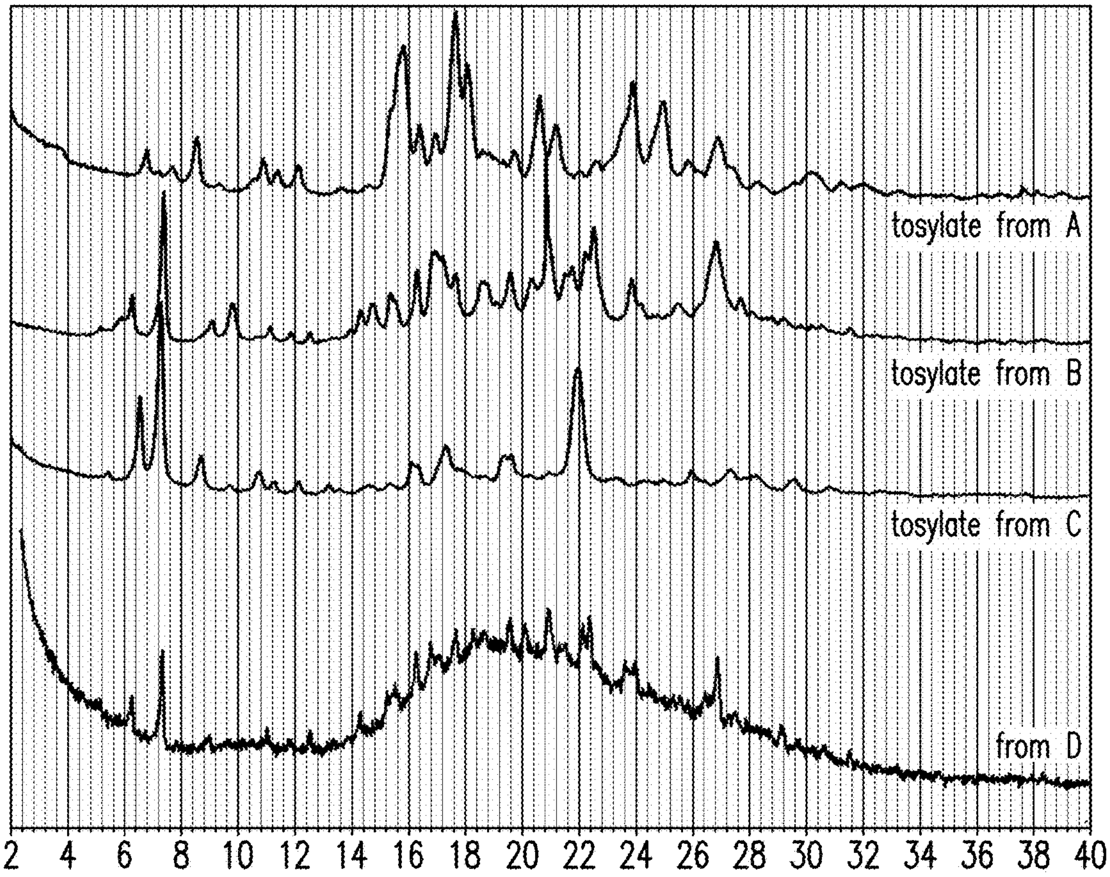

FIG. 22 provides an overlay plot of Forms A, B, C, and D of a tosylate salt of Compound 1.

5. DETAILED DESCRIPTION

5.1 Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms “comprising” and “including” are intended to include examples encompassed by the term “consisting of”. Consequently, the term “consisting of” can be used in place of the terms “comprising” and “including” to provide for more specific embodiments of the invention.

The term “consisting of” means that a subject-matter has at least 90%, 95%, 97%, 98% or 99% of the stated features or components of which it consists. In another embodiment the term “consisting of” excludes from the scope of any succeeding recitation any other features or components, excepting those that are not essential to the technical effect to be achieved.

As used herein, the term “or” is to be interpreted as an inclusive “or” meaning any one or any combination. Therefore, “A, B or C” means any of the following: “A; B; C; A and B; A and C; B and C; A, B and C”. An exception to this definition will occur only when a combination of elements, functions, steps or acts are in some way inherently mutually exclusive.

As used herein, and unless otherwise specified, the terms “about” and “approximately,” when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms “about” and “approximately,” when used in this context, contemplate a dose, amount, or weight percent within 30%, within 20%, within 15%, within 10%, or within 5%, of the specified dose, amount, or weight percent.

As used herein and unless otherwise specified, the terms “about” and “approximately,” when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms “about” and “approximately,” when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of XRPD peak position may vary by up to ±0.2 degrees 2θ while still describing the particular XRPD peak. As used herein, a tilde (i.e., “~”) preceding a numerical value or range of values indicates “about” or “approximately.”

Unless otherwise specified, the terms “X-ray powder diffraction”, “powder X-ray diffraction”, “PXRD”, and “XRPD” are used interchangeably in this application.

As used herein and unless otherwise specified, the terms “solid form” and related terms refer to a physical form which is not predominantly in a liquid or a gaseous state. As used herein, the terms “solid form” and “solid forms” encompass semi-solids. Solid forms may be crystalline, amorphous, partially crystalline, partially amorphous, or mixtures of forms.

The solid forms provided herein may have varying degrees of crystallinity or lattice order. The solid forms provided herein are not limited by any particular degree of crystallinity or lattice order, and may be 0-100% crystalline. Methods of determining the degree of crystallinity are known to those of ordinary skill in the, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms provided herein are about 0, 5, 10, 15, 20, 25, 30, 35, 40, 45, 50, 55, 60, 65, 70, 75, 80, 85, 90, 95 or 100% crystalline.

As used herein and unless otherwise specified, the term “crystalline” and related terms used herein, when used to describe a substance, component, product, or form, mean that the substance, component, product, or form is substantially crystalline, for example, as determined by X-ray diffraction. See, e.g., *Remington: The Science and Practice of Pharmacy,* 21$^{st}$ edition, Lippincott, Williams and Wilkins, Baltimore, M D (2005); *The United States Pharmacopeia,* 23$^{rd}$ edition, 1843-1844 (1995).

As used herein and unless otherwise specified, the term “crystal form,” “crystal forms,” and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, co-crystals of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous form(s) and/or other crystal form(s) on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

A “single-component” solid form comprising a compound consists essentially of the compound. A “multiple-component” solid form comprising a compound comprises a significant quantity of one or more additional species, such as ions and/or molecules, within the solid form. For example, in certain embodiments, a crystalline multiple-component solid form comprising a compound further comprises one or more species non-covalently bonded at regular positions in the crystal lattice. For another example, in certain embodiments, an amorphous multiple-component solid form comprising a compound further comprises one or more polymer(s), and the compound is dispersed in a solid matrix that comprises the polymer(s).

Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

Unless otherwise specified, the terms "polymorph," "polymorphic form," "polymorphs," "polymorphic forms," and related terms herein refer to two or more crystal forms that consist essentially of the same molecule, molecules or ions. Like different crystal forms, different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing (for example, one polymorph might be more likely to form solvates or might be difficult to filter and wash free of impurities, and particle shape and size distribution might be different between polymorphs).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. In certain embodiments, an amorphous form of a substance may comprise additional components or ingredients (for example, an additive, a polymer, or an excipient that may serve to further stabilize the amorphous form). In certain embodiments, amorphous form may be a solid solution.

Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

Unless otherwise specified, the terms "solvate" and "solvated," as used herein, refer to a solid form of a substance which contains solvent. The terms "hydrate" and "hydrated" refer to a solvate wherein the solvent comprises water. "Polymorphs of solvates" refer to the existence of more than one solid form for a particular solvate composition. Similarly, "polymorphs of hydrates" refers to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, co-crystal, or molecular complex. The terms "hydrate" and "hydrated," as used herein, can also refer to a hydrate of a salt, co-crystal, or molecular complex.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder. In one embodiment, an XRPD pattern is obtained using Cu Kα radiation. In one embodiment, the ramp rate (heating rate) for a DSC is about 10° C. per minute. In one embodiment, slow heating rate such as 0.5-2.0° C. per minute can be used for more accurate DSC testing. The sample pans used in a DSC testing include, e.g., aluminum, platinum, and stainless steel pans. The pans can have different configurations, e.g., open, pinhole, or hermetically-sealed pans. In one embodiment, the ramp rate for a TGA is about 10° C. per minute.

In certain embodiments, the solid forms, e.g., crystal or amorphous forms, provided herein are substantially pure, i.e., substantially free of other solid forms and/or of other chemical compounds, containing less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

Solid forms may exhibit distinct physical characterization data that are unique to a particular solid form, such as the crystal forms provided herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms provided herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis variation.

As used herein, and unless otherwise specified, the term "pharmaceutically acceptable salts" refers to salts prepared from pharmaceutically acceptable, relatively non-toxic acids, including inorganic acids and organic acids. In certain embodiments, suitable acids include, but are not limited to, acetic, adipic, 4-aminosalicylic, ascorbic, aspartic, benzenesulfonic, benzoic, camphoric, camphorsulfonic, capric, caproic, caprylic, cinnamic, carbonic, citric, cyclamic, dihydrogenphosphoric, 2,5-dihydroxybenzoic (gentisic), 1,2-ethanedisulfonic, ethanesulfonic, fumaric, galactunoric, gluconic, glucuronic, glutamic, glutaric, glycolic, hippuric, hydrobromic, hydrochloric, hydriodic, isobutyric, isethionic, lactic, maleic, malic, malonic, mandelic, methanesulfonic, monohydrogencarbonic, monohydrogen-phosphoric, monohydrogensulfuric, mucic, 1,5-naphthalenedisulfonic, nicotinic, nitric, oxalic, pamoic, pantothenic, phosphoric, phthalic, propionic, pyroglutamic, salicylic, suberic, succinic, sulfuric, tartaric, toluenesulfonic acid, and the like (see, e.g., S. M. Berge et al., *J. Pharm. Sci.,* 66:1-19 (1977); and *Handbook of Pharmaceutical Salts: Properties, Selection and Use*, P. H. Stahl and C. G. Wermuth, Eds., (2002), Wiley, Weinheim). In certain embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridinesulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent. As solids, salts can exist in crystalline or amorphous forms, or mixtures thereof. Salts can also exist in polymorphic forms.

It should be noted that if there is a discrepancy between a depicted structure and a name for that structure, the depicted structure is to be accorded more weight.

As used herein and unless otherwise indicated, the term "treating" means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

As used herein and unless otherwise indicated, the term "preventing" means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein and unless otherwise indicated, the term "effective amount" in connection with a compound means an amount capable of treating, preventing, or managing a disorder, disease or condition, or symptoms thereof.

As used herein and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human.

As used herein and unless otherwise indicated, the term "relapsed" refers to a disorder, disease, or condition that responded to treatment (e.g., achieved a complete response) then had progression. The treatment can include one or more lines of therapy. In one embodiment, the disorder, disease or condition has been previously treated with one or more lines of therapy. In another embodiment, the disorder, disease or condition has been previously treated with one, two, three or four lines of therapy. In some embodiments, the disorder, disease or condition is a hematological malignancy.

In one embodiment, "relapsed" DLBCL may refer to DLBCL that has been previously treated with one or more lines of therapy. In one embodiment, the relapsed DLBCL is DLBCL that has been previously treated with one, two, three or four lines of therapy. In one embodiment, the relapsed DLBCL is DLBCL that has been previously treated with two or more lines of treatment.

In one embodiment, "relapsed" FL may refer to FL that has been previously treated with one or more lines of therapy. In one embodiment, the relapsed FL is FL that has been previously treated with one, two, three or four lines of therapy. In one embodiment, the relapsed FL is FL that has been previously treated with two or more lines of treatment.

As used herein and unless otherwise indicated, the term "refractory" refers to a disorder, disease, or condition that has not responded to prior treatment that can include one or more lines of therapy. In one embodiment, the disorder, disease, or condition has been previously treated one, two, three or four lines of therapy. In one embodiment, the disorder, disease, or condition has been previously treated with two or more lines of treatment, and has less than a complete response (CR) to most recent systemic therapy containing regimen. In some embodiments, the disorder, disease or condition is a hematological malignancy.

In one embodiment, "relapsed or refractory" CLL/SLL may refer to CLL/SLL that has been previously treated with one or more lines of therapy. In one embodiment, the relapsed or refractory CLL/SLL is CLL/SLL that has been previously treated with one, two, three or four lines of therapy. In one embodiment, the relapsed or refractory CLL/SLL is CLL/SLL that has been previously treated with two or more lines of therapy. In one embodiment, the relapsed or refractory CLL/SLL is CLL/SLL that has been previously treated with a Bruton's tyrosine kinase (BTK) inhibitor. In one embodiment, the relapsed or refractory CLL/SLL is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib.

In the context of a cancer, for example, a hematological malignancy, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates are computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR). In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of NHL may be assessed by the International Workshop Criteria for Malignant Lymphoma (see Cheson et al., *J. Clin. Oncol.* 2014, 32(27):3059-3068) and the Deauville Criteria for fluorodeoxyglucose-positron emission tomography (FDG-PET) scan interpretation (Itti et al., *Eur. J. Nucl. Med. Mol. Imaging,* 2013, 40(9):1312-20; Meignan et al., *Leuk Lymphoma,* 2014, 55(1):31-37) ("Lugano criteria"), using the response and end point definition shown in Tables 1-3.

TABLE 1

Criteria for Involvement of Site.

| Tissue Site | Clinical | FDG Avidity | Test | Positive Finding |
|---|---|---|---|---|
| Lymph nodes | Palpable | FDG-avid histologies | PET/CT | Increase FDG uptake |
| | | Nonavid disease | CT | Unexplained node enlargement |
| Spleen | Palpable | FDG-avid histologies | PET/CT | Diffuse uptake, solitary mass, miliary lesions, nodules |
| | | Nonavid disease | CT | >13 cm in vertical length, mass, nodules |
| Liver | Palpable | FDG-avid histologies | PET/CT | Diffuse uptake, mass |
| | | Nonavid disease | CT | Nodules |
| CNS | Signs, symptoms | N/A | CT | Mass lesion(s) |
| | | | MRI | Leptomeningeal infiltration, mass lesions |
| | | | CSF assessment | Cytology, flow cytometry |

TABLE 1-continued

| Criteria for Involvement of Site. | | | | |
|---|---|---|---|---|
| Tissue Site | Clinical | FDG Avidity | Test | Positive Finding |
| Other (eg, skin, lung, GI tract, bone, bone marrow) | Site dependent | N/A | PET/CT[a], biopsy | Lymphoma involvement |

CNS = central nervous system;

CSF = cerebrospinal fluid;

CT = computed tomography;

FDG = fluorodeoxyglucose;

GI = gastrointestinal;

MRI = magnetic resonance imaging;

PET = positron emission tomography;

N/A = not applicable.

[a]PET/CT is adequate for determination of bone marrow involvement and can considered highly suggestive for involvement of other extralymphatic sites. Biopsy confirmation of those sites can be considered if necessary.

TABLE 2

| Lugano Response Criteria for Non-Hodgkin Lymphoma. | | | |
|---|---|---|---|
| Response | Site | PET/CT (metabolic response) | CT (Radiologic response) |
| Complete response | Lymph nodes and extralymphatic sites | Score 1, 2, 3 with or without residual mass on 5-PS (Table 3) | All of the following:<br>Target nodes/nodal masses must regress to ≤1.5 cm in LDi<br>No extralymphatic sites of disease |
| | Non-measured lesion | N/A | Absent |
| | Organ enlargement | N/A | Regress to normal |
| | New Lesions | None | None |
| | Bone Marrow | No evidence of FDG-avid disease in marrow | Normal by morphology; if inderterminate, IHC negative[a] |
| Partial Response | Lymph nodes and extralymphatic sites | Score 4 or 5 on 5-PS with reduced uptake compared with baseline and residual mass(es) of any size<br>At interim these findings suggest responding disease<br>At end of treatment these findings may indicate residual disease | All of the following:<br>≥50% decrease in SPD of up to 6 target measureable nodes and extranodal sites<br>When a lesion is too small to measure on CT, assign 5 mm × 5 mm as the default value<br>When no longer visible, 0 mm × 0 mm<br>For a node >5 mm × 5 mm, but smaller than normal, use actual measurement for calculation |
| | Non-measured lesion | N/A | Absent/normal, regressed, but no increase |
| | Organ enlargement | N/A | Spleen must have regressed by >50% in length beyond normal |
| | New Lesions | None | None |
| | Bone Marrow | Residual uptake higher than uptake in normal marrow but reduced compared with baseline. If persistent focal changes in the marrow in the context of nodal response, consider MRI or biopsy or interval scan | N/A |
| Stable Disease | Target nodes/nodal masses, extranodal lesions | Score 4 or 5 on 5-PS with no significant change in FDG uptake from baseline | <50% decrease from baseline of up to 6 dominant, measureable nodes and extranodal sites<br>No criteria for progressive disease are met |
| | Non-measured lesion | N/A | No increase consistent with progression |
| | Organ enlargement | N/A | No increase consistent with progression |
| | New Lesions | None | None |
| | Bone Marrow | No change from baseline | N/A |

TABLE 2-continued

Lugano Response Criteria for Non-Hodgkin Lymphoma.

| Response | Site | PET/CT (metabolic response) | CT (Radiologic response) |
|---|---|---|---|
| Progressive Disease | Lymph nodes and extralymphatic sites | Score 4 or 5 on 5-PS with an increase in intensity of uptake compared with baseline and/or<br>New FDG-avid foci consistent with lymphoma | At least one of the following:<br>PPD progression:<br>An individual node/lesion must be abnormal with:<br>LDi >1.5 cm and<br>Increase by ≥50% from PPD nadir and<br>An increase in LDi or SDi from nadir<br>0.5 cm for lesions ≤2 cm<br>1.0 cm for lesions >2 cm<br>In the setting of splenomegaly, splenic length must increase by >50% of the extent of its prior increase above baseline (eg, a 15 cm spleen must increase to >16 cm). If no splenomegaly, must increase by at least 2 cm from baseline must increase by at least 2 cm from baseline<br>New or recurrent splenomegaly |
| | Non-measured lesion | None | New or clear progression of preexisting nonmeasured lesions |
| | New Lesions | New FDG-avid foci consistent with lymphoma rather than another etiology (eg, infection, inflammation). If uncertain etiology, consider biopsy or interval scan | Regrowth of previously resolved lesions<br>A new node >1.5 cm in any axis<br>A new extranodal site > 1.0 cm in any axis; if <1.0 cm in any axis, its presence must be unequivocal and must be attributable to lymphoma<br>Assessable disease of any size unequivocally attributable to lymphoma |
| | Bone Marrow | New of recurrent FDG-avid foci | New or recurrent involvement |

CMR = complete metabolic response;

LDi = longest transverse diameter of a lesion;

PPD = cross product of the LDi and perpendicular diameter;

SDi = shortest axis perpendicular to the LDi;

SPD = sum of the product of the perpendicular diameters for multiple lesions;

N/A = not applicable.

[a]Required for CR if bone marrow involvement at baseline

[b] In Waldeyer's ring or extranodal sites with high physiologic uptake or with activation within spleen or marrow; (eg with chemotherapy or myeloid colony stimulating factors), uptake may be greater than normal mediastinum and/or liver. In this circumstance, CMR may be inferred if uptake at sites of initial involvement is no greater than surrounding normal tissue.

[c] FDG-avid lymphomas should have response assessed by PET-CT. Some diseases can typically be followed with CT alone (i.e., marginal zone lymphoma).

[d] PET should be done with contrast-enhanced diagnostic CT and can be done simultaneously or at separate procedures.

TABLE 3

| PET Five Point Scale (5-PS). | |
|---|---|
| 1 | No uptake above background |
| 2 | Uptake ≤ mediastinum |
| 3 | Uptake > mediastinum but ≤ liver |
| 4 | Uptake moderately > liver |
| 5 | Uptake markedly higher than liver and/or new lesions |
| X | New areas of uptake unlikely to be related to lymphoma |

[a] The Deauville five-point scale (5PS) is an internationally recommended scale for clinical routine and clinical trials using FDG-PET/CT in the initial staging and assessment of treatment response in Hodgkin lymphoma (HL) and certain types of non-Hodgkin lymphomas (NHL).

In one embodiment, the treatment response of CLL/SLL may be assessed by the International Workshop on Chronic Lymphocytic Leukemia criteria (see Hallek, M, et al. iwCLL guidelines for diagnosis, indications for treatment, response assessment, and supportive management of CLL. *Blood,* 131(25), 2745-2760 (2018)) (Table 4).

TABLE 4

Response Definition after Treatment for Chronic Lymphocytic Leukemia Patients.

| Group | Parameter | CR | PR | PD | SD |
|---|---|---|---|---|---|
| A | Lymph nodes | None >1.5 cm | Decrease ≥50% (from the baseline)[a] | Increase ≥50% from baseline or from response | Change of −49% to +49% |
| | Liver and/or spleen size[b] | Spleen size, 13 cm; liver size normal | Decrease ≥ 50% (from the baseline) | Increase ≥ 50% from baseline or from response | Change of −49% to +49% |
| | Constitutional symptoms | None | Any | Any | Any |
| | Circulating lymphocyte count | Normal | Decrease ≥50% from baseline | Increase ≥50% over baseline | Change of −49% to +49% |
| B | Platelet count | ≥100 × $10^9$/L | ≥100 × $10^9$/L or increase ≥50% over baseline | Decrease of ≥50% from baseline secondary to CLL | Change of −49% to +49% |
| | Hemoglobin | ≥11.0 g/dL (untransfused and without erythropoietin) | ≥11.0 g/dL or increase ≥50% over baseline | Decrease of >2 g/dL from baseline secondary to CLL | Increase, 11.0 g/dL or <50% over baseline, or decrease <2 g/dL |
| | Marrow | Normocellular, no CLL cells, no B-lymphoid nodules | Presence of CLL cells, or of B-lymphoid nodules, or not done | Increase of CLL cells by ≥50% on successive biopsies | No change in marrow infiltrate |

CR = complete remission (all of the criteria have to be met);

PD = progressive disease (at least 1 of the criteria of group A or group B has to be met);

PR = partial remission (for a PR, at least 2 of the parameters of group A and 1 parameter of group B need to improve if previously abnormal; if only 1 parameter of both groups A and B is abnormal before therapy, only 1 needs to improve);

SD = stable disease (all of the criteria have to be met; constitutional symptoms alone do not define PD).

[a]Sum of the products of 6 or fewer lymph nodes (as evaluated by CT scans and physical examination in clinical trials or by physical examination in general practice).

[b]Spleen size is considered normal if <13 cm. There is not firmly established international consensus of the size of a normal liver; therefore, liver size should be evaluated by imaging and manual palpation in clinical trials and be recorded according to the definition used in a study protocol.

In one embodiment, the treatment response of CLL/SLL may be assessed by the Eastern Cooperative Oncology Group (ECOG) performance status (Table 5).

TABLE 5

| ECOG Performance Status. | |
|---|---|
| Grade | ECOG |
| 0 | Fully active, able to carry on all pre-disease performance without restriction. |
| 1 | Restricted in physically strenuous activity but ambulatory and able to carry out work of a light or sedentary nature, e.g., light house work, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair. |
| 5 | Dead. |

ECOG = Eastern Cooperative Oncology Group, Robert Comis, MD, Group Chair.
Source: Oken M, et al. Toxicity and response criteria of the Eastern Cooperative Oncology Group. *Am J Clin Oncol*, 5(6): 649-655 (1982).

In certain embodiments, stable disease or lack thereof can be determined by methods known in the art such as evaluation of patient symptoms, physical examination, visualization of the tumor that has been imaged, for example using FDG-PET (fluorodeoxyglucose positron emission tomography), PET/CT (positron emission tomography/computed tomography) scan, MRI (magnetic resonance imaging) of the brain and spine, CSF (cerebrospinal fluid), ophthalmologic exams, vitreal fluid sampling, retinal photograph, bone marrow evaluation and other commonly accepted evaluation modalities.

As used herein and unless otherwise indicated, the terms "co-administration" and "in combination with" include the administration of one or more therapeutic agents (for example, a compound provided herein and another anti-cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with another therapeutic agent.

5.2 Salts and Solid Forms Comprising Compound 1

In certain embodiments, provided herein is a solid form comprising Compound 1:

1

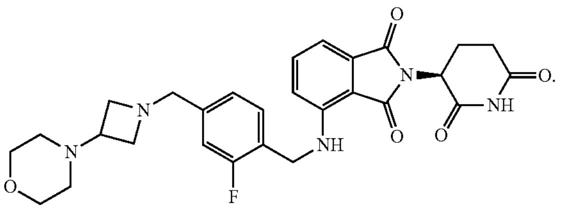

Compound 1 has the chemical name (S)-2-(2,6-dioxopiperidin-3-yl)-4-((2-fluoro-4-((3-morpholinoazetidin-1-yl)methyl)benzyl)amino)isoindoline-1,3-dione. Methods of preparing Compound 1 are described in U.S. application Ser. No. 16/390,815, which is incorporated herein by reference in its entirety.

In one embodiment, the solid form comprises a free base of Compound 1. In one embodiment, the solid form comprises a salt of Compound 1. In one embodiment, the solid form comprises a hydrochloride salt of Compound 1. In one embodiment, the solid form comprises a fumarate salt of Compound 1. In one embodiment, the solid form comprises a tosylate salt of Compound 1. In one embodiment, the solid form comprises a maleate salt of Compound 1. In one embodiment, the solid form comprises a besylate salt of Compound 1.

In one embodiment, the solid form is crystalline. In one embodiment, the solid form is a hydrate. In one embodiment, the solid form is an anhydrate. In one embodiment, the solid form is a solvate. In one embodiment, the solid form is non-solvated. In one embodiment, the solid form is amorphous.

The solid forms provided may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

Also provided herein are salts of Compound 1. In one embodiment, the salt is a hydrochloride salt of Compound 1. In one embodiment, the salt is a fumarate salt of Compound 1. In one embodiment, the salt is a tosylate salt of Compound 1. In one embodiment, the salt is a maleate salt of Compound 1. In one embodiment, the salt is a besylate salt of Compound 1.

Without being limited by any particular theory, the acids are associated with one or more basic nitrogen of Compound 1. Without being limited by any particular theory, the pKa of the azetidine nitrogen of Compound 1 is estimated to be about 7.7, and the pKa of the morpholine nitrogen of Compound 1 is estimated to be about 2.12.

The purity of the solid forms and salts provided herein may be determined by standard analytical methods, such as thin layer chromatography (TLC), gel electrophoresis, gas chromatography, high performance liquid chromatography (HPLC), and mass spectrometry.

While not intending to be bound by any particular theory, certain solid forms and salts are characterized by physical properties, e.g., stability, solubility and dissolution rate, appropriate for pharmaceutical and therapeutic dosage forms. Moreover, while not wishing to be bound by any particular theory, certain solid forms and salts are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms and salts suitable for the manufacture of a solid dosage form.

Such properties can be determined using particular analytical chemical techniques, including solid-state analytical techniques (e.g., X-ray diffraction, microscopy, spectroscopy and thermal analysis), as described herein and known in the art. While not intending to be bound by any particular theory, certain solid forms and salts provided herein exhibit suitable pharmaceutical properties, e.g., pharmaceutical kinetics, pharmaceutical dynamics, half-life, $C_{max}$, and bioavailability. Such properties can be determined using assays known to the skilled artisan.

(a) Free Base of Compound 1

In some embodiments, provided herein is a free base of Compound 1. It is contemplated that a free base of Compound 1 can exist in a variety of solid forms. Such solid forms include crystalline solids, such as polymorphs, solvates and hydrates of crystalline free base of Compound 1, as well as amorphous solids, or mixtures thereof.

In one embodiment, provided herein is a solid form comprising a free base of Compound 1. In one embodiment, the solid form is a solvate of a free base of Compound 1. In one embodiment, the solid form is a hydrate of a free base of Compound 1. In one embodiment, the solid form is a non-solvated form of a free base of Compound 1. In one embodiment, the solid form is a desolvated form of a free base of Compound 1. In one embodiment, the solid form is an anhydrous form (anhydrate) of a free base of Compound 1. In one embodiment, the solid form is a dehydrated form of a free base of Compound 1.

(i) Form A of Free Base of Compound 1

In certain embodiments, provided herein is Form A of a free base of Compound 1.

In one embodiment, Form A is crystalline. In one embodiment, Form A is substantially crystalline. In one embodiment, Form A is moderately crystalline. In one embodiment, Form A is partially crystalline.

A representative XRPD pattern of Form A is provided in FIG. 1.

In one embodiment, provided herein is a solid form comprising a free base of Compound 1, characterized by 1, 2, 3, 4, 5, 6, 7, 8, 9, 10, 11, 12, 13, 14, 15, 16, or all of the peaks located at approximately the following positions: 4.5, 11.4, 12.6, 13.3, 15.3, 15.9, 18.1, 19.1, 20.1, 20.9, 21.6, 22.6, 23.9, 25.4, 26.3, 28.1, and 29.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 4.5, 15.3, and 18.1° 2θ. In one embodiment, the XRPD pattern further comprises peaks at approximately 13.3 and 15.9° 2θ. In one embodiment, the XRPD pattern further comprises peaks at approximately 20.1 and 20.9° 2θ. In one embodiment, the XRPD pattern comprises peaks at approximately 4.5, 13.3, 15.3, 15.9, 18.1, 19.1, 20.1, 20.9, 21.6, and 26.3° 2θ.

In one embodiment, provided herein is a solid form comprising a free base of Compound 1, characterized by an XRPD pattern comprising peaks at approximately 4.5° 2θ. In one embodiment, the XRPD pattern comprises peaks at approximately 4.5, 11.4, and 12.6° 2θ. In one embodiment, the XRPD pattern comprises peaks at approximately 4.5, 11.4, 12.6, 13.3, and 15.3° 2θ. In one embodiment, the XRPD pattern comprises peaks at approximately 4.5, 11.4, 12.6, 13.3, 15.3, 15.9, and 18.1° 2θ.

In one embodiment, provided herein is a solid form comprising a free base of Compound 1, characterized by an XRPD pattern that matches the XRPD pattern presented in FIG. 1.

In one embodiment, the XRPD patterns are obtained using Cu Kα radiation.

Representative thermal gravimetric analysis (TGA) and differential scanning calorimetry (DSC) thermograms of Form A are provided in FIG. 2. In one embodiment, provided herein is a solid form comprising a free base of Compound 1, which exhibits a weight loss of about 1.3% upon heating from about 25° C. to about 50° C., and a weight loss of about 1.4% upon heating from about 50° C. to about 200° C. In one embodiment, provided herein is a solid form comprising a free base of Compound 1, characterized by a TGA thermogram that matches the TGA thermogram presented in FIG. 2.

In one embodiment, provided herein is a solid form comprising a free base of Compound 1, which exhibits, as characterized by DSC, a first thermal event (endo) with a peak temperature of about 68° C., and a second thermal event (endo) with a peak temperature of about 112° C. In one embodiment, provided herein is a solid form comprising a free base of Compound 1, characterized by a DSC thermogram that matches the DSC thermogram presented in FIG. 2.

In one embodiment, Form A of a free base of Compound 1 is prepared by slurrying a free base of Compound 1 in water (e.g., about 40° C., about 6 days).

In one embodiment, provided herein is a solid form comprising Form A of a free base of Compound 1 and amorphous free base of Compound 1. In one embodiment, provided herein is a solid form comprising Form A of a free base Compound 1 and one or more other crystalline forms of a free base of Compound 1 provided herein. In one embodiment, provided herein is a solid form comprising Form A of a free base of Compound 1 and one or more forms (e.g., amorphous or crystalline) of a salt of Compound 1 provided herein.

(ii) Form B of Free Base of Compound 1

In certain embodiments, provided herein is Form B of a free base of Compound 1.

In one embodiment, Form B is crystalline. In one embodiment, Form B is substantially crystalline. In one embodiment, Form B is moderately crystalline. In one embodiment, Form B is partially crystalline.

A representative XRPD pattern of Form B is provided in FIG. 3.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 4.5, 4.8, 9.6, 10.7, 11.4, 12.0, 13.3, 13.7, 14.9, 15.7, 17.3, 18.7, 19.0, 20.2, 20.7, 21.3, 21.4, 22.1, 22.9, 23.8, 24.5, 25.4, 26.2, 26.9, and 28.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 4.8, 9.6, and 14.9° 2θ. In one embodiment, the XRPD pattern further comprises peaks at approximately 18.7 and 22.1° 2θ. In one embodiment, the XRPD pattern further comprises peaks at approximately 20.7 and 21.4° 2θ. In one embodiment, the XRPD pattern comprises peaks at approximately 4.5, 4.8, 9.6, 14.9, 15.7, 17.3, 18.7, 19.0, 20.7, 21.3, 21.4, 22.1, 22.9, and 28.2° 2θ.

In one embodiment, provided herein is a solid form comprising a free base of Compound 1, characterized by an XRPD pattern comprising peaks at approximately 4.5, 4.8, and 9.6° 2θ. In one embodiment, the XRPD pattern comprises peaks at approximately 4.5, 4.8, 9.6, 10.7, and 11.4° 2θ. In one embodiment, the XRPD pattern comprises peaks at approximately 4.5, 4.8, 9.6, 10.7, 11.4, 13.3, and 13.7° 2θ. In one embodiment, the XRPD pattern comprises peaks at approximately 4.5, 4.8, 9.6, 10.7, 11.4, 13.3, 13.7, 14.9, and 15.7° 2θ.

In one embodiment, provided herein is a solid form comprising a free base of Compound 1, characterized by an XRPD pattern that matches the XRPD pattern presented in FIG. 3.

In one embodiment, the XRPD patterns are obtained using Cu Kα radiation.

Representative thermal gravimetric analysis (TGA) and differential scanning calorimetry (DSC) thermograms of Form B is provided in FIG. 4. In one embodiment, provided herein is a solid form comprising a free base of Compound 1, which exhibits a weight loss of about 0.9% upon heating from about 25° C. to about 225° C. In one embodiment, provided herein is a solid form comprising a free base of Compound 1, characterized by a TGA thermogram that matches the TGA thermogram presented in FIG. 4.

In one embodiment, provided herein is a solid form comprising a free base of Compound 1, which exhibits, as characterized by DSC, a first thermal event (endo) with a peak temperature of about 82° C., a second thermal event (endo) with a peak temperature of about 107° C., and a third thermal event (endo) with a peak temperature of about 138° C. In one embodiment, provided herein is a solid form comprising a free base of Compound 1, characterized by a DSC thermogram that matches the DSC thermogram presented in FIG. 4.

In one embodiment, Form B of a free base of Compound 1 is prepared by crystallizing a free base of Compound 1 from a solvent/anti-solvent system (e.g., at room temperature), wherein the solvent is acetone and the anti-solvent is water.

In one embodiment, provided herein is a solid form comprising Form B of a free base of Compound 1 and amorphous free base of Compound 1. In one embodiment, provided herein is a solid form comprising Form B of a free base Compound 1 and one or more other crystalline forms of a free base of Compound 1 provided herein. In one embodiment, provided herein is a solid form comprising Form B of a free base of Compound 1 and one or more forms (e.g., amorphous or crystalline) of a salt of Compound 1 provided herein.

(b) Hydrochloride Salt of Compound 1

In some embodiments, provided herein is a hydrochloride salt of Compound 1. It is contemplated that a hydrochloride salt of Compound 1 can exist in a variety of solid forms. Such solid forms include crystalline solids, such as polymorphs, solvates and hydrates of crystalline hydrochloride salt of Compound 1, as well as amorphous solids, or mixtures thereof.

In one embodiment, provided herein is a solid form comprising a hydrochloride salt of Compound 1. In one embodiment, the solid form is a solvate of a hydrochloride salt of Compound 1. In one embodiment, the solid form is a hydrate of a hydrochloride salt of Compound 1. In one embodiment, the solid form is a non-solvated form of a hydrochloride salt of Compound 1. In one embodiment, the solid form is a desolvated form of a hydrochloride salt of Compound 1. In one embodiment, the solid form is an anhydrous form (anhydrate) of a hydrochloride salt of Compound 1. In one embodiment, the solid form is a dehydrated form of a hydrochloride salt of Compound 1.

In some embodiments, the molar ratio of Compound 1 to hydrochloric acid in the solid form ranges from about 1:1 to about 1:2. In one embodiment, the molar ratio is about 1:2 (i.e., bis-hydrochloride salt). In another embodiment, the molar ratio is about 1:1 (i.e., mono-hydrochloride salt).

(i) Form A of Hydrochloride Salt of Compound 1

In certain embodiments, provided herein is Form A of a hydrochloride salt of Compound 1.

In one embodiment, Form A is crystalline. In one embodiment, Form A is substantially crystalline. In one embodiment, Form A is moderately crystalline. In one embodiment, Form A is partially crystalline.

In one embodiment, the molar ratio of Compound 1 to hydrochloric acid in Form A is about 1:1. In one embodiment, Form A is a mono-hydrochloride salt of Compound 1.

In one embodiment, Form A is a hydrate of a hydrochloride salt of Compound 1. In one embodiment, Form A is a channel hydrate of a hydrochloride salt of Compound 1.

A representative XRPD pattern of Form A of a hydrochloride salt of Compound 1 is provided in FIG. 5.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, 27, or all of the peaks located at approximately the following positions: 4.2, 7.8, 11.1, 12.4, 15.1, 15.5, 16.3, 17.1, 17.3, 17.9, 18.2, 18.9, 19.2, 20.1, 20.4, 20.7, 21.7, 22.4, 23.0, 24.4, 24.8, 25.7, 27.5, 28.1, 29.1, 29.8, 30.2, and 30.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 15.1, 16.3, and 20.7° 2θ. In one embodiment, the XRPD pattern further comprises peaks at approximately 7.8 and 22.4° 2θ. In one embodiment, the XRPD pattern further comprises peaks at approximately 18.2, 18.9, and 24.8° 2θ. In one embodiment, the XRPD pattern comprises peaks at approximately 7.8, 15.1, 16.3, 17.9, 18.2, 18.9, 19.2, 20.4, 20.7, 21.7, 22.4, and 24.8° 2θ.

In one embodiment, provided herein is a solid form comprising a hydrochloride salt of Compound 1, characterized by an XRPD pattern comprising peaks at approximately 4.2, 7.8, and 11.1° 2θ. In one embodiment, the XRPD pattern comprises peaks at approximately 4.2, 7.8, 11.1, 12.4, and 15.1° 2θ. In one embodiment, the XRPD pattern comprises peaks at approximately 4.2, 7.8, 11.1, 12.4, 15.1, 15.5, and 16.3° 2θ. In one embodiment, the XRPD pattern comprises peaks at approximately 4.2, 7.8, 11.1, 12.4, 15.1, 15.5, 16.3, 17.1, and 17.3° 2θ.

In one embodiment, provided herein is a solid form comprising a hydrochloride salt of Compound 1, characterized by an XRPD pattern that matches the XRPD pattern presented in FIG. 5.

In one embodiment, the XRPD patterns are obtained using Cu Kα radiation.

Representative thermal gravimetric analysis (TGA) and differential scanning calorimetry (DSC) thermograms of Form A of a hydrochloride salt of Compound 1 are provided in FIG. 6. In one embodiment, provided herein is a solid form comprising a hydrochloride salt of Compound 1, which exhibits a weight loss of about 1.5% upon heating from about 25° C. to about 200° C., and a weight loss of about 2.7% upon heating from about 200° C. to about 230° C. In one embodiment, provided herein is a solid form comprising a hydrochloride salt of Compound 1, characterized by a TGA thermogram that matches the TGA thermogram presented in FIG. 6.

In one embodiment, provided herein is a solid form comprising a hydrochloride salt of Compound 1, which exhibits, as characterized by DSC, a first thermal event (endo) with a peak temperature of about 218° C., and a second thermal event (exo) with a peak temperature of about 227° C. In one embodiment, provided herein is a solid form comprising a hydrochloride salt of Compound 1, characterized by a DSC thermogram that matches the DSC thermogram presented in FIG. 6. The melting point of Form A of a hydrochloride salt of Compound 1 may vary depending on crystallinity and crystal structure defects.

A representative dynamic vapor sorption (DVS) isotherm plot of the Form A of a hydrochloride salt of Compound 1 is provided in FIG. 7. In one embodiment, provided herein is a solid form comprising a hydrochloride salt of Compound 1, which exhibits a mass increase of about 3.0% when subjected to an increase in a relative humidity (RH) from about 0% to about 95%. In one embodiment, provided herein is a solid form comprising a hydrochloride salt of Compound 1, characterized by a DVS isotherm plot which matches the DVS isotherm plot presented in FIG. 7.

In one embodiment, Form A of a hydrochloride salt of Compound 1 has a crystal habit of small rod primary particles. A representative SEM image of Form A of a hydrochloride salt of Compound 1 is presented in FIG. 8.

In one embodiment, Form A of a hydrochloride salt of Compound 1 is prepared by slurrying a hydrochloride salt of Compound 1 in a solvent. In one embodiment, Form A of a hydrochloride salt of Compound 1 is prepared by slurrying Compound 1 free base and hydrochloric acid in a solvent. In one embodiment, the solvent is acetone, acetonitrile, anisole, DCM, DMAc, EtOH, EtOAc, ethyl formate, isopropyl acetate, MeOH, MEK, MTBE, 2-MeTHF, nitromethane, NMP, 2-propanol, tetrahydrofuran, toluene, water, a mixture of acetone and water (e.g., 95/5 v/v), a mixture of acetonitrile and water (e.g., 95/5 v/v), a mixture of 2-PrOH and water (e.g., 95/5 v/v), or a mixture of THF and water (e.g., 95/5 v/v). In one embodiment, the solvent is acetonitrile. In one embodiment, the slurring is conducted at room temperature. In one embodiment, the slurring is conducted at about 50° C. In one embodiment, the slurring is conducted for a time period of from about 1 day to about 7 days. In one embodiment, the slurring is conducted for about 2 days. In one embodiment, the slurring is conducted for about 7 days.

In one embodiment, provided herein is a solid form comprising Form A of a hydrochloride salt of Compound 1 and one or more forms of a free base of Compound 1 (e.g., amorphous form and crystalline forms). In one embodiment, provided herein is a solid form comprising Form A of a hydrochloride salt of Compound 1 and amorphous hydrochloride salt of Compound 1. In one embodiment, provided herein is a solid form comprising Form A of a hydrochloride salt Compound 1 and one or more other crystalline forms of a hydrochloride salt of Compound 1 provided herein. In one embodiment, provided herein is a solid form comprising Form A of a hydrochloride salt of Compound 1 and one or more forms (e.g., amorphous or crystalline) of a salt of Compound 1 provided herein.

(ii) Form B of Hydrochloride Salt of Compound 1

In certain embodiments, provided herein is Form B of a hydrochloride salt of Compound 1.

In one embodiment, Form B is crystalline. In one embodiment, Form B is substantially crystalline. In one embodiment, Form B is moderately crystalline. In one embodiment, Form B is partially crystalline.

A representative XRPD pattern of Form B of a hydrochloride salt of Compound 1 is provided in FIG. 9.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, or all of the peaks located at approximately the following positions: 6.7, 11.6, 13.5, 14.2, 14.6, 16.5, 17.2, 17.5, 18.1, 18.5, 19.6, 20.3, 21.1, 21.6, 21.9, 22.4, 23.2, 23.7, 24.2, 24.8, 26.1, 26.7, 27.0, 27.7, 28.2, 29.5, and 30.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 17.5, 21.6, and 24.8° 2θ. In one embodiment, the XRPD pattern further comprises peaks at approximately 21.1 and 27.0° 2θ. In one embodiment, the XRPD pattern further comprises peaks at approximately 14.6, 17.2, and 20.3° 2θ. In one embodiment, the XRPD pattern comprises peaks at approximately 6.7, 14.6, 17.2, 17.5, 19.6, 20.3, 21.1, 21.6, 21.9, 22.4, 24.8, 26.7, 27.0, 27.7, and 29.5° 2θ.

In one embodiment, provided herein is a solid form comprising a hydrochloride salt of Compound 1, characterized by an XRPD pattern comprising peaks at approximately 6.7, 11.6, and 13.5° 2θ. In one embodiment, the XRPD pattern comprises peaks at approximately 6.7, 11.6, 13.5, 14.2, and 14.6° 2θ. In one embodiment, the XRPD pattern comprises peaks at approximately 6.7, 11.6, 13.5, 14.2, 14.6, 16.5, and 17.2° 2θ. In one embodiment, the XRPD pattern comprises peaks at approximately 6.7, 11.6, 13.5, 14.2, 14.6, 16.5, 17.2, 17.5, and 18.1° 2θ.

In one embodiment, provided herein is a solid form comprising a hydrochloride salt of Compound 1, characterized by an XRPD pattern that matches the XRPD pattern presented in FIG. 9.

In one embodiment, the XRPD patterns are obtained using Cu Kα radiation.

Representative thermal gravimetric analysis (TGA) and differential scanning calorimetry (DSC) thermograms of Form B of a hydrochloride salt of Compound 1 are provided in FIG. 10. In one embodiment, provided herein is a solid form comprising a hydrochloride salt of Compound 1, which exhibits a weight loss of about 1.6% upon heating from about 25° C. to about 175° C., and a weight loss of about 5.3% upon heating from about 175° C. to about 230° C. In one embodiment, provided herein is a solid form comprising a hydrochloride salt of Compound 1, characterized by a TGA thermogram that matches the TGA thermogram presented in FIG. 10.

In one embodiment, provided herein is a solid form comprising a hydrochloride salt of Compound 1, which exhibits, as characterized by DSC, a thermal event (exo) with a peak temperature of about 230° C. In one embodiment, provided herein is a solid form comprising a hydrochloride salt of Compound 1, characterized by a DSC thermogram that matches the DSC thermogram presented in FIG. 10.

In one embodiment, Form B of a hydrochloride salt of Compound 1 is prepared by slurrying free base of Compound 1 and about 2 equivalents of HCl in acetonitrile (e.g., at room temperature for about 5 days).

In one embodiment, provided herein is a solid form comprising Form B of a hydrochloride salt of Compound 1 and one or more forms of a free base of Compound 1 (e.g., amorphous form and crystalline forms). In one embodiment, provided herein is a solid form comprising Form B of a hydrochloride salt of Compound 1 and amorphous hydrochloride salt of Compound 1. In one embodiment, provided herein is a solid form comprising Form B of a hydrochloride salt Compound 1 and one or more other crystalline forms of a hydrochloride salt of Compound 1 provided herein. In one embodiment, provided herein is a solid form comprising Form B of a hydrochloride salt of Compound 1 and one or more forms (e.g., amorphous or crystalline) of a salt of Compound 1 provided herein.

(iii) Form C of Hydrochloride Salt of Compound 1

In certain embodiments, provided herein is Form C of a hydrochloride salt of Compound 1. A representative XRPD pattern of Form C of a hydrochloride salt of Compound 1 is provided in FIG. 21. In one embodiment, provided herein is a solid form comprising a hydrochloride salt of Compound 1, characterized by an XRPD pattern that matches the XRPD pattern presented in FIG. 21.

(c) Fumarate Salt of Compound 1

In some embodiments, provided herein is a fumarate salt of Compound 1. It is contemplated that a fumarate salt of Compound 1 can exist in a variety of solid forms. Such solid forms include crystalline solids, such as polymorphs, solvates and hydrates of crystalline fumarate salt of Compound 1, as well as amorphous solids, or mixtures thereof.

In one embodiment, provided herein is a solid form comprising a fumarate salt of Compound 1. In one embodiment, the solid form is a solvate of a fumarate salt of Compound 1. In one embodiment, the solid form is a hydrate of a fumarate salt of Compound 1. In one embodiment, the solid form is a non-solvated form of a fumarate salt of Compound 1. In one embodiment, the solid form is a desolvated form of a fumarate salt of Compound 1. In one embodiment, the solid form is an anhydrous form (anhydrate) of a fumarate salt of Compound 1. In one embodiment, the solid form is a dehydrated form of a fumarate salt of Compound 1.

In some embodiments, the molar ratio of Compound 1 to fumaric acid in the solid form ranges from about 1:1 to about 1:2. In one embodiment, the molar ratio is about 1:2 (i.e., bis-fumarate salt). In another embodiment, the molar ratio is about 1:1 (i.e., mono-fumarate salt).

(i) Form A of Fumarate Salt of Compound 1

In certain embodiments, provided herein is Form A of a fumarate salt of Compound 1.

In one embodiment, Form A is crystalline. In one embodiment, Form A is substantially crystalline. In one embodiment, Form A is moderately crystalline. In one embodiment, Form A is partially crystalline.

In one embodiment, the molar ratio of Compound 1 to fumaric acid in Form A is about 1:2. In one embodiment, Form A is a bis-fumarate salt of Compound 1.

In one embodiment, Form A is an unsolvated form of a fumarate salt of Compound 1.

A representative XRPD pattern of Form A of a fumarate salt of Compound 1 is provided in FIG. 11.

In one embodiment, provided herein is a solid form comprising a fumarate salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or all of the peaks located at approximately the following positions: 11.7, 12.2, 12.8, 13.8, 14.5, 14.7, 15.0, 15.2, 16.6, 17.1, 17.3, 17.7, 17.9, 18.3, 19.0, 19.4, 20.1, 20.5, 20.7, 21.4, 22.3, 22.9, 23.2, 23.4, 23.7, 24.3, 24.7, 24.9, 25.8, 26.6, and 27.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a fumarate salt of Compound 1, characterized by an XRPD pattern comprising peaks at approximately 22.3, 23.2, and 23.4° 2θ. In one embodiment, the XRPD pattern further comprises peaks at approximately 17.9 and 25.8° 2θ. In one embodiment, the XRPD pattern further comprises peaks at approximately 11.7 and 18.3° 2θ. In one embodiment, the XRPD pattern comprises peaks at approximately 11.7, 15.0, 17.9, 18.3, 19.4, 20.1, 22.3, 22.9, 23.2, 23.4, and 25.8° 2θ.

In one embodiment, provided herein is a solid form comprising a fumarate salt of Compound 1, characterized by an XRPD pattern comprising peaks at approximately 11.7, 12.2, and 12.8° 2θ. In one embodiment, the XRPD pattern comprises peaks at approximately 11.7, 12.2, 12.8, 13.8, and 14.5° 2θ. In one embodiment, the XRPD pattern comprises peaks at approximately 11.7, 12.2, 12.8, 13.8, 14.5, 14.7, and 15.0° 2θ. In one embodiment, the XRPD pattern comprises peaks at approximately 11.7, 12.2, 12.8, 13.8, 14.5, 14.7, 15.0, 15.2, and 16.6° 2θ.

In one embodiment, provided herein is a solid form comprising a fumarate salt of Compound 1, characterized by an XRPD pattern that matches the XRPD pattern presented in FIG. 11.

In one embodiment, the XRPD patterns are obtained using Cu Kα radiation.

Representative thermal gravimetric analysis (TGA) and differential scanning calorimetry (DSC) thermograms of Form A of a fumarate salt of Compound 1 are provided in FIG. 12. In one embodiment, provided herein is a solid form comprising a fumarate salt of Compound 1, which exhibits a weight loss of about 0.5% upon heating from about 25° C. to about 150° C., and a weight loss of about 7.9% upon heating from about 150° C. to about 205° C. In one embodiment, provided herein is a solid form comprising a fumarate salt of Compound 1, characterized by a TGA thermogram that matches the TGA thermogram presented in FIG. 12.

In one embodiment, provided herein is a solid form comprising a fumarate salt of Compound 1, which exhibits, as characterized by DSC, a thermal event (endo) with a peak temperature of about 198° C. In one embodiment, without being limited by any particular theory, the thermal event corresponds to melting. In one embodiment, provided herein is a solid form comprising a fumarate salt of Compound 1, characterized by a DSC thermogram that matches the DSC thermogram presented in FIG. 12.

In one embodiment, Form A of a fumarate salt of Compound 1 is prepared by slurrying a fumarate salt of Compound 1 in a solvent. In one embodiment, Form A of a fumarate salt of Compound 1 is prepared by slurrying Compound 1 free base and fumaric acid in a solvent. In one embodiment, the solvent is acetone, acetonitrile, anisole, DCM, EtOH, EtOAc, ethyl formate, isopropyl acetate, MeOH, MEK, MTBE, 2-MeTHF, nitromethane, 2-propanol, tetrahydrofuran, toluene, water, a mixture of acetone and water (e.g., 95/5 v/v), a mixture of acetonitrile and water (e.g., 95/5 v/v), a mixture of 2-PrOH and water (e.g., 95/5 v/v), or a mixture of THF and water (e.g., 95/5 v/v). In one embodiment, the solvent is acetonitrile. In one embodiment, the slurring is conducted at room temperature. In one embodiment, the slurring is conducted at about 50° C. In one embodiment, the slurring is conducted for a time period of from about 1 day to about 7 days. In one embodiment, the slurring is conducted for about 2 days. In one embodiment, the slurring is conducted for about 7 days.

In one embodiment, provided herein is a solid form comprising Form A of a fumarate salt of Compound 1 and one or more forms of a free base of Compound 1 (e.g., amorphous form and crystalline forms). In one embodiment, provided herein is a solid form comprising Form A of a fumarate salt of Compound 1 and amorphous fumarate salt of Compound 1. In one embodiment, provided herein is a solid form comprising Form A of a fumarate salt Compound 1 and one or more other crystalline forms of a fumarate salt of Compound 1. In one embodiment, provided herein is a solid form comprising Form A of a fumarate salt of Compound 1 and one or more forms (e.g., amorphous or crystalline) of a salt of Compound 1 provided herein.

(d) Tosylate Salt of Compound 1

In some embodiments, provided herein is a tosylate salt of Compound 1. It is contemplated that a tosylate salt of Compound 1 can exist in a variety of solid forms. Such solid forms include crystalline solids, such as polymorphs, solvates and hydrates of crystalline tosylate salt of Compound 1, as well as amorphous solids, or mixtures thereof.

In one embodiment, provided herein is a solid form comprising a tosylate salt of Compound 1. In one embodiment, the solid form is a solvate of a tosylate salt of Compound 1. In one embodiment, the solid form is a hydrate of a tosylate salt of Compound 1. In one embodiment, the solid form is a non-solvated form of a tosylate salt of Compound 1. In one embodiment, the solid form is a desolvated form of a tosylate salt of Compound 1. In one embodiment, the solid form is an anhydrous form (anhydrate) of a tosylate salt of Compound 1. In one embodiment, the solid form is a dehydrated form of a tosylate salt of Compound 1.

In some embodiments, the molar ratio of Compound 1 to p-toluenesulfonic acid in the solid form ranges from about 1:1 to about 1:2. In one embodiment, the molar ratio is about 1:2 (i.e., bis-tosylate salt). In another embodiment, the molar ratio is about 1:1 (i.e., mono-tosylate salt).

(i) Form A of Tosylate Salt of Compound 1

In certain embodiments, provided herein is Form A of a tosylate salt of Compound 1.

In one embodiment, Form A is crystalline. In one embodiment, Form A is substantially crystalline. In one embodiment, Form A is moderately crystalline. In one embodiment, Form A is partially crystalline.

In one embodiment, the molar ratio of Compound 1 to p-toluenesulfonic acid in Form A is about 1:1. In one embodiment, Form A is a mono-tosylate salt of Compound 1.

In one embodiment, Form A is an unsolvated form of a tosylate salt of Compound 1.

A representative XRPD pattern of Form A of a tosylate salt of Compound 1 is provided in FIG. 13.

In one embodiment, provided herein is a solid form comprising a tosylate salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, or all of the peaks located at approximately the following positions: 3.9, 6.8, 7.3, 7.8, 8.6, 10.9, 11.4, 12.1, 14.5, 15.4, 15.5, 15.7, 15.9, 16.4, 17.0, 17.6, 18.0, 18.6, 19.3, 19.7, 20.6, 21.2, 22.6, 23.0, 23.4, 23.8, 24.7, and 25.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a tosylate salt of Compound 1, characterized by an XRPD pattern comprising peaks at approximately 17.6, 18.0, and 23.8° 2θ. In one embodiment, the XRPD pattern further comprises peaks at approximately 15.7 and 20.6° 2θ. In one embodiment, the XRPD pattern further comprises peaks at approximately 24.7 and 25.0° 2θ. In one embodiment, the XRPD pattern comprises peaks at approximately 15.7, 16.4, 17.6, 18.0, 18.6, 20.6, 21.2, 23.4, 23.8, 24.7, and 25.0° 2θ.

In one embodiment, provided herein is a solid form comprising a tosylate salt of Compound 1, characterized by an XRPD pattern comprising peaks at approximately 3.9, 6.8, and 7.3° 2θ. In one embodiment, the XRPD pattern comprises peaks at approximately 3.9, 6.8, 7.3, 7.8, and 8.6° 2θ. In one embodiment, the XRPD pattern comprises peaks at approximately 3.9, 6.8, 7.3, 7.8, 8.6, 10.9, and 11.4° 2θ. In one embodiment, the XRPD pattern comprises peaks at approximately 3.9, 6.8, 7.3, 7.8, 8.6, 10.9, 11.4, 12.1, and 14.5° 2θ.

In one embodiment, provided herein is a solid form comprising a tosylate salt of Compound 1, characterized by an XRPD pattern that matches the XRPD pattern presented in FIG. 13.

In one embodiment, the XRPD patterns are obtained using Cu Kα radiation.

Representative thermal gravimetric analysis (TGA) and differential scanning calorimetry (DSC) thermograms of Form A of a tosylate salt of Compound 1 are provided in FIG. 14. In one embodiment, provided herein is a solid form comprising a tosylate salt of Compound 1, which exhibits a weight loss of about 1.0% upon heating from about 25° C. to about 200° C. In one embodiment, provided herein is a solid form comprising a tosylate salt of Compound 1, characterized by a TGA thermogram that matches the TGA thermogram presented in FIG. 14.

In one embodiment, provided herein is a solid form comprising a tosylate salt of Compound 1, which exhibits, as characterized by DSC, a thermal event (endo) with a peak temperature of about 189° C. In one embodiment, without being limited by any particular theory, the thermal event corresponds to melting. In one embodiment, provided herein is a solid form comprising a tosylate salt of Compound 1, characterized by a DSC thermogram that matches the DSC thermogram presented in FIG. 14.

In one embodiment, Form A of a tosylate salt of Compound 1 is prepared by slurrying a tosylate salt of Compound 1 in a solvent. In one embodiment, Form A of a tosylate salt of Compound 1 is prepared by slurrying Compound 1 free base and p-toluenesulfonic acid in a solvent. In one embodiment, the solvent is acetone, acetonitrile, anisole, DCM, EtOH, EtOAc, ethyl formate, isopropyl acetate, MeOH, MEK, MTBE, 2-MeTHF, nitromethane, 2-propanol, tetrahydrofuran, toluene, water, a mixture of acetone and water (e.g., 95/5 v/v), or a mixture of 2-PrOH and water (e.g., 95/5 v/v). In one embodiment, the solvent is acetonitrile. In one embodiment, the slurring is conducted at room temperature. In one embodiment, the slurring is conducted at about 50° C. In one embodiment, the slurring is conducted for a time period of from about 1 day to about 7 days. In one embodiment, the slurring is conducted for about 2 days. In one embodiment, the slurring is conducted for about 7 days.

In one embodiment, provided herein is a solid form comprising Form A of a tosylate salt of Compound 1 and one or more forms of a free base of Compound 1 (e.g., amorphous form and crystalline forms). In one embodiment, provided herein is a solid form comprising Form A of a tosylate salt of Compound 1 and amorphous tosylate salt of Compound 1. In one embodiment, provided herein is a solid form comprising Form A of a tosylate salt Compound 1 and one or more other crystalline forms of a tosylate salt of Compound 1. In one embodiment, provided herein is a solid form comprising Form A of a tosylate salt of Compound 1 and one or more forms (e.g., amorphous or crystalline) of a salt of Compound 1 provided herein.

(ii) Additional Forms of Tosylate Salt of Compound 1

In certain embodiments, provided herein is Form B of a tosylate salt of Compound 1. A representative XRPD pattern of Form B of a tosylate salt of Compound 1 is provided in FIG. 22 (as part of an overlay plot). In one embodiment, provided herein is a solid form comprising a tosylate salt of Compound 1, characterized by an XRPD pattern that matches the XRPD pattern for Form B as presented in FIG. 22.

In certain embodiments, provided herein is Form C of a tosylate salt of Compound 1. A representative XRPD pattern of Form C of a tosylate salt of Compound 1 is provided in FIG. 22 (as part of an overlay plot). In one embodiment, provided herein is a solid form comprising a tosylate salt of Compound 1, characterized by an XRPD pattern that matches the XRPD pattern for Form C as presented in FIG. 22.

In certain embodiments, provided herein is Form D of a tosylate salt of Compound 1. A representative XRPD pattern of Form D of a tosylate salt of Compound 1 is provided in FIG. 22 (as part of an overlay plot). In one embodiment, provided herein is a solid form comprising a tosylate salt of Compound 1, characterized by an XRPD pattern that matches the XRPD pattern for Form D as presented in FIG. 22.

(e) Maleate Salt of Compound 1

In some embodiments, provided herein is a maleate salt of Compound 1. It is contemplated that a maleate salt of Compound 1 can exist in a variety of solid forms. Such solid forms include crystalline solids, such as polymorphs, solvates and hydrates of crystalline maleate salt of Compound 1, as well as amorphous solids, or mixtures thereof.

In one embodiment, provided herein is a solid form comprising a maleate salt of Compound 1. In one embodiment, the solid form is a solvate of a maleate salt of Compound 1. In one embodiment, the solid form is a hydrate of a maleate salt of Compound 1. In one embodiment, the solid form is a non-solvated form of a maleate salt of Compound 1. In one embodiment, the solid form is a desolvated form of a maleate salt of Compound 1. In one embodiment, the solid form is an anhydrous form (anhydrate) of a maleate salt of Compound 1. In one embodiment, the solid form is a dehydrated form of a maleate salt of Compound 1.

In some embodiments, the molar ratio of Compound 1 to maleic acid in the solid form ranges from about 1:1 to about 1:2. In one embodiment, the molar ratio is about 1:2 (i.e., bis-maleate salt). In another embodiment, the molar ratio is about 1:1 (i.e., mono-maleate salt).

(i) Form A of Maleate Salt of Compound 1

In certain embodiments, provided herein is Form A of a maleate salt of Compound 1.

In one embodiment, Form A is crystalline. In one embodiment, Form A is substantially crystalline. In one embodiment, Form A is moderately crystalline. In one embodiment, Form A is partially crystalline.

In one embodiment, the molar ratio of Compound 1 to maleic acid in Form A is about 1:1. In one embodiment, Form A is a mono-maleate salt of Compound 1. In one embodiment, the molar ratio of Compound 1 to maleic acid in Form A is about 1:2. In one embodiment, Form A is a bis-maleate salt of Compound 1. In one embodiment, Form A is a mixture of mono-maleate salt and bis-maleate salt of Compound 1.

In one embodiment, Form A is an unsolvated form of a maleate salt of Compound 1. In one embodiment, Form A is a solvate of a maleate salt of Compound 1.

A representative XRPD pattern of Form A of a maleate salt of Compound 1 is provided in FIG. 15.

In one embodiment, provided herein is a solid form comprising a maleate salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, 27, 28, or all of the peaks located at approximately the following positions: 6.0, 11.6, 11.9, 12.5, 13.3, 13.9, 15.2, 16.2, 17.0, 17.6, 17.7, 18.0, 18.4, 18.9, 19.3, 19.8, 20.0, 22.2, 22.4, 22.7, 23.1, 23.3, 23.6, 24.0, 24.4, 25.1, 25.6, 26.0, and 26.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a maleate salt of Compound 1, characterized by an XRPD pattern comprising peaks at approximately 17.6, 24.4, and 26.9° 2θ. In one embodiment, the XRPD pattern further comprises peaks at approximately 18.0, 18.4, and 19.3° 2θ. In one embodiment, the XRPD pattern further comprises peaks at approximately 19.8 and 24.0° 2θ. In one embodiment, the XRPD pattern comprises peaks at approximately 11.9, 17.6, 18.0, 18.4, 19.3, 19.8, 24.0, 24.4, 25.1, 26.0, and 26.9° 2θ.

In one embodiment, provided herein is a solid form comprising a maleate salt of Compound 1, characterized by an XRPD pattern comprising peaks at approximately 6.0, 11.6, and 11.9° 2θ. In one embodiment, the XRPD pattern comprises peaks at approximately 6.0, 11.6, 11.9, 12.5, and 13.3° 2θ. In one embodiment, the XRPD pattern comprises peaks at approximately 6.0, 11.6, 11.9, 12.5, 13.3, 13.9, and 15.2° 2θ. In one embodiment, the XRPD pattern comprises peaks at approximately 6.0, 11.6, 11.9, 12.5, 13.3, 13.9, 15.2, 16.2, and 17.0° 2θ.

In one embodiment, provided herein is a solid form comprising a maleate salt of Compound 1, characterized by an XRPD pattern that matches the XRPD pattern presented in FIG. 15.

In one embodiment, the XRPD patterns are obtained using Cu Kα radiation.

Representative thermal gravimetric analysis (TGA) and differential scanning calorimetry (DSC) thermograms of Form A of a maleate salt of Compound 1 are provided in FIG. 16. In one embodiment, provided herein is a solid form comprising a maleate salt of Compound 1, which exhibits a weight loss of about 0.2% upon heating from about 25° C. to about 150° C., and a weight loss of about 8.8% upon heating from about 150° C. to about 185° C. In one embodiment, provided herein is a solid form comprising a maleate salt of Compound 1, characterized by a TGA thermogram that matches the TGA thermogram presented in FIG. 16.

In one embodiment, provided herein is a solid form comprising a maleate salt of Compound 1, which exhibits, as characterized by DSC, a thermal event (endo) with a peak temperature of about 174° C. In one embodiment, without being limited by any particular theory, the thermal event corresponds to melting. In one embodiment, provided herein is a solid form comprising a maleate salt of Compound 1, characterized by a DSC thermogram that matches the DSC thermogram presented in FIG. 16.

In one embodiment, Form A of a maleate salt of Compound 1 is prepared by slurrying free base of Compound 1 and maleic acid in acetonitrile (e.g., at room temperature for about 5 days).

In one embodiment, provided herein is a solid form comprising Form A of a maleate salt of Compound 1 and one or more forms of a free base of Compound 1 (e.g., amorphous form and crystalline forms). In one embodiment, provided herein is a solid form comprising Form A of a maleate salt of Compound 1 and amorphous maleate salt of Compound 1. In one embodiment, provided herein is a solid form comprising Form A of a maleate salt Compound 1 and one or more other crystalline forms of a maleate salt of Compound 1. In one embodiment, provided herein is a solid form comprising Form A of a maleate salt of Compound 1 and one or more forms (e.g., amorphous or crystalline) of a salt of Compound 1 provided herein.

(f) Besylate Salt of Compound 1

In some embodiments, provided herein is a besylate salt of Compound 1. It is contemplated that a besylate salt of Compound 1 can exist in a variety of solid forms. Such solid forms include crystalline solids, such as polymorphs, solvates and hydrates of crystalline besylate salt of Compound 1, as well as amorphous solids, or mixtures thereof.

In one embodiment, provided herein is a solid form comprising a besylate salt of Compound 1. In one embodiment, the solid form is a solvate of a besylate salt of Compound 1. In one embodiment, the solid form is a hydrate of a besylate salt of Compound 1. In one embodiment, the solid form is a non-solvated form of a besylate salt of Compound 1. In one embodiment, the solid form is a desolvated form of a besylate salt of Compound 1. In one embodiment, the solid form is an anhydrous form (anhydrate) of a besylate salt of Compound 1. In one embodiment, the solid form is a dehydrated form of a besylate salt of Compound 1.

In some embodiments, the molar ratio of Compound 1 to benzenesulfonic acid in the solid form ranges from about 1:1 to about 1:2. In one embodiment, the molar ratio is about 1:2 (i.e., bis-besylate salt). In another embodiment, the molar ratio is about 1:1 (i.e., mono-besylate salt).

(i) Form A of Besylate Salt of Compound 1

In certain embodiments, provided herein is Form A of a besylate salt of Compound 1.

In one embodiment, Form A is crystalline. In one embodiment, Form A is substantially crystalline. In one embodiment, Form A is moderately crystalline. In one embodiment, Form A is partially crystalline.

A representative XRPD pattern of Form A of a besylate salt of Compound 1 is provided in FIG. 17.

In one embodiment, provided herein is a solid form comprising a besylate salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, 27, or all of the peaks located at approximately the following positions: 6.9, 7.8, 8.5, 10.9, 11.3, 12.1, 13.2, 14.6, 15.1, 15.7, 16.2, 16.5, 16.9, 17.4, 17.9, 18.3, 19.3, 19.8, 20.5, 21.1, 21.9, 22.7, 23.8, 24.9, 25.1, 25.9, 26.7, and 27.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a besylate salt of Compound 1, characterized by an XRPD pattern comprising peaks at approximately 17.9, 18.3, and 23.8° 2θ. In one embodiment, the XRPD pattern further comprises peaks at approximately 15.7 and 16.2° 2θ. In one embodiment, the XRPD pattern further comprises peaks at approximately 8.5 and 16.5° 2θ. In one embodiment, the XRPD pattern comprises peaks at approximately 6.9, 8.5, 15.7, 16.2, 16.5, 16.9, 17.9, 18.3, 20.5, 21.1, 23.8, and 25.1° 2θ.

In one embodiment, provided herein is a solid form comprising a besylate salt of Compound 1, characterized by an XRPD pattern comprising peaks at approximately 6.9, 7.8, and 8.5° 2θ. In one embodiment, the XRPD pattern comprises peaks at approximately 6.9, 7.8, 8.5, 10.9, and 11.3° 2θ. In one embodiment, the XRPD pattern further comprises peaks at approximately 6.9, 7.8, 8.5, 10.9, 11.3, 12.1, and 13.2° 2θ. In one embodiment, the XRPD pattern comprises peaks at approximately 6.9, 7.8, 8.5, 10.9, 11.3, 12.1, 13.2, 14.6, and 15.1° 2θ.

In one embodiment, provided herein is a solid form comprising a besylate salt of Compound 1, characterized by an XRPD pattern that matches the XRPD pattern presented in FIG. 17.

In one embodiment, the XRPD patterns are obtained using Cu Kα radiation.

A representative thermal gravimetric analysis (TGA) thermogram of Form A of a besylate salt of Compound 1 is provided in FIG. 18. In one embodiment, provided herein is a solid form comprising a besylate salt of Compound 1, which exhibits a weight loss of about 0.25% upon heating from about 25° C. to about 150° C. In one embodiment, provided herein is a solid form comprising a besylate salt of Compound 1, characterized by a TGA thermogram that matches the TGA thermogram presented in FIG. 18.

A representative differential scanning calorimetry (DSC) thermogram of Form A of a besylate salt of Compound 1 is provided in FIG. 19. In one embodiment, provided herein is a solid form comprising a besylate salt of Compound 1, which exhibits, as characterized by DSC, a thermal event (endo) with an onset temperature of about 164° C. In one embodiment, the thermal event also has a peak temperature of about 175° C. In one embodiment, without being limited by any particular theory, the thermal event corresponds to melting. In one embodiment, provided herein is a solid form comprising a besylate salt of Compound 1, characterized by a DSC thermogram that matches the DSC thermogram presented in FIG. 19.

In one embodiment, Form A of a besylate salt of Compound 1 is prepared by adding benzenesulfonic acid to a solution of free base of Compound 1 in a solvent, resulting in precipitation of Form A of a besylate salt of Compound 1. In one embodiment, the solvent is acetone. In one embodiment, the solvent is MEK. In one embodiment, benzenesulfonic acid is added as an MEK solution.

In one embodiment, provided herein is a solid form comprising Form A of a besylate salt of Compound 1 and one or more forms of a free base of Compound 1 (e.g., amorphous form and crystalline forms). In one embodiment, provided herein is a solid form comprising Form A of a besylate salt of Compound 1 and amorphous besylate salt of Compound 1. In one embodiment, provided herein is a solid form comprising Form A of a besylate salt Compound 1 and one or more other crystalline forms of a besylate salt of Compound 1. In one embodiment, provided herein is a solid form comprising Form A of a besylate salt of Compound 1 and one or more forms (e.g., amorphous or crystalline) of a salt of Compound 1 provided herein.

5.3 Methods of Use

In one embodiment, provided herein is a method of treating a hematological malignancy, which comprises administering to a patient a therapeutically effective amount of a solid form or salt of Compound 1 provided herein.

In one embodiment, provided herein is a method of preventing a hematological malignancy, which comprises administering to a patient a therapeutically effective amount of a solid form or salt of Compound 1 provided herein.

In one embodiment, provided herein is a method of managing a hematological malignancy, which comprises administering to a patient a therapeutically effective amount of a solid form or salt of Compound 1 provided herein.

In one embodiment, the hematological malignancy is leukemia.

In one embodiment, the hematological malignancy is acute myeloid leukemia. In one embodiment, the acute myeloid leukemia is B-cell acute myeloid leukemia.

In one embodiment, the hematological malignancy is acute lymphocytic leukemia.

In one embodiment, the hematological malignancy is chronic lymphocytic leukemia/small lymphocytic lymphoma.

In one embodiment, the hematological malignancy is myeloma.

In one embodiment, the hematological malignancy is multiple myeloma. In one embodiment, the multiple myeloma is plasma cell leukemia (PCL).

In one embodiment, the hematological malignancy is lymphoma.

In one embodiment, the hematological malignancy is non-Hodgkin's lymphoma.

In one embodiment, the hematological malignancy is diffuse large B-cell lymphoma.

In one embodiment, the hematological malignancy is T-cell lymphoma. In one embodiment, the T-cell lymphoma is anaplastic large cell lymphoma (ALCL). In one embodiment, the T-cell lymphoma is Sezary Syndrome.

In one embodiment, the hematological malignancy is Burkitt lymphoma.

In one embodiment, the hematological malignancy is marginal zone lymphoma. In one embodiment, the marginal zone lymphoma is splenic marginal zone lymphoma (SMZL).

In one embodiment, the hematological malignancy is Hodgkin's lymphoma.

In one embodiment, the hematological malignancy is myelodysplastic syndromes.

In one embodiment, the hematological malignancy is newly diagnosed. In one embodiment, the hematological malignancy is relapsed or refractory.

In one embodiment, the AML is newly diagnosed AML. In one embodiment, the AML is relapsed or refractory AML. In one embodiment, the B-cell AML is newly diagnosed B-cell AML. In one embodiment, the B-cell AML is relapsed or refractory B-cell AML.

In one embodiment, the ALL is newly diagnosed ALL. In one embodiment, the ALL is relapsed or refractory ALL.

In one embodiment, the MM is newly diagnosed MM. In one embodiment, the MM is relapsed or refractory MM. In one embodiment, the PCL is newly diagnosed PCL. In one embodiment, the PCL is relapsed or refractory PCL.

In one embodiment, the HL is newly diagnosed HL. In one embodiment, the HL is relapsed or refractory HL.

In one embodiment, the NHL is newly diagnosed NHL. In one embodiment, the NHL is relapsed or refractory NHL.

In one embodiment, the TCL is newly diagnosed TCL. In one embodiment, the TCL is relapsed or refractory TCL. In one embodiment, the ALCL is newly diagnosed ALCL. In one embodiment, the ALCL is relapsed or refractory ALCL. In one embodiment, the Sezary Syndrome is newly diagnosed Sezary Syndrome. In one embodiment, the Sezary Syndrome is relapsed or refractory Sezary Syndrome.

In one embodiment, the BL is newly diagnosed BL. In one embodiment, the BL is relapsed or refractory BL.

In one embodiment, the MZL is newly diagnosed MZL. In one embodiment, the MZL is relapsed or refractory MZL. In one embodiment, the SMZL is newly diagnosed SMZL. In one embodiment, the SMZL is relapsed or refractory SMZL.

In one embodiment, the MDS is newly diagnosed MDS. In one embodiment, the MDS is relapsed or refractory MDS.

In one embodiment, provided herein are methods for achieving a complete response, partial response, or stable disease in a patient, comprising administering to a patient having a hematological malignancy provided herein a therapeutically effective amount of a solid form or salt of Compound 1 provided herein. In one embodiment, provided herein are methods for achieving an increase in overall survival, progression-free survival, event-free survival, time to progression, or disease-free survival in a patient, comprising administering to a patient having a hematological malignancy provided herein a therapeutically effective amount of a therapeutically effective amount of a solid form or salt of Compound 1 provided herein. In one embodiment, provided herein are methods for achieving an increase in overall survival in a patient, comprising administering to a patient having a hematological malignancy provided herein a therapeutically effective amount of a therapeutically effective amount of a solid form or salt of Compound 1 provided herein. In one embodiment, provided herein are methods for achieving an increase in progression-free survival in a patient, comprising administering to a patient having a hematological malignancy provided herein a therapeutically effective amount of a therapeutically effective amount of a solid form or salt of Compound 1 provided herein. In one embodiment, provided herein are methods for achieving an increase in event-free survival in a patient, comprising administering to a patient having a hematological malignancy provided herein a therapeutically effective amount of a therapeutically effective amount of a solid form or salt of Compound 1 provided herein. In one embodiment, provided herein are methods for achieving an increase in time to progression in a patient, comprising administering to a patient having a hematological malignancy provided herein a therapeutically effective amount of a therapeutically effective amount of a solid form or salt of Compound 1 provided herein. In one embodiment, provided herein are methods for achieving an increase in disease-free survival in a patient, comprising administering to a patient having a hematological malignancy provided herein a therapeutically effective amount of a therapeutically effective amount of a solid form or salt of Compound 1 provided herein. In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein is a method of treating AML, comprising administering to a subject in need thereof a therapeutically effective amount of a solid form or salt of Compound 1 provided herein. In one embodiment, the AML is B-cell AML.

In one embodiment, provided herein is a method of preventing AML, which comprises administering to a subject in need thereof a therapeutically effective amount of a solid form or salt of Compound 1 provided herein. In one embodiment, the AML is B-cell AML.

In one embodiment, provided herein is a method of managing AML, which comprises administering to a subject in need thereof a therapeutically effective amount of a solid form or salt of Compound 1 provided herein. In one embodiment, the AML is B-cell AML.

In one embodiment, provided herein is a method of treating ALL, comprising administering to a subject in need thereof a therapeutically effective amount of a solid form or salt of Compound 1 provided herein.

In one embodiment, provided herein is a method of preventing ALL, which comprises administering to a subject in need thereof a therapeutically effective amount of a solid form or salt of Compound 1 provided herein.

In one embodiment, provided herein is a method of managing ALL, which comprises administering to a subject in need thereof a therapeutically effective amount of a solid form or salt of Compound 1 provided herein.

In one embodiment, provided herein is a method of treating MM, comprising administering to a subject in need thereof a therapeutically effective amount of a solid form or salt of Compound 1 provided herein.

In one embodiment, provided herein is a method of preventing MM, which comprises administering to a subject in need thereof a therapeutically effective amount of a solid form or salt of Compound 1 provided herein.

In one embodiment, provided herein is a method of managing MM, which comprises administering to a subject in need thereof a therapeutically effective amount of a solid form or salt of Compound 1 provided herein.

In one embodiment, provided herein is a method of treating PCL, comprising administering to a subject in need thereof a therapeutically effective amount of a solid form or salt of Compound 1 provided herein.

In one embodiment, provided herein is a method of preventing PCL, which comprises administering to a subject in need thereof a therapeutically effective amount of a solid form or salt of Compound 1 provided herein.

In one embodiment, provided herein is a method of managing PCL, which comprises administering to a subject in need thereof a therapeutically effective amount of a solid form or salt of Compound 1 provided herein.

In one embodiment, provided herein is a method of treating TCL, comprising administering to a subject in need thereof a therapeutically effective amount of a solid form or salt of Compound 1 provided herein. In one embodiment, the TCL is ALCL. In one embodiment, the TCL is Sezary Syndrome.

In one embodiment, provided herein is a method of preventing TCL, which comprises administering to a subject in need thereof a therapeutically effective amount of a solid form or salt of Compound 1 provided herein. In one embodiment, the TCL is ALCL. In one embodiment, the TCL is Sezary Syndrome.

In one embodiment, provided herein is a method of managing TCL, which comprises administering to a subject in need thereof a therapeutically effective amount of a solid form or salt of Compound 1 provided herein. In one embodiment, the TCL is ALCL. In one embodiment, the TCL is Sezary Syndrome.

In one embodiment, provided herein is a method of treating BL, comprising administering to a subject in need thereof a therapeutically effective amount of a solid form or salt of Compound 1 provided herein.

In one embodiment, provided herein is a method of preventing BL, which comprises administering to a subject in need thereof a therapeutically effective amount of a solid form or salt of Compound 1 provided herein.

In one embodiment, provided herein is a method of managing BL, which comprises administering to a subject in need thereof a therapeutically effective amount of a solid form or salt of Compound 1 provided herein.

In one embodiment, provided herein is a method of treating HL, comprising administering to a subject in need thereof a therapeutically effective amount of a solid form or salt of Compound 1 provided herein.

In one embodiment, provided herein is a method of preventing HL, which comprises administering to a subject in need thereof a therapeutically effective amount of a solid form or salt of Compound 1 provided herein.

In one embodiment, provided herein is a method of managing HL, which comprises administering to a subject in need thereof a therapeutically effective amount of a solid form or salt of Compound 1 provided herein.

In one embodiment, provided herein is a method of treating MZL, comprising administering to a subject in need thereof a therapeutically effective amount of a solid form or salt of Compound 1 provided herein. In one embodiment, the MZL is SMZL.

In one embodiment, provided herein is a method of preventing MZL, which comprises administering to a subject in need thereof a therapeutically effective amount of a solid form or salt of Compound 1 provided herein. In one embodiment, the MZL is SMZL.

In one embodiment, provided herein is a method of managing MZL, which comprises administering to a subject in need thereof a therapeutically effective amount of a solid form or salt of Compound 1 provided herein. In one embodiment, the MZL is SMZL.

In one embodiment, provided herein is a method of treating MDS, comprising administering to a subject in need thereof a therapeutically effective amount of a solid form or salt of Compound 1 provided herein.

In one embodiment, provided herein is a method of preventing MDS, which comprises administering to a subject in need thereof a therapeutically effective amount of a solid form or salt of Compound 1 provided herein.

In one embodiment, provided herein is a method of managing MDS, which comprises administering to a subject in need thereof a therapeutically effective amount of a solid form or salt of Compound 1 provided herein.

In one embodiment, provided herein are methods of using a solid form or salt of Compound 1 provided herein, alone or in combination with rituximab, for treating, preventing or managing non-Hodgkin lymphoma (NHL).

In one embodiment, provided herein is a method of treating NHL, comprising administering to a subject in need thereof a therapeutically effective amount of a solid form or salt of Compound 1 provided herein.

In one embodiment, provided herein is a method of preventing NHL, which comprises administering to a subject in need thereof a therapeutically effective amount of a solid form or salt of Compound 1 provided herein.

In one embodiment, provided herein is a method of managing NHL, which comprises administering to a subject in need thereof a therapeutically effective amount of a solid form or salt of Compound 1 provided herein.

In one embodiment, the NHL is DLBCL. In one embodiment, the DLBCL is primary DLBCL. In one embodiment, the DLBCL is activated B-cell-like DLBCL (ABC-DLBCL). In one embodiment, the DLBCL is germinal center B-cell-like DLBCL (GCB-DLBCL). In one embodiment, the DLBCL is unclassified DLBCL. In one embodiment, the DLBCL is primary mediastinal B-cell type DLBCL (PMBL DLBCL). In one embodiment, the DLBCL is double-hit DLBCL (DHIT DLBCL), also referred to as cMyc/Bcl-2 mutant DLBCL. In one embodiment, the DLBCL is triple-hit DLBCL (THIT DLBCL) also referred to as cMyc/Bcl2/Bcl6 rearrangement DLBCL.

In one embodiment, the NHL is follicular lymphoma (FL).

In one embodiment, the NHL is mantle cell lymphoma (MCL).

In one embodiment, the NHL is primary central nervous system lymphoma (PCNSL).

In certain embodiments, the NHL is relapsed or refractory NHL. In one embodiment, the NHL is relapsed NHL. In one embodiment, the NHL is refractory NHL.

In certain embodiments, the NHL subject has radiological evidence of progression after achieving a complete response (CR). In certain embodiments, the NHL subject has achieved less than a CR to most recent systemic therapy containing regimen, and has radiological evidence of active disease or disease progression or recurrence in less than or equal to 12 months of prior stem cell transplantation (SCT).

In certain embodiments, the NHL subject has failed one or more lines of therapy and is not a candidate for other therapy. In certain embodiments, the subject has received at least one prior therapy and is not eligible for any therapy other than the methods of treatment described herein. In certain embodiments, the subject has relapsed after or progressed on standard anticancer therapy.

In certain embodiments, the subject has failed at least one prior therapy. In certain embodiments, the subject has failed at least two prior therapies.

In one embodiment, the NHL is relapsed or refractory DLBCL. In one embodiment, the DLBCL is relapsed DLBCL. In one embodiment, the DLBCL is refractory DLBCL. In one embodiment, the DLBCL is relapsed/refractory DLBCL. In one embodiment, the DLBCL is refractory to doxorubicin. In one embodiment, the DLBCL is resistant to doxorubicin. In one embodiment, the DLBCL is refractory to one or more of rituximab, cyclophosphamide, doxorubicin, vincristine, prednisone, etoposide, bendamustine, lenalidomide, gemcitabine, dexamethasone, ifosfamide, polatuxuab, or CAR-T.

In one embodiment, the DLBCL is treated with two or more prior lines of treatment.

In one embodiment, the DLBCL is transformed lymphoma. In another embodiment, the DLBCL is not otherwise specified (NOS) DLBCL.

In one embodiment, the NHL is relapsed or refractory FL. In one embodiment, the FL is relapsed FL. In one embodiment, the FL is refractory FL.

In one embodiment, the FL is treated with one or more prior lines of treatment. In one embodiment, the FL is treated with two or more prior lines of treatment.

In one embodiment, the NHL is relapsed or refractory MCL. In one embodiment, the MCL is relapsed MCL. In one embodiment, the MCL is refractory MCL.

In one embodiment, the MCL is treated with one or more prior lines of treatment. In one embodiment, the MCL is treated with two or more prior lines of treatment.

In one embodiment, the NHL is relapsed or refractory PCNSL. In one embodiment, the PCNSL is relapsed PCNSL. In one embodiment, the PCNSL is refractory PCNSL.

In certain embodiments, the NHL is newly diagnosed NHL. In certain embodiments, the NHL is newly diagnosed diffuse large B-cell lymphoma. In certain embodiments, the NHL is newly diagnosed follicular lymphoma. In certain embodiments, the NHL is newly diagnosed mantle cell lymphoma. In certain embodiments, the NHL is newly diagnosed primary central nervous system lymphoma.

In certain embodiments, the methods provided herein further comprise administering to the subject a therapeutically effective amount of rituximab.

In one embodiment, a first therapy provided herein (e.g., an agent such as a solid form or salt of Compound 1 provided herein) is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before) to the administration of a second therapy (e.g., rituximab) to the subject.

In one embodiment, a first therapy provided herein (e.g., an agent such as a solid form or salt of Compound 1 provided herein) is administered concomitantly with the administration of a second therapy (e.g., rituximab) to the subject.

In one embodiment, a first therapy provided herein (e.g., an agent such as a solid form or salt of Compound 1 provided herein) is administered subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., rituximab) to the subject.

In certain embodiments, rituximab is administered according to the locally approved label or Pharmacy manual for preparation, administration, and storage information. In certain embodiments, rituximab is administered intravenously. In certain embodiments, rituximab is administered subcutaneously. In certain embodiments, rituximab is administered via IV injection or IV infusion. In certain embodiments, rituximab is administered via IV infusion.

In certain embodiments, rituximab is administered at an amount according to the physician's decision. In certain embodiments, rituximab is administered once or twice daily. In certain embodiments, rituximab is administered in an amount of from about 50 to about 1000 $mg/m^2$, from about 100 to about 750 $mg/m^2$, from about 250 to about 500 $mg/m^2$, or from about 300 to about 400 $mg/m^2$. In certain embodiments, rituximab is administered in an amount of 375 $mg/m^2$ per day.

In one embodiment, provided herein is a method of treating DLBCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing DLBCL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing DLBCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of treating FL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing FL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing FL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of treating MCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing MCL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing MCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of treating PCNSL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing PCNSL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing PCNSL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of treating relapsed or refractory DLBCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing relapsed or refractory DLBCL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing relapsed or refractory DLBCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of treating relapsed or refractory FL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing relapsed or refractory FL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing relapsed or refractory FL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of treating relapsed or refractory MCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing relapsed or refractory MCL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing relapsed or refractory MCL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of treating relapsed or refractory PCNSL, which comprises administering to a subject in need thereof a therapeutically effective amount of a solid form or salt of Compound 1 provided herein. In one embodiment, the method further comprises administering to the subject a therapeutically effective amount of rituximab.

In one embodiment, provided herein is a method of preventing relapsed or refractory PCNSL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein is a method of managing relapsed or refractory PCNSL, which comprises administering to a subject in need thereof a therapeutically effective amount of a solid form or salt of Compound 1 provided herein. In one embodiment, the method further comprises administering to the subject a therapeutically effective amount of rituximab.

In another embodiment, provided herein are methods for achieving a complete response, partial response, or stable disease, as determined by the Lugano response criteria in a patient, comprising administering a therapeutically effective amount of a solid form or salt of Compound 1 provided herein, to patient having NHL. In another embodiment, provided herein are methods for achieving an increase in overall survival, progression-free survival, event-free survival, time to progression, or disease-free survival in a patient, comprising administering a therapeutically effective amount of a solid form or salt of Compound 1 provided herein, to patient having NHL. In another embodiment, provided herein are methods for achieving an increase in overall survival in a patient, comprising administering a therapeutically effective amount of a solid form or salt of Compound 1 provided herein, to patient having NHL. In another embodiment, provided herein are methods for achieving an increase in progression-free survival in a patient, comprising administering a therapeutically effective amount of a solid form or salt of Compound 1 provided herein, to patient having NHL. In another embodiment, provided herein are methods for achieving an increase in event-free survival in a patient, comprising administering a therapeutically effective amount of a solid form or salt of Compound 1 provided herein, to patient having NHL. In another embodiment, provided herein are methods for achieving an increase in time to progression in a patient, comprising administering a therapeutically effective amount of a solid form or salt of Compound 1 provided herein, to patient having NHL. In another embodiment, provided herein are methods for achieving an increase in disease-free survival in a patient, comprising administering a therapeutically effective amount of a solid form or salt of Compound 1 provided herein, to patient having NHL. In one embodiment, the methods further comprise administering to the subject a therapeutically effective amount of rituximab.

In one embodiment, provided herein are methods of using a solid form or salt of Compound 1 provided herein, alone or in combination with obinutuzumab, for treating, preventing or managing chronic lymphocytic leukemia/small lymphocytic lymphoma (CLL/SLL).

As used herein and unless otherwise indicated, "CLL/SLL" or "CLL and/or SLL" means CLL, or SLL, or CLL and SLL. In one embodiment, the methods provided herein are for treating, preventing or managing CLL. In one embodiment, the methods provided herein are for treating, preventing or managing SLL. In one embodiment, the methods provided herein are for treating, preventing or managing CLL and CLL.

In one embodiment, provided herein is a method of treating CLL/SLL, comprising administering to a subject in need thereof a therapeutically effective amount of a solid form or salt of Compound 1 provided herein.

In one embodiment, provided herein is a method of preventing CLL/SLL, which comprises administering to a subject in need thereof a therapeutically effective amount of a solid form or salt of Compound 1 provided herein.

In one embodiment, provided herein is a method of managing CLL/SLL, which comprises administering to a subject in need thereof a therapeutically effective amount of a solid form or salt of Compound 1 provided herein.

In one embodiment, the CLL/SLL subject has failed one or more lines of therapy. In one embodiment, the subject has failed at least one prior therapy. In one embodiment, the subject has failed at least two prior therapies. In one embodiment, the subject has been previously treated with a Bruton's tyrosine kinase (BTK) inhibitor. In one embodiment, the subject is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib.

In one embodiment, the CLL/SLL is newly diagnosed CLL/SLL. In one embodiment, the CLL/SLL is relapsed or refractory CLL/SLL (R/R CLL/SLL).

In one embodiment, the CLL is characterized by mutated IGHV (Immunoglobulin Heavy Chain Gene). In one embodiment, the CLL is characterized by non-mutated IGHV.

In one embodiment, the CLL is characterized by one or more mutations in TP53 (Tumor Protein 53). In one embodiment, the CLL is characterized by wild type TP53.

In one embodiment, the CLL is characterized by one or more cytogenetic abnormalities, e.g., del(13q), del(11q), del(17p), tri12, t(6;17), del(11q22.3), t(11;14), del(18q), and t(14;19). In one embodiment, the CLL is characterized by del(17p).

In one embodiment, the CLL is characterized by Richter's Transformation (also known as Richter's Syndrome).

In one embodiment, the methods provided herein further comprise administering to the subject a therapeutically effective amount of obinutuzumab.

In one embodiment, a first therapy (e.g., an agent such as a solid form or salt of Compound 1 provided herein) provided herein is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 120 hours, 144 hours, 1 week, 2 weeks, 3 weeks, 4 weeks, 5 weeks, 6 weeks, 8 weeks, or 12 weeks before) to the administration of a second therapy (e.g., obinutuzumab) to the subject.

In one embodiment, a first therapy (e.g., an agent such as a solid form or salt of Compound 1 provided herein) provided herein is administered concomitantly with the administration of a second therapy (e.g., obinutuzumab) to the subject.

In one embodiment, a first therapy (e.g., an agent such as a solid form or salt of Compound 1 provided herein) provided herein is administered subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 120 hours, 144 hours, 1 week, 2 weeks, 3 weeks, 4 weeks, 5 weeks, 6 weeks, 8 weeks, or 12 weeks after) the administration of a second therapy (e.g., obinutuzumab) to the subject.

In one embodiment, obinutuzumab is administered according to the locally approved label or Pharmacy manual for preparation, administration, and storage information. In one embodiment, obinutuzumab is administered intravenously. In one embodiment, obinutuzumab is administered subcutaneously. In one embodiment, obinutuzumab is administered via intravenous (IV) injection or IV infusion. In one embodiment, obinutuzumab is administered via IV injection. In one embodiment, obinutuzumab is administered via IV infusion.

In one embodiment, obinutuzumab is administered at an amount according to the physician's decision. In one embodiment, obinutuzumab is administered per day. In one embodiment, obinutuzumab is administered at a dose of from about 75 mg to about 1100 mg per day. In one embodiment, obinutuzumab is administered at a dose of from about 75 mg to about 125 mg per day, from about 800 mg to about 1000 mg per day, or from about 900 mg to about 1100 mg per day. In one embodiment, obinutuzumab is administered at a dose of about 100 mg per day. In one embodiment, obinutuzumab is administered at a dose of about 900 mg per day. In one embodiment, obinutuzumab is administered at a dose of about 1000 mg per day. In one embodiment, obinutuzumab is administered at a dose of about 100 mg on day 1 of a first 28-day cycle, about 900 mg on day 2 of the first 28-day cycle, and about 1000 mg on each of days 8 and 15 of the first 28-day cycle and day 1 of a second to a sixth 28-day cycles. In one embodiment, obinutuzumab is administered at a dose of about 1000 mg combined on day 1 and 2 of the first 28-day cycle, and about 1000 mg on each of days 8 and 15 of the first 28-day cycle and day 1 of a second to a sixth 28-day cycles. Obinutuzumab can be administered beyond six cycles. In one embodiment, obinutuzumab is administered in a first 28-day cycle as described herein, and is administered at about 1000 mg on day 1 of a second to a $12^{th}$ 28-day cycles. In one embodiment, obinutuzumab is administered in a first 28-day cycle as described herein, and is administered at about 1000 mg on day 1 of a second to a $24^{th}$ 28-day cycles. In one embodiment, obinutuzumab is administered in a first 28-day cycle as described herein, and is administered at about 1000 mg on day 1 of subsequent 28-day cycles until progression of disease.

In one embodiment, provided herein is a method of treating newly diagnosed CLL/SLL, which comprises administering to a subject in need thereof a therapeutically effective amount of a solid form or salt of Compound 1 provided herein. In one embodiment, the method further comprises administering to the subject a therapeutically effective amount of obinutuzumab.

In one embodiment, provided herein is a method of preventing newly diagnosed CLL/SLL, which comprises administering to a subject in need thereof a therapeutically effective amount of a solid form or salt of Compound 1 provided herein. In one embodiment, the method further comprises administering to the subject a therapeutically effective amount of obinutuzumab.

In another embodiment, provided herein is a method of managing newly diagnosed CLL/SLL, which comprises administering to a subject in need thereof a therapeutically effective amount of a solid form or salt of Compound 1 provided herein. In one embodiment, the method further comprises administering to the subject a therapeutically effective amount of obinutuzumab.

In one embodiment, provided herein is a method of treating relapsed or refractory CLL/SLL, which comprises administering to a subject in need thereof a therapeutically effective amount of a solid form or salt of Compound 1 provided herein. In one embodiment, the method further comprises administering to the subject a therapeutically effective amount of obinutuzumab.

In one embodiment, provided herein is a method of preventing relapsed or refractory CLL/SLL, which comprises administering to a subject in need thereof a therapeutically effective amount of a solid form or salt of Compound 1 provided herein. In one embodiment, the method further comprises administering to the subject a therapeutically effective amount of obinutuzumab.

In another embodiment, provided herein is a method of managing relapsed or refractory CLL/SLL, which comprises administering to a subject in need thereof a therapeutically effective amount of a solid form or salt of Compound 1 provided herein. In one embodiment, the method further comprises administering to the subject a therapeutically effective amount of obinutuzumab.

In another embodiment, provided herein are methods for achieving a complete response, partial response, or stable disease, as determined by the International Workshop on Chronic Lymphocytic Leukemia criteria in a patient, comprising administering a therapeutically effective amount of a solid form or salt of Compound 1 provided herein to patient having CLL/SLL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a solid form or salt of Compound 1 provided herein to patient having CLL/SLL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a solid form or salt of Compound 1 provided herein to patient having CLL/SLL. In another embodiment, provided herein are methods for achieving an increase in overall survival in a patient, comprising administering a therapeutically effective amount of a solid form or salt of Compound 1 provided herein to patient having CLL/SLL. In another embodiment, provided herein are methods for achieving an increase in progression-free survival in a patient, comprising administering a therapeutically effective amount of a solid form or salt of Compound 1 provided herein to patient having CLL/SLL. In another embodiment, provided herein are methods for achieving an increase in event-free survival in a patient, comprising administering a therapeutically effective amount of a solid form or salt of Compound 1 provided herein to patient having CLL/SLL. In another embodiment, provided herein are methods for achieving an increase in time to progression in a patient, comprising administering a therapeutically effective amount of a solid form or salt of Compound 1 provided herein to patient having CLL/SLL. In another embodiment, provided herein are methods for achieving an increase in disease-free survival in a patient, comprising administering a therapeutically effective amount of a solid form or salt of Compound 1 provided herein to patient having CLL/SLL. In one embodiment, the methods further comprise administering to the subject a therapeutically effective amount of obinutuzumab.

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old.

Also provided herein is a solid form or salt of Compound 1 for use in a method of treating a disease provided herein, wherein the method comprises administering to a patient a therapeutically effective amount of the solid form or salt of Compound 1. Also provided herein is a pharmaceutical composition comprising the solid form or salt of Compound 1 for use in a method of treating a disease provided herein.

5.4 Pharmaceutical Compositions and Routes of Administration

The solid forms or salts of Compound 1 provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as a diluent (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrant (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), water, and base wax (e.g., cocoa butter, white petrolatum or polyethylene glycol). The effective amount of the compounds in the pharmaceutical composition may be at a level that will exercise the desired effect for both oral and parenteral administration.

A solid form or salt of Compound 1 provided herein can be administered orally. In one embodiment, when administered orally, a solid form or salt of Compound 1 provided herein is administered with a meal and water. In another embodiment, the solid form or salt of Compound 1 provided herein is dispersed in water or juice (e.g., apple juice or orange juice) and administered orally as a solution or a suspension.

A solid form or salt of Compound 1 provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a solid form or salt of Compound 1 provided herein without an additional excipient. In another embodiment, provided herein are compositions comprising an effective amount of a solid form or salt of Compound 1 provided herein and a pharmaceutically acceptable excipient, wherein a pharmaceutically acceptable excipient can comprise a diluent, binder, disintegrant, glidant, lubricant, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry. Capsules can be prepared by mixing a solid form or salt of Compound 1 provided herein with a suitable excipient and filling the proper amount of the mixture in capsules. The usual excipients include, but are not limited to, inert powdered substances such as starch of many different kinds, powdered cellulose, especially crystalline and microcrystalline cellulose, sugars such as fructose, mannitol and sucrose, grain flours and similar edible powders. Capsules fill can also be prepared by wet granulation or by dry granulation.

A lubricant might be necessary in a capsule formulation to prevent the powder from sticking to the pin. The lubricant can be chosen from such slippery solids as talc, magnesium and calcium stearate, sodium stearyl fumarate, stearic acid and hydrogenated vegetable oils. Disintegrants are substances that swell when wetted to break up the capsule slug and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate.

Tablets can be prepared by direct compression, by wet granulation, or by dry granulation. Their formulations usually incorporate diluents, binders, lubricants and disintegrants as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, sodium stearyl fumarate, stearic acid and hydrogenated vegetable oils. Tablet disintegrants are substances that swell when wetted to break up the tablet and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a solid form or salt of Compound 1 provided herein as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the solid form or salt of Compound 1 provided herein can be delayed or prolonged by proper formulation. For example, a slowly soluble pellet of the solid form or salt of Compound 1 provided herein can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the solid form or salt of Compound 1 provided herein in oily or emulsified vehicles that allow it to disperse slowly in the serum.

Depending on the state of the disease to be treated and the subject's condition, a solid form or salt of Compound 1 provided herein, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A solid form or salt of Compound 1 provided herein, may be formulated, alone or together, in suitable dosage unit with pharmaceutically acceptable excipients, carriers, adjuvants and vehicles, appropriate for each route of administration.

In one embodiment, a solid form or salt of Compound 1 provided herein is administered orally. In another embodiment, a solid form or salt of Compound 1 provided herein is administered parenterally. In yet another embodiment, a solid form or salt of Compound 1 provided herein is administered intravenously.

A solid form or salt of Compound 1 provided herein can be delivered as a single dose such as, e.g., a single bolus injection, or oral capsules, tablets or pills; or over time, such as, e.g., continuous infusion over time or divided bolus doses over time. The solid form or salt of Compound 1 provided herein can be administered repeatedly if necessary, for example, until the patient experiences stable disease or regression, or until the patient experiences disease progression or unacceptable toxicity.

A solid form or salt of Compound 1 provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as a solid form or salt of Compound 1 provided herein, is administered once or more than once each day, for example, for a period of time. The term "continuous" is intended to mean that a therapeutic compound, such as a solid form or salt of Compound 1 provided herein, is administered daily for an uninterrupted period of at least 7 days to 52 weeks. The term "intermittent" or "intermittently" as used herein is intended to mean stopping and starting at either regular or irregular intervals. For example, intermittent administration of a solid form or salt of Compound 1 provided herein is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as a solid form or salt of Compound 1 provided herein, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a solid form or salt of Compound 1 provided herein is administered once a day. In another embodiment, a solid form or salt of Compound 1 provided herein is administered twice a day. In yet another embodiment, a solid form or salt of Compound 1 provided herein is administered three times a day. In still another embodiment, a solid form or salt of Compound 1 provided herein is administered four times a day.

In certain embodiments, the methods provided herein include an administration of a therapeutically effective amount of a solid form or salt of Compound 1 provided herein in one or more 7-day treatment cycles. In another embodiment, the methods provided herein include an administration of a therapeutically effective amount of a solid form or salt of Compound 1 provided herein on days 1 to 5 of a 7-day cycle. In another embodiment, the methods provided herein include an administration of a therapeutically effective amount of a solid form or salt of Compound 1 provided herein on days 1 to 3 of a 7-day cycle.

In certain embodiments, the methods provided herein include an administration of a therapeutically effective amount of a solid form or salt of Compound 1 provided herein in one or more 14-day treatment cycles. In another embodiment, the methods provided herein include an administration of a therapeutically effective amount of a solid form or salt of Compound 1 provided herein on days 1 to 7 of a 14-day cycle. In another embodiment, the methods provided herein include an administration of a therapeutically effective amount of a solid form or salt of Compound 1 provided herein on days 1 to 10 of a 14-day cycle.

In certain embodiments, the methods provided herein include an administration of a therapeutically effective amount of a solid form or salt of Compound 1 provided herein in one or more 28-day treatment cycles. In another embodiment, the methods provided herein include an administration of a therapeutically effective amount of a solid form or salt of Compound 1 provided herein on days 1 to 21 of a 28-day cycle. In another embodiment, the methods provided herein include an administration of a therapeutically effective amount of a solid form or salt of Compound 1 provided herein on days 1 to 5, days 8 to 12, days 15 to 19, and days 22 to 26 of a 28-day cycle. In another embodiment, the methods provided herein include an administration of a therapeutically effective amount of a solid form or salt of Compound 1 provided herein on days 1 to 10 and days 15 to 24 of a 28-day cycle.

In one embodiment, a solid form or salt of Compound 1 provided herein is administered once daily for 5 days followed by 2 days of rest. In one embodiment, a solid form or salt of Compound 1 provided herein is administered once daily for 3 days followed by 4 days of rest. In one embodiment, a solid form or salt of Compound 1 provided herein is administered once daily for 7 days followed by 7 days of rest. In one embodiment, a solid form or salt of Compound 1 provided herein is administered once daily for 10 days followed by 4 days of rest. In one embodiment, a solid form or salt of Compound 1 provided herein is administered once daily for 21 days followed by 7 days of rest.

In certain embodiments, the treatment includes an administration of a therapeutically effective amount of rituximab in one or more treatment cycles. In one embodiment, rituximab is administered once every 7 days. In one embodiment, rituximab is administered once every 4 weeks. In one embodiment, rituximab is administered once every 8 weeks. In one embodiment, rituximab is administered at days 1, 8, 15, and 22 of the first 28-day cycle, administered at day 1 of the second to the sixth 28-day cycles, and then administered once every 8 weeks.

In one embodiment, the treatment includes an administration of a therapeutically effective amount of obinutuzumab in one or more treatment cycles. In one embodiment, obinutuzumab is administered twice every 7 days. In one embodiment, obinutuzumab is administered once every week. In one embodiment, obinutuzumab is administered once every 4 weeks. In one embodiment, obinutuzumab is administered on days 1, 2, 8, and 15 of the first 28-day cycle, and administered on day 1 of the second to the sixth 28-day cycles. In one embodiment, obinutuzumab is administered on day 1 of a second to a $12^{th}$ 28-day cycles. In one embodiment, obinutuzumab is administered on day 1 of a second to a $24^{th}$ 28-day cycles. In one embodiment, obinutuzumab is administered on day 1 of subsequent 28-day cycles until progression of disease.

In one embodiment, obinutuzumab is administered at a dose of about 100 mg on day 1 of the first 28-day cycle, about 900 mg on day 2 of the first 28-day cycle, and about 1000 mg on each of days 8 and 15 of the first 28-day cycle. In one embodiment, obinutuzumab is administered at a dose of about 1000 mg combined on day 1 and 2 of the first 28-day cycle, and about 1000 mg on each of days 8 and 15 of the first 28-day cycle. In one embodiment, obinutuzumab is administered at a dose of about 1000 mg on day 1 of the second to the sixth 28-day cycles. In one embodiment, obinutuzumab is administered at about 1000 mg on day 1 of a second to a $12^{th}$ 28-day cycles. In one embodiment, obinutuzumab is administered at about 1000 mg on day 1 of a second to a $24^{th}$ 28-day cycles. In one embodiment, obinutuzumab is administered at about 1000 mg on day 1 of subsequent 28-day cycles until progression of disease.

Any treatment cycle described herein can be repeated for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In some embodiments, a therapeutically effective amount of a solid form or salt of Compound 1 provided herein and/or rituximab is administered for 1 to 13 cycles of 28 days (e.g., about 1 year). In some embodiments, a therapeutically effective amount of a solid form or salt of Compound 1 provided herein and/or rituximab is administered for 1 to 24 cycles of 28 days (e.g., about 2 years). In some embodiments, a therapeutically effective amount of a solid form or salt of Compound 1 provided herein and/or obinutuzumab is administered for 1 to 13 cycles of 28 days (e.g., about 1 year). In some embodiments, a therapeutically effective amount of a solid form or salt of Compound 1 provided herein and/or obinutuzumab is administered for 1 to 24 cycles of 28 days (e.g., about 2 years). In certain instances, the cycling therapy is not limited to the number of cycles, and the therapy is continued until disease progression. Cycles can in certain instances include varying the duration of administration periods and/or rest periods described herein.

6. EXAMPLES

Certain embodiments of the invention are illustrated by the following non-limiting examples.

Abbreviations Used

| | |
|---|---|
| ACN | Acetonitrile |
| API | Active pharmaceutical ingredient |
| DCM | Dichloromethane |
| DIEA | N,N-Diisopropylethylamine |
| DMAc | Dimethylacetamide |
| DMSO | Dimethylsulfoxide |
| ESI | Electrospray ionization |
| $Et_2O$ | Diethyl ether |
| EtOAc | Ethyl acetate |
| EtOH | Ethanol |
| HDPE | High-density polyethylene |
| LCMS | Liquid chromatography mass spectrometry |
| LDPE | Low-density polyethylene |
| MEK | Methyl ethyl ketone |
| MeOH | Methanol |
| 2-MeTHF | 2-Methyl tetrahydrofuran |
| MS | Mass spectrometry |
| MTBE | Methyl tert-butyl ether |
| NMP | N-Methylpyrrolidone |
| NMR | Nuclear magnetic resonance |
| 2-PrOH | 2-Propanol |
| RH | Relative humidity |
| THF | Tetrahydrofuran |

6.1 Synthesis of (S)-2-(2,6-dioxopiperidin-3-yl)-4-((2-fluoro-4-((3-morpholinoazetidin-1-yl)methyl)benzyl)amino)isoindoline-1,3-dione (Compound 1)

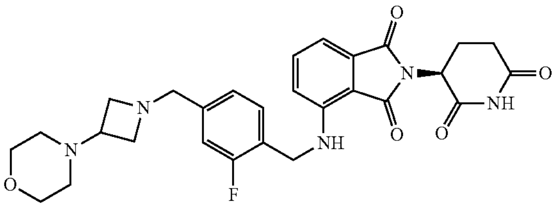 [SMILES: O=C1CC[C@H](N2C(=O)c3cccc(NCc4ccc(CN5CC(N6CCOCC6)C5)cc4F)c3C2=O)C(=O)N1]

(S)-2-(2,6-Dioxopiperidin-3-yl)-4-((2-fluoro-4-(hydroxymethyl)benzyl)amino)isoindoline-1,3-dione: A suspension of (S)-4-amino-2-(2,6-dioxopiperidin-3-yl)isoindoline-1,3-dione (5.00 g, 18.3 mmol) and 2-fluoro-4-(hydroxymethyl)benzaldehyde (2.82 g, 18.30 mmol) in 2:1 dioxane-MeOH (75 mL) was cooled to 0° C. and $B_{10}H_{14}$ (4.92 g, 40.3 mmol) was added in small portions over 5 minutes. The reaction flask was fitted with a septum and needle vent (pressure) and vigorously stirred for 10 minutes. The mixture was allowed to reach ambient temperature and stirred for 3 hours. The mixture was concentrated and the residue purified by silica gel chromatography (0-10% MeOH-DCM) to provide (S)-2-(2,6-dioxopiperidin-3-yl)-4-((2-fluoro-4-(hydroxymethyl)benzyl)amino)isoindoline-1,3-dione as a yellow solid (4.23 g, 56%). LCMS (ESI) m/z 411.8 $[M+H]^+$.

(S)-4-((4-(Chloromethyl)-2-fluorobenzyl)amino)-2-(2,6-dioxopiperidin-3-yl)isoindoline-1,3-dione: A solution of (S)-2-(2,6-dioxopiperidin-3-yl)-4-((2-fluoro-4-(hydroxymethyl)benzyl)amino)isoindoline-1,3-dione (0.727 g, 1.77 mmol) in dry NMP (6 mL) was cooled to 0° C. and methane sulfonyl chloride (0.275 mL, 3.35 mmol) and DIEA (0.617 mL, 3.53 mmol) were added sequentially. The reaction mixture was allowed to reach ambient temperature and was stirred for 18 hours. The reaction mixture was slowly added to $H_2O$ (60 mL) cooled to 0° C. with vigorous mixing. The resulting suspension was filtered and the collected solid was washed with $H_2O$ and $Et_2O$. The solid was dissolved in EtOAc and the solution dried with $MgSO_4$, filtered and concentrated to provide (S)-4-((4-(chloromethyl)-2-fluorobenzyl)amino)-2-(2,6-dioxopiperidin-3-yl)isoindoline-1,3-dione as a yellow solid (0.600 g, 79%). LCMS (ESI) m/z 430.0 $[M+H]^+$.

(S)-2-(2,6-Dioxopiperidin-3-yl)-4-((2-fluoro-4-((3-morpholinoazetidin-1-yl)methyl)benzyl)amino)isoindoline-1,3-dione: To a solution of (S)-4-((4-(chloromethyl)-2-fluorobenzyl)amino)-2-(2,6-dioxopiperidin-3-yl)isoindoline-1,3-dione (300 mg, 0.698 mmol) in dry DMSO (1.0 mL) was added 4-(azetidin-3-yl)morpholine hydrochloride (125 mg, 0.698 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-2-(2,6-dioxopiperidin-3-yl)-4-((2-fluoro-4-((3-morpholinoazetidin-1-yl)methyl)benzyl)amino)isoindoline-1,3-dione (89 mg, 24%, 97% ee). LCMS (ESI) m/z 536.2 $[M+H]^+$.

6.2 Cell-Based Assays Using Compound 1

The following are examples of cell-based assays that can be used to determine the anti-proliferative activity and apoptotic effect of Compound 1 using exemplary non-Hodgkin lymphoma (NHL) cell lines.

Cell Proliferation and Viability Assay Using SU-DHL-4 Cell Line: The following exemplary assay uses a DLBCL cell line, for example, the SU-DHL-4 cell line (Deutsche Sammlung von Mikroorganismen and Zellkulturen GmbH [DSMZ]: catalogue number ACC-495) at 120 hours post-treatment. The seeding density for SU-DHL-4 can be optimized to ensure assay linearity in 1536-well plates.

Increasing concentrations (0.5 nM to 10 μM) of Compound 1 were each spotted in a 20-point dilution fashion (unevenly spaced data points) via an acoustic dispenser (EDC ATS-100) into an empty 1536-well plate. The DMSO concentration was kept constant for a final assay concentration of 0.1% DMSO. Prior to testing, SU-DHL-4 cells were grown in RPMI-1640 (Roswell Park Memorial Institute-1640) medium with 10% FBS (fetal bovine serum: HyClone) and expanded in culture flasks to provide sufficient amounts of starting material. Cells were then diluted to 500 cells per well in a 5 μL volume, and added directly to the compound-spotted 1536-well plates. Cells were allowed to grow for 120 hours in 5% $CO_2$ at 37° C. At the time when exposure of cells to compound began ($t_0$), initial viable cell number was assessed via Cell Titer-Gb® Luminescent Cell Viability Assay at a 1 vol:2 vol ratio according to manufacturer's instructions (Promega Corporation, Madison, WI) by quantifying the level of luminescence generated by adenosine-5'-triphosphate (ATP) present in viable cells. After 120 hours, cell viability of the treated cells was assessed via Cell Titer-Gb® and read for luminescence. All growth inhibition curves were processed and evaluated using Activity Base (IDBS, Alameda, CA). Cell viability $IC_{50}$ values were calculated using a four parameter logistic model (sigmoidal dose-response model):

$$y=(A+((B-A)/(1+((C/x)^D))))$$

wherein:

$A=Y_{Min}$ $B=Y_{Max}$ $C=EC_{50}$

D=Hill slope $IC_{50}$=the concentration of the compound when Y=50% of DMSO control Y=cell viability measured as luminescence unit, and x=concentration of compound.

Compound 1 was found to have activity in SU-DHL-4 cell proliferation assay with an $IC_{50}$<0.2 μM.

Cell Proliferation and Viability Assay Using Hematological Cell Lines: The following exemplary anti-proliferative assay uses exemplary hematological cell lines in the following. The in vitro growth inhibitory activity of Compound 1 described herein was evaluated using a 384-well flow cytometry assay.

TABLE 6

Hematological Cell Lines

| Cell Line | Tumor type | Tumor subtype | Culture conditions |
|---|---|---|---|
| ULA | DLBCL | not specified | RPMI + 10% FBS, 1X NEAA, |
| SU-DHL-5 | DLBCL | not specified | 2 mM L-glutamine |
| OCI-LY18 | DLBCL | not specified | |
| TMD8 | DLBCL | ABC | |
| SU-DHL-2 | DLBCL | ABC | |
| Farage | DLBCL | PMBL | |
| SU-DHL-10 | DLBCL | GCB | |
| NU-DHL-1 | DLBCL | GCB | |

TABLE 6-continued

| Hematological Cell Lines | | | |
|---|---|---|---|
| Cell Line | Tumor type | Tumor subtype | Culture conditions |
| VAL | DLBCL | not specified | |
| WILL-2 | DLBCL | not specified | |
| SU-DHL-6 | DLBCL | GCB | |
| KARPAS-422 | DLBCL | GCB | |
| NU-DUL-1 | DLBCL | ABC | |
| KARPAS-1106P | DLBCL | PMBL | |
| OCI-LY1 | DLBCL | GCB | |
| SU-DHL-1 | DLBCL | not specified | |
| WSU-DLCL2 | DLBCL | GCB | |
| STR428 | DLBCL | not specified | |
| U-2946 | DLBCL | not specified | |
| U-2940 | DLBCL | PMBL | |
| OCI-LY-19 | DLBCL | GCB | |
| CARNAVAL | DLBCL | not specified | |
| Toledo | DLBCL | GCB | |
| RC-K8 | DLBCL | ABC | |
| SU-DHL-8 | DLBCL | GCB | |
| OCI-LY10 | DLBCL | ABC | |
| SU-DHL-16 | DLBCL | GCB | |
| U-2932 | DLBCL | ABC | |
| WILL-1 | DLBCL | not specified | |
| SU-DHL-4 | DLBCL | GCB | |
| Pfeiffer | DLBCL | GCB | |
| U-2904 | DLBCL | not specified | |
| WSU-DLCL | DLBCL | GCB | |
| HT | DLBCL | GCB | |
| RIVA | DLBCL | ABC | |
| ROS-50 | DLBCL | not specified | |
| GCBDB | DLBCL | GCB | |
| OCI-LY-7 | DLBCL | GCB | IMDM + 20% Human Plasma |
| OCI-LY-3 | DLBCL | ABC | |
| DOHH2 | FL | not specified | RPMI + 10% FBS, 1X NEAA, |
| RL | FL | not specified | 2 mM L-glutamine |
| Mino | MCL | not specified | RPMI1640 + 15% FBS + 2 mML-glutamine + 10 mM Hepes + 1 mM sodium pyruvate + 4.5 g/L glucose |
| Rec-1 | MCL | not specified | RPMI + 10% FBS + 2 mML-glutamine |
| EHEB | CLL | not specified | RPMI + 10% FBS, 1X NEAA, |
| WA-C3-CD5+ | CLL | not specified | 2 mM L-glutamine |
| WA-OSEL | CLL | not specified | |
| PGA1 | CLL | not specified | |
| HG3 | CLL | not specified | |
| I83-E95 | CLL | not specified | RPMI + 20% FBS, 1X NEAA, |
| CII | CLL | not specified | 2 mM L-glutamine |
| CI | CLL | not specified | |
| Mec2 | CLL | not specified | IMDM + 10% FBS |
| Mec1 | CLL | not specified | |
| SVSL/VL51 | MZL | SMZL | RPMI + 10% FBS, 1X NEAA, 2 mM L-glutamine |
| Daudi | BL | not specified | RPMI + 10% FBS + 2 mM L-glutamine |
| BL-41 | BL | not specified | RPMI1640 + 10% FBS + 1 mM sodium pyruvate + 50 uM 2-mercaptoethanol |
| MDS-L | MDS | not specified | RPMI + 10% FBS + 50 μM 2-mercaptoethanol + 50 U/mL + rhIL-3 |
| HNT-34 | AML | not specified | RPMI + 10% FBS + 2 mM L-glutamine |
| GDM-1 | AML | not specified | RPMI + 10% FBS |
| NCI-H929 | MM | not specified | RPMI + 10% FBS + GlutaMax |
| OPM-2 | MM | not specified | RPMI + 10% FBS |
| HuT-102 | TCL | not specified | |
| Karpas-299 | TCL | not specified | |
| JJN-3 | MM | PCL | |
| L-363 | MM | PCL | |
| SK-MM-1 | MM | PCL | 40% IMDM + 40% DMEM + 20% FBS |

TABLE 6-continued

| Hematological Cell Lines | | | |
|---|---|---|---|
| Cell Line | Tumor type | Tumor subtype | Culture conditions |
| Karpas-231 | ALL | not specified | RPMI + 10% FBS |
| KOPN-8 | ALL | not specified | |
| L-428 | HL | not specified | |
| L-591 | HL | not specified | RPMI + 20% FBS |

ABC = activated B-cell like;
FBS = fetal bovine serum;
GCB = germinal center B-cell;
IMDM = Iscove's Modified Dulbecco's medium;
NEAA = non-essential amino acid;
RPMI = RPMI1640.

The cell lines were plated in 384-well flat bottom plates and assessed with increasing concentrations of compound ranging from 0.00015 to 10 μM or dimethyl sulfoxide (DMSO) control. The final concentration of DMSO was 0.1% (v/v). Following the addition of Compound 1 or DMSO and incubation for 120 hours, cell number and cell death were analyzed by flow cytometry (Attune®, Thermo Fisher) using Annexin V and the live-cell impermeant DNA dye, DRAQ7. Phosphatidylserine translocates from the inner layer to the outer layer of the cell membrane early in apoptosis and Annexin V binds to the exposed phosphatidylserine found on the surface of an apoptotic cell. The vital dye DRAQ7 is excluded by intact live cells and only stains cells that have died as a result of apoptosis or necrosis.

Flow cytometry data analysis was then performed using the Flow Jo_v10 software to determine the number of viable cells (Annexin V and DRAQ7 double negative staining cells) and percentage of apoptotic cells (Annexin V positive cells) for each condition. The live cell count for every concentration was normalized to the DMSO control (considered as 100%) to calculate the percentage of viable cells remaining after treatment and graphed using GraphPad Prism 7.03. The $IC_{50}$ (50% inhibitory concentration) and $E_{max}$ (maximum efficacy achieved) values were then calculated by performing nonlinear regression curve fitting using log(inhibitor) vs. normalized response-variable slope analysis on GraphPad Prism 7.03. Area under the curve (AUC) was calculated by performing area under curve analysis on GraphPad Prism 7.03. Similarly, for apoptosis analysis, the percentage of apoptosis combining both "early" (Annexin V positive and DRAQ7 negative) and "late" apoptosis (Annexin V and DRAQ7 positive) cell gates relative to DMSO was graphed using GraphPad Prism 7.03. The AUC, $EC_{50}$ (concentration of compound that produces half-maximal apoptosis response) and $Y_{max}$ (maximal percentage of apoptosis achieved) values from apoptosis curves were calculated by performing area under curve analysis and nonlinear regression curve fitting using log(agonist) vs. normalized response—Variable slope analysis on GraphPad Prism 7.03.

Dose-response proliferation curves for the panel of hematological cell lines and non-linear curve-fit regression were used to determine $IC_{50}$, AUC, and $E_{max}$ for % viable cells ($E_{max}$ for viability varies between 100 at low doses and 0 at high doses, which corresponds to inhibition of all viable cells), and dose-response apoptosis curves were used to determine the $EC_{50}$, AUC, and $Y_{max}$ for % apoptosis ($Y_{max}$ for apoptosis varies from 0 at low doses and 100 at higher doses which corresponds to death of all cells). Tumor cells were exposed to serial dilutions (0.00015 to 10 μM) of Compound 1 or dimethyl sulfoxide (DMSO) control for 5 days. Viability and apoptosis for all cell lines was determined by Annexin V/7-aminoactinomycin D (7-AAD) flow cytometry. Compound 1 was found to have antiproliferative activity and/or apoptotic effects in almost all hematological cell lines tested, as shown in the following table.

TABLE 7

| Antiproliferative Activity and Apoptotic Effect of Compound 1 in Hematological Cell Lines | | | | | | |
|---|---|---|---|---|---|---|
| | % Viable Cells | | | Apoptosis | | |
| Cell Line | AUC | $IC_{50}$ | $E_{max}$ | AUC | $EC_{50}$ | $Y_{max}$ |
| ULA | 0.5518 | 0.00099 | 0.02523 | 995.3 | 0.00179 | 99.76 |
| SU-DHL-5 | 1.873 | 0.002389 | 0.1398 | 934.1 | 0.003603 | 95.23 |
| OCI-LY18 | 1.965 | 0.0009441 | 0.05973 | 965.2 | 0.002976 | 97.44 |
| TMD8 | 4.187 | 0.002459 | 0.245 | 963.3 | 0.006172 | 97.2 |
| SU-DHL-2 | 5.586 | 0.001263 | 0.2145 | 928.4 | 0.006242 | 95.98 |
| Farage | 10.16 | 0.002375 | 0.7936 | 728.7 | 0.03017 | 84.17 |
| SU-DHL-10 | 10.36 | 0.006101 | 0.6716 | 903 | 0.03942 | 92.27 |
| NU-DHL-1 | 12.37 | 0.001073 | 0.4919 | 981.8 | 0.001267 | 99.17 |
| VAL | 14.62 | 0.0005703 | 0.9632 | 936.7 | 0.0006045 | 95.68 |
| WILL-2 | 17.1 | 0.002359 | 0.03115 | 916.9 | 0.08971 | 99.43 |
| SU-DHL-6 | 19.94 | 0.03248 | 0.2469 | 920.7 | 0.1045 | 95.92 |
| KARPAS-422 | 19.97 | 0.01313 | 0.8721 | 911.9 | 0.0461 | 93.99 |
| NU-DUL-1 | 22.12 | 0.03527 | 0.0228 | 962.8 | 0.06304 | 99.84 |
| KARPAS-1106P | 22.22 | 0.01748 | 0.1698 | 885.2 | 0.09182 | 97.08 |
| OCI-LY1 | 22.77 | 0.006002 | 1.037 | 852.3 | 0.03338 | 90.09 |
| SU-DHL-1 | 31.14 | 0.0005495 | 2.485 | 690.1 | 0.001105 | 73.83 |
| WSU-DLCL2 | 36.7 | 0.01691 | 1.387 | 858.9 | 0.08473 | 92.1 |
| STR428 | 43.48 | 0.09471 | 1.227 | 905.9 | 0.1016 | 95.17 |
| U-2946 | 45.47 | 0.004604 | 0.4821 | 762.6 | 0.1922 | 93.34 |
| U-2940 | 70.43 | 0.006313 | 5.192 | 792.5 | 0.0314 | 82.19 |
| OCI-LY19 | 72.49 | 0.02944 | 3.228 | 706.2 | 0.2829 | 80.91 |
| CARNAVAL | 110.6 | 0.009122 | 7.134 | 708.7 | 0.1516 | 77.84 |
| Toledo | 112.3 | 0.002002 | 8.56 | 231.4 | 0.2231 | 27.5 |
| RC-K8 | 115.7 | 0.003371 | 10.06 | 349.2 | 0.07435 | 26.31 |
| SU-DHL-8 | 119.5 | 0.4857 | 2.081 | 363.2 | 0.6025 | 85.44 |
| OCI-LY10 | 125.3 | 0.01417 | 10.16 | 188.9 | 0.3202 | 22.31 |
| SU-DHL-16 | 149.7 | 0.1545 | 7.137 | 492.6 | 0.6619 | 60.79 |
| U-2932 | 163.7 | 0.03595 | 12.8 | 212.8 | 0.5669 | 25.81 |
| WILL-1 | 233.7 | 0.8166 | 4.216 | 549.4 | 2.515 | 79.51 |
| SU-DHL-4 | 296.2 | 0.2777 | 23.44 | 209 | 0.7823 | 25.33 |
| Pfeiffer | 313.5 | 0.04768 | 24.49 | 493.3 | 0.0136 | 51.82 |
| U-2904 | 334.1 | 0.2006 | 7.609 | 456.1 | 3.294 | 77.39 |
| WSU-DLCL | 341.9 | 0.142 | 27.83 | 565.1 | 0.01804 | 59.91 |
| HT | 396.7 | 0.3192 | 30.39 | 225.3 | 0.06622 | 25.16 |
| RIVA | 452.6 | 0.1135 | 36.65 | 242.8 | 0.01774 | 27.92 |
| ROS-50 | 762.1 | 10 | 65.57 | 87.92 | 0.3347 | 10.9 |
| U-2973 | 853.4 | 6.776 | 19.45 | 391.9 | 2.161 | 60.8 |
| DB | 941.4 | 10 | 89.46 | 80.31 | 0.06883 | 11.62 |
| OCI-LY7 | 48.18 | 0.006477 | 4.191 | 682.7 | 0.01627 | 71.18 |
| OCI-LY3 | 965.1 | 10 | 85.63 | 24.63 | 0.000263 | 4.493 |
| DOHH2 | 6.902 | 0.002801 | 0.2066 | 923.9 | 0.01753 | 95.1 |
| RL | 234.8 | 0.008755 | 21.55 | 115.9 | 0.1566 | 13.93 |
| Mino | 62.67 | 0.005782 | 5.638 | 968.2 | 0.002051 | 97.04 |
| Rec-1 | 281.8 | 0.03199 | 21.04 | 508.5 | 0.009258 | 57.27 |
| EHEB | 319.3 | 0.0303 | 28.68 | 65.03 | 0.5062 | 8.42 |
| WA-C3-CD5+ | 474.8 | 0.53 | 44.2 | 162.9 | 0.05244 | 17.47 |
| WA-OSEL | 616.1 | 10 | 54.42 | 69.39 | 0.112 | 7.38 |
| PGA1 | 736.7 | 10 | 69.21 | 48.94 | 0.1219 | 5.075 |
| HG3 | 676.2 | 10 | 59.58 | 131.5 | 0.1107 | 14.28 |
| I83-E95 | 259.2 | 0.01728 | 21.6 | 358.4 | 0.06111 | 40.69 |
| CII | 926.1 | 10 | 78.23 | 238.1 | 0.145 | 26.11 |
| CI | 603.9 | 9.701 | 53.58 | 123.2 | 0.02294 | 13.01 |
| Mec2 | 312.5 | 0.07552 | 25.55 | 339.8 | 0.01331 | 35.28 |
| Mec1 | 866.5 | 10 | 83.45 | 302.4 | 0.2097 | 36.61 |
| SVSL | 368.4 | 0.09517 | 34.07 | 340.2 | 0.002836 | 35.5 |
| Daudi | 196.4 | 0.0006 | 0 | 274 | 2.320 | 84.0 |
| BL-41 | 270.2 | 6.065 | 96.65 | 288.2 | 6.919 | 79.5 |
| MDS-L | 182.6 | 0.0513 | 146.7 | 425.4 | 1.557 | 100 |
| HNT-34 | 353 | 0.026 | 20.47 | 130.1 | 0.8756 | 44.33 |
| GDM-1 | 1455 | 6.8e−22 | 388.4 | 696.9 | 1.625e20 | 265 |
| NCI-H929 | 215.5 | 0.0007 | 6.1 | 16.86 | 11.27 | 7.00 |
| OPM-2 | 210.5 | 0.0003 | 6.65 | 212.6 | 1.316 | 63.00 |
| HuT-102 | 395.4 | 0.0065 | 36.34 | 42.75 | 23.36 | 18.50 |
| Karpas-299 | 283.7 | 0.012 | 8.43 | 14.51 | 167.6 | 8.0 |
| JJN-3 | 278.2 | 0.0004 | 21.6 | 57.97 | 5.14e22 | 26 |
| SK-MM-1 | 202.2 | 0.0008 | 3 | 90.99 | 86.36 | 44.5 |
| L-363 | 309.1 | 0.001 | 27.6 | 2.954 | 7.950 | 2 |
| Karpas-231 | 449.4 | 0.484 | 0 | 5.720 | 895.5 | 5.00 |
| KOPN-8 | 490.2 | 0.0418 | 38.3 | 14.95 | 726.5 | 5.00 |

TABLE 7-continued

Antiproliferative Activity and Apoptotic Effect of Compound 1 in Hematological Cell Lines

| | % Viable Cells | | | Apoptosis | | |
|---|---|---|---|---|---|---|
| Cell Line | AUC | $IC_{50}$ | $E_{max}$ | AUC | $EC_{50}$ | $Y_{max}$ |
| L-428 | 450.4 | 0.252 | 47.3 | 63.35 | 64.50 | 27.50 |
| L-591 | 334.2 | 0.0003 | 34.6 | 45.59 | 1.521 | 20.0 |

AUC = area under the curve;
$IC_{50}$ = 50% inhibitory concentration (μM);
$E_{max}$ = maximum efficacy eliminating tumor cells achieved expressed as the percentage of tumor cells remaining;
$EC_{50}$ = compound concentration that produces half-maximal apoptosis response (μM);
$Y_{max}$ = calculated percent of control at highest concentration of Compound 1.

6.3 Analytical Methods

Typical measurement conditions are provided below:

X-Ray Powder Diffraction (XRPD)

The Rigaku Smart-Lab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ.

Differential Scanning calorimetry (DSC)

DSC analyses were carried out using a TA Instruments Q2000 instrument. The instrument temperature calibration was performed using indium. The DSC cell was kept under a nitrogen purge of −50 mL per minute during each analysis. The sample was placed in a standard, crimped, aluminum pan and was heated from 25° C. to 350° C. at a rate of 10° C. per minute.

Thermogravimetric (TG) Analysis

The TG analysis was carried out using a TA Instruments Q50 instrument. The instrument balance was calibrated using class M weights and the temperature calibration was performed using alumel. The nitrogen purge was ~40 mL per minute at the balance and ~60 mL per minute at the furnace. Each sample was placed into a pre-tared platinum pan and heated from 20° C. to 350° C. at a rate of 10° C. per minute.

Infrared (IR) Spectroscopy

IR spectra were obtained on a Nicolet 6700 FT-IR system. Samples were analyzed using a Nicolet SMART iTR attenuated total reflectance device.

Raman Spectroscopy

Fourier transform (FT) Raman spectra were acquired on a Nicolet model 6700 spectrometer interfaced to a Nexus Raman accessory module. This instrument is configured with a Nd:YAG laser operating at 1024 nm, a $CaF_2$ beam-splitter, and a indium gallium arsenide detector. OMNIC software was used for control of data acquisition and processing of the spectra. Samples were packed into a 3-inch glass NMR tube for analysis.

Nuclear Magnetic Resonance (NMR) Spectroscopy

The $^1H$ NMR spectra were acquired on a Bruker DRX-500 spectrometer located at the Chemistry Department of Purdue University. Samples were prepared by dissolving material in DMSO-$d_6$. The solutions were filtered and placed into individual 5-mm NMR tubes for subsequent spectral acquisition. The temperature controlled (298K) $^1H$ NMR spectra acquired on the DRX-500 utilized a 5-mm cryoprobe operating at an observing frequency of 499.89 MHz.

DVS Analysis

Dynamic vapor sorption (DVS) was measured using DVS advantage (Surface Measurement Systems Ltd). The samples were tested under isotherm (25° C.) at a targeted RH of 0 to 95% full cycle in step mode. For an isotherm test, the chamber temperature is maintained by a water bath at constant 25.0±1.0° C. The relative humidity in the sample chamber is generated by combining different flows of wet and dry nitrogen with variable flow rates. The analysis was performed in 10% RH increments. Sampling rate is 1 sec save data rate is 20 sec. The dm/dt (%) value was set at 0.001 with a dm/dt window of 5 min., a minimum stability duration time of 10 min, and a maximum stage time of 180 min. The sample's equilibrium weight corresponding to each RH was recorded. A sorption isotherm is obtained by plotting equilibrium moisture content versus RH.

6.4 Free Base Polymorphism Screening

A batch of Compound 1 free base starting material was characterized. XRPD showed it is amorphous. TGA showed a weight loss of 7.3% below 200° C. DSC showed several small endotherms below 150° C. A representative XRPD pattern of amorphous Compound 1 free base is shown in FIG. 20.

Compound 1 free base starting material was mixed with various solvents under various conditions in attempts to generate crystalline material. The results are listed in the following table.

TABLE 8

Polymorph Screen of Free Base of Compound 1

| Method | Solvent | Conditions[a] | XRPD Pattern[b] |
|---|---|---|---|
| cooling | acetone | hexanes AS, 60° C. → −15° C.; E | NC |
| | ACN | water AS, 60° C. → −15° C.; E | B + NC |
| | anisole | MTBE AS, 60° C. → −15° C.; E | NC |
| | DCM | hexanes AS, 60° C. → −15° C.; E | NC |
| | DMAc | MTBE AS, 60° C. → −15° C.; E | NC |
| | EtOH | 60° C. → −15° C. | NC |
| | EtOAc | hexanes AS, 60° C. → −15° C.; E | NC |
| | ethyl formate | MTBE AS, 60° C. → −15° C.; E | NC |
| | isopropyl acetate | 60° C. → −15° C. | NC |
| | MeOH | 60° C. → −15° C. | NC |
| | MEK | MTBE AS, 60° C. → −15° C.; E | NC |
| | 2-MeTHF | hexanes AS, 60° C. → −15° C. | NC |
| | nitro methane | MTBE AS, 60° C. → −15° C.; E | NC |
| | NMP | water AS, 60° C. → −15° C.; E | NC |
| | 2-PrOH | 40° C. → −15° C. | NC |
| | THF | water AS, 60° C. → −15° C. | A + NC |
| | toluene | 60° C. → −15° C. | NC |
| | 2-PrOH/water (95:5) | 60° C. → −15° C. | NC |
| slow evap-oration | acetone | foil w/3 pin holes, RT | NC |
| | ACN | foil w/3 pin holes, RT | NC |
| | anisole | foil w/3 pin holes, RT | NC |
| | DCM | foil w/3 pin holes, RT | NC |
| | DMAc | foil w/3 pin holes, RT | NC |
| | EtOH | foil w/3 pin holes, RT | NC |
| | EtOAc | foil w/3 pin holes, RT | NC |
| | ethyl formate | foil w/3 pin holes, RT | NC |
| | isopropyl acetate | foil w/3 pin holes, RT | NC |
| | MeOH | foil w/3 pin holes, RT | NC |
| | MEK | foil w/3 pin holes, RT | NC |
| | 2-MeTHF | foil w/3 pin holes, RT | NC |
| | nitromethane | foil w/3 pin holes, RT | NC |
| | NMP | foil w/3 pin holes, RT | A (LC) |
| | THF | foil w/3 pin holes, RT | NC |
| | toluene | foil w/3 pin holes, RT | NC |
| | acetone/water (95:5) | foil w/3 pin holes, RT | NC |
| | ACN/water (95:5) | foil w/3 pin holes, RT | NC |
| | 2-PrOH/water (95:5) | foil w/3 pin holes, RT | NC |
| | THF/water (95:5) | foil w/3 pin holes, RT | NC |
| solvent/ anti-solvent | acetone | EtOH AS, RT | NC |
| | | hexanes AS, RT | NC |
| | | 2-PrOH AS, RT | NC |
| | | water AS, RT | B |
| | ACN | MTBE AS, RT | NC |
| | | 2-PrOH AS, RT | NC |
| | | water AS, RT | A |
| | anisole | MTBE AS, RT | NC |
| | | 2-PrOH AS, RT | NC |
| | DCM | EtOH AS, RT | NC |
| | | hexanes AS, RT | NC |
| | | MTBE AS, RT | NC |
| | | 2-PrOH AS, RT | NC |
| | DMAc | hexanes AS, RT | NC |
| | | MTBE AS, RT | NC |
| | | 2-PrOH AS, RT | NC |
| | EtOAc | EtOH AS, RT | NC |
| | | hexanes AS, RT | NC |
| | | MTBE AS, RT | NC + pk |
| | | 2-PrOH AS, RT | NC |
| | ethyl formate | MTBE AS, RT | NC |
| | | 2-PrOH AS, RT | NC |

TABLE 8-continued

Polymorph Screen of Free Base of Compound 1

| Method | Solvent | Conditions[a] | XRPD Pattern[b] |
|---|---|---|---|
| | nitromethane | MTBE AS, RT | NC |
| | | 2-PrOH AS, RT | NC |
| | NMP | MTBE AS, RT | NC |
| | | 2-PrOH AS, RT | NC |
| | | water AS, RT | NC |
| | THF | EtOH AS, RT | NC |
| | | hexanes AS, RT | LC |
| | | 2-PrOH AS, RT | NC |
| | | water AS, RT | A (shifted)<br>A |
| slurry | EtOH | RT, 7 days | A + NC |
| | isopropyl acetate | RT, 7 days | NC |
| | MeOH | RT, 7 days | NC |
| | MTBE | 40° C., 7 days | NC + pk |
| | toluene | RT, 7 days | LC |
| | water | 40° C., 6 days | A<br>B |
| | 95:5 2-PrOH/ water | RT, 7 days | NC |
| stress | none | 40° C., 75% RH | NC |
| | | 70° C., closed vial | NC |
| vapor diffusions | acetone | $Et_2O$ AS; RT→5° C. | NC |
| | | hexanes AS; RT→5° C. | NC |
| | | MTBE AS; solids | NC |
| | ACN | MTBE AS; RT→5° C. | NC |
| | | 2-PrOH AS; RT→5° C. | NC |
| | | water AS; RT→5° C. | B |
| | DCM | $Et_2O$ AS; solids | NC |
| | | hexanes AS; solids | NC |
| | EtOAc | hexanes AS; solids | NC |
| | | MTBE AS; solids | NC |
| | NMP | water AS; RT→5° C. | NC |
| | THF | hexanes AS; solids | NC |
| | | MTBE AS; solids | NC |
| | | water AS; RT→5° C. | A + B (LC) |

[a]AS = anti-solvent;
E = evaporation;
NC = no crystallization;
RT = room temperature
[b]NC = non-crystalline,
LC = low crystallinity,
pk = peak Two unique XRPD patterns were identified, designated as Form A and Form B of free base of Compound 1, respectively. The two forms were analyzed by XRPD, DSC, TG, and NMR. The data is summarized in the following table.

TABLE 9

Characterization of Form A and Form B of free base of Compound 1

| Form | Technique | Figure No. | Result |
|---|---|---|---|
| Form A | XRPD | FIG. 1 | crystalline |
| | DSC | FIG. 2 | endo 67.6, 112.0° C. |
| | TG | | 1.3% start to 50° C., and 1.4% 50 to 200° C. |
| | NMR | not shown | consistent with structure impurities: 1.16 (t), 1.98 (s), 4.01 (q) |
| Form B | XRPD | FIG. 3 | crystalline |
| | DSC | FIG. 4 | endo 82.5, 107.0, 138.1° C. |
| | TG | | 0.9% start to 225° C. |
| | NMR | not shown | consistent with structure |

6.5 Salts Screening No. 1

Compound 1 free base starting material was mixed with various counterions under various conditions in attempts to generate crystalline salts. Approximately 15 different counterions were used in the salt screen, and the results are listed in the following table.

TABLE 10

Salt Screening of Compound 1

| Acid | Conditions[a] | XRPD Pattern[b] |
|---|---|---|
| L-aspartic | G, 1:1 acetone: water, ~20 mins | NC + acid |
| | SL, 1:1 MeOH: water, 70° C. | NC |
| | C, 1:2 ACN: water, RT→−15° C. | NC |
| citric | C, acetone, −15° C., 2 days; hex AS E | NC |
| | C, THF, −15° C., 2 days; hex AS; E | NC |
| | E, MeOH, RT | NC |
| | G, MEK, ~20 minutes | NC + acid |
| | SL, ACN, RT, 5 days | NC |
| fumaric | C, acetone, −15° C., 2 days | NC |
| | C, THF, −15° C., 2 days; hex AS; solids | NC |
| | E, MeOH, RT | NC |
| | G, MEK, ~20 minutes | NC |
| | SL, ACN, RT, 5 days | A |
| galactaric (mucic) | C, acetone, −15° C., 2 days; hex AS; E | NC + acid |
| | C, THF, −15° C., 2 days; hex AS; E | NC + acid |
| | E, MeOH, RT | NC + acid |
| | G, MEK, ~20 minutes | NC + acid |
| | SL, ACN, RT, 5 days | acid |
| D-gluconic | P, acetone, RT, 4 days | NC |
| | C, THF, −15° C., 2 days; hex AS; E | NC |
| | E, MeOH, RT | NC |
| | G, MEK, ~20 minutes | NC |
| | SL, ACN, RT, 5 days | NC |
| glutamic | C, acetone, −15° C., 2 days; hex AS; E | NC |
| | C, THF, −15° C., 2 days; hex AS; E | NC |
| | E, MeOH, RT | NC |
| | G, MEK, ~20 minutes | NC + acid |
| | SL, ACN, RT, 5 days | acid |
| glycolic | C, acetone, −15° C., 2 days; hex AS; E | NC |
| | C, THF, −15° C., 2 days; hex AS; solids | NC |
| | E, MeOH, RT | NC |
| | G, MEK, ~20 minutes | NC |
| | SL, ACN, RT, 5 days | NC |
| HCl (1 equivalent) | P, acetone, RT, 4 days | A |
| | P, THF, RT, 4 days | |
| | E, MeOH, RT | NO |
| | G, MEK, ~20 minutes | A |
| | SL, ACN, RT, 5 days | A + B |
| HCl (2 equivalents) | P, acetone, RT, 4 days | A + B |
| | P, THF, RT, 4 days | A + B (shifting) |
| | E, MeOH, RT | NC |
| | G, MEK, ~20 minutes | B |
| | SL, ACN, RT, 5 days | |
| maleic | C, acetone, −15° C., 2 days | NC |
| | C, THF, −15° C., 2 days | A + NC |
| | E, MeOH, RT | NC |
| | G, MEK, ~20 minutes | NC + pk |
| | SL, ACN, RT, 5 days | A |
| methanesulfonic | P, acetone, RT, 4 days | NC |
| | P, THF, RT, 4 days | LC |
| | E, MeOH, RT | NC |
| | G, MEK, ~20 minutes | NC |
| | SL, ACN, RT, 5 days | NC |
| phosphoric | P, acetone, RT, 4 days | NC + pk |
| | P, THF, RT, 4 days | NC |
| | E, MeOH, RT | NC |
| | G, MEK, ~20 minutes | NC |
| | SL, ACN, RT, 5 days | NC |
| succinic | C, acetone, −15° C., 2 days; hex AS; E | NC |
| | C, THF, −15° C., 2 days; hex AS; E | NC + pk |
| | E, MeOH, RT | NC |
| | G, MEK, ~20 minutes | NC + acid |
| | SL, ACN, RT, 5 days | NC |

TABLE 10-continued

Salt Screening of Compound 1

| Acid | Conditions[a] | XRPD Pattern[b] |
|---|---|---|
| sulfuric | P, acetone, RT, 4 days | LC |
| | P, THF, RT, 4 days | NC |
| | E, MeOH, RT | NC |
| | G, MEK, ~20 minutes | NC |
| | SL, ACN, RT, 5 days | NC |
| L-tartaric | C, acetone, −15° C., 2 days; hex AS; E | NC |
| | C, THF, −15° C., 2 days; hex AS; E | NC |
| | E, MeOH, RT | NC |
| | G, MEK, ~20 minutes | NC + acid |
| | SL, ACN, RT, 5 days | NC |
| p-toluenesulfonic | C, acetone, −15° C., 2 days; hex AS; solids | A |
| | C, THF, −15° C., 2 days; hex AS; solids | NC |
| | E, MeOH, RT | NC |
| | G, MEK, ~20 minutes | B + acid |
| | SL, ACN, RT, 5 days | C |

[a]AS = anti-solvent; P = precipitate; RT = room temperature; S/AS = solvent/anti-solvent; SL = slurry; G = grind; C = cooling; E = evaporation
[b]NC = non-crystalline, LC = low crystallinity; pk = peak; A, B, etc. = form Several materials were identified that exhibit an XRPD pattern suggestive of new phase formation. That is, the patterns contain peaks that do not arise from Compound 1 free base or the acid used. The acids used in those experiments are fumaric, hydrochloric, maleic, and p-toluenesulfonic.

All samples having an XRPD pattern suggestive of new phase formation were analyzed by DSC, TG, and NMR. The results are summarized in the following table.

TABLE 11

Characterization of Crystalline Salts of Compound 1

| Salt/ Sample ID | Technique | Figure No. | Result |
|---|---|---|---|
| fumarate | XRPD | | crystalline |
| Form A | DSC | | endo 201.7° C. |
| | TG | | 0.5% start to 150° C. |
| | | | 10.2% 150 to 215° C. |
| | NMR | | consistent with salt formation stoichiometry is 1:2 API:acid |
| hydrochloride | XRPD | | crystalline |
| | DSC | | endo 217.2° C., exo 226.5° C. |
| Form A | TG | | 0.9% start to 200° C. |
| | | | 3.2% 200 to 235° C. |
| | NMR | | consistent with salt formation |
| hydrochloride | XRPD | FIG. 9 | crystalline |
| | DSC | FIG. 10 | exo 230.4° C. |
| Form B | TG | | 1.6% start to 175° C. |
| | | | 5.3% 175 to 230° C. |
| | NMR | not shown | consistent with salt formation |
| maleate | XRPD | FIG. 15 | crystalline |
| Form A | DSC | FIG. 16 | endo 174.2° C. |
| | TG | | 0.2% start to 150° C. |
| | | | 8.8% 150 to 185° C. |
| | NMR | not shown | consistent with salt formation 1.7 moles acid per mole of API, possible 1:1 salt with excess acid or mix of 1:1 and 1:2 API:acid salt |
| Tosylate | XRPD | | crystalline |
| Form A | DSC | | endo 189.4° C. |
| | TG | | 0.7% start to 225° C. |
| | NMR | | consistent with salt formation stoichiometry is 1:1 API:acid |

6.6 Salts Screening No. 2

A batch of Compound 1 free base was characterized by XRPD, TGA, DSC, and DVS. XRPD confirmed that it is amorphous. TGA showed that there were several steps of weight losses below 200° C. prior to decomposition. The results from the dynamic vapor sorption (DVS) study demonstrated that Compound 1 amorphous free base showed relatively high hygroscopicity below 75% RH. The free base picked up moisture (~6.0% wt) slowly and steadily from dry up to 90% RH. During the desorption, water content slowly released from 90% RH down to dry (0% RH). The sorption/desorption was almost reversible during two full cycles.

HCl Salt

Several experiments were performed to search for crystalline HCl salts of Compound 1, using hydrochloric acid added to different solvents.

In one experiment, 49.2 mg of Compound 1 free base was weighed into a 4-mL glass vial, and 1.0 mL EtOAc was added. The mixture became close to a clear solution, followed by addition 0.8 mL of 0.1 N HCl in EtOAc. A cloudy suspension was observed, and then 0.2 mL of 0.1 N HCl in water was added. The suspension was placed in a fume hood for slow evaporation. Solids were sticky to the wall. The solid particles were examined by XRPD, and determined to be crystalline material, namely Form A of hydrochloride salt of Compound 1.

In one experiment, 10.5 mg of Compound 1 free base was weighed into a 4-mL glass vial, and 1 mL of EtOAc was added, followed by addition 0.2 mL of 0.1 N HCl in EtOAc. The mixture was cloudy. The suspension was placed in a fume hood for slow evaporation. The solid particles were examined by XRPD, and were determined to be crystalline material, namely Form A of hydrochloride salt of Compound 1.

In one experiment, 16.6 mg of Compound 1 free base was weighed into a 4-mL glass vial, and 1 mL of EtOAc was added, followed by addition 0.05 mL of water, and 0.345 mL of 0.1 N HCl in EtOAc. The mixture was cloudy. The suspension was placed in a fume hood for slow evaporation and crystalline aggregates formed. The solid particles were examined by XRPD, and were determined to be crystalline material, namely Form A of hydrochloride salt of Compound 1.

In one experiment, 25.6 mg of Compound 1 free base was weighed into a 4-mL glass vial, and 1 mL of acetone was added, followed by addition 0.45 mL of 0.1 N HCl in acetone, and the mixture was cloudy. Additionally, 0.07 mL of 0.1 N HCl in water was added. The mixture became a clear solution. The solution was placed in a fume hood for slow evaporation. Seed suspension was introduced and precipitation was observed. The solid particles were examined by XRPD, and determined to be crystalline material, namely Form A of hydrochloride salt of Compound 1.

In one experiment, 26.1 mg of Compound 1 free base was weighed into a 4-mL glass vial, 1 mL of acetone and 0.07 mL of 0.1 N HCl in water were added, followed by addition of 0.45 mL of 0.1 N HCl in acetone. The mixture was a clear solution. The solution was placed in a fume hood for slow evaporation, and crystals grew around the vial wall, just above the liquid/air interface between the wall and liquid. The solid particles were examined by XRPD, and determined to be crystalline material, namely Form A of hydrochloride salt of Compound 1.

In one experiment, 44.2 mg of Compound 1 free base was weighed into a 4-mL glass vial, 2 mL of EtOAc was added, followed by addition 0.9 mL of 0.1 N HCl in EtOAc. The mixture was cloudy. The suspension was placed in a fume hood for slow evaporation and crystalline aggregates formed. The solid particles were examined by XRPD, determined to be crystalline material, namely Form A of hydrochloride salt of Compound 1, and further characterized by TGA and DSC. TGA profile showed multiple stages of weight loss upon heating prior to decomposition: 1.8% below 100° C., 2.1% from 100 to 200° C., and 1.5% around melting temperature. DSC spectrum showed a broad endothermic peak at relatively low temperature (<100° C.), and a small endothermic peak with onset and peak temperatures of 204.9° C. and 213.0° C., respectively, due to the melting of solid, followed by exothermic peak due probably to decomposition. The dynamic vapor sorption (DVS) profile showed the solid was moderate hygroscopic below 90% RH. The HCl salt picked up moisture (~2.9% wt) slowly and steadily from dry up to 90% RH. During the desorption, water content was slowly released from 90 down to dry 0% RH. The sorption/desorption was almost reversible during two full cycles. NMR showed the chemical shifts resulted from salt formation and minor residual solvents.

In one experiment, 53.9 mg of Compound 1 free base was weighed into a 4-mL glass vial, 2 mL of EtOAc was added, followed by addition 100 μL of 0.1 N HCl in water, and 1.0 mL of 0.1 N HCl in EtOAc. The mixture was a sticky suspension. The suspension was placed in a fume hood for slow evaporation and crystalline aggregates formed. The solid particles were examined by XRPD, and determined to be crystalline material, namely Form A of hydrochloride salt of Compound 1.

In one experiment, 26.5 mg of Compound 1 free base was weighed into a 4-mL glass vial, 1 mL of acetone was added, and then 0.52 mL of 0.1 N HCl in acetone. The mixture remained a clear solution. The solution was placed in a fume hood for slow evaporation, and crystals grew in the solution and on the bottom. The solid particles were examined by XRPD, determined to be crystalline material, namely Form A of hydrochloride salt of Compound 1.

In one experiment, 26.2 mg of Compound 1 free base was weighed into a 4-mL glass vial, 1 mL of EtOAc was added first, and then 0.02 mL of water was added, followed by addition of 0.52 mL of 0.1 N HCl in EtOAc. The mixture became cloudy. The solid particles were examined by XRPD, and determined to be crystalline material, namely Form A of hydrochloride salt of Compound 1. It remained the same crystal form after drying in vacuum oven at 35° C.

In one experiment, solid particles generated from several experiments above were placed together in a 4-mL glass vial, and then 1 mL of water was added. The suspension was covered and placed at room temperature for equilibrium over a week. The solid form after slurry remained as Form A, and was then characterized by TGA, DSC, and DVS. The TGA profile showed multiple stages of weight loss upon heating prior to decomposition, 0.7% below 100° C., and 3.9% around melting temperature. DSC spectrum showed a broad endothermic peak with onset and peak temperatures of 196.4° C. and 212.6° C., respectively, due to the melting of solid, followed by exothermic peak due probably to decomposition. The DVS profile was similar to the sample from an earlier experiment (44.2 mg scale) discussed above.

In one experiment, 26.2 mg of Compound 1 free base was weighed into a 4-mL glass vial, 1 mL of MEK was added, and then 0.02 mL of 0.1 N HCl in water was added. The mixture became a clear solution, and was followed by addition of 0.49 mL of 0.105 N HCl in MEK. The mixture became cloudy immediately. The solid particles were examined by XRPD, and the solid sample was also examined by TGA and DSC, and determined to be crystalline material, namely Form A of hydrochloride salt of Compound 1.

In one experiment, 26.2 mg of Compound 1 free base was weighed into a 4-mL glass vial, 1 mL of MEK was added, and then 0.49 mL of 0.105 N HCl in MEK was added. The mixture became a clear solution, and was followed by addition of 0.02 mL of 0.1 N HCl in water. The mixture became cloudy immediately. The solid particles were examined by XRPD, the solid sample was also examined by TGA and DSC, and determined to be crystalline material, namely Form A of hydrochloride salt of Compound 1. TGA profile showed multiple stages of weight loss upon heating prior to decomposition, 0.8% below 100° C., and 3.7% around melting temperature. DSC spectrum showed a broad endothermic peak endothermic peak with onset and peak temperatures of 219.7° C. and 233.8° C., respectively, due to the melting of solid, followed by exothermic peak due probably to decomposition.

In one experiment, 1.07 g of Compound 1 free base was weighed into a glass beaker, 25 mL of EtOAc was added, followed by addition 20 mL of 0.1 N HCl in EtOAc. The mixture was cloudy. The suspension was placed in a fume hood for slow evaporation. The initial solid was amorphous by XRPD, was slurried for another hour and it became crystalline Form A of hydrochloride salt of Compound 1. A sample was dried in a vacuum oven overnight and then re-slurried in water, and the final product was Form A of hydrochloride salt of Compound 1.

In one experiment, 0.455 g of Compound 1 free base was weighed into a glass beaker, 5 mL of MEK was added, followed by addition 9.0 mL of 0.1 N HCl in MEK. The mixture was cloudy. The suspension was placed in a fume hood for slow evaporation. The initial solid was crystalline Form A by XRPD.

Without being limited by a particular theory, the variation of onset and peak temperatures of melting point observed for Form A in these experiments are due to factors such as the crystallinity, crystal defects, and degree of content of amorphous.

2×HCl Salt

In one experiment, 45.5 mg of Compound 1 free base was weighed into a 4-mL glass vial, and 0.9 mL of acetone was added. The mixture became clear, and then 1.8 mL of 0.1 N HCl in acetone was introduced. The mixture remained a clear solution. The solution was placed in a fume hood for slow evaporation, and crystals grew in the solution and on the bottom. XRPD (FIG. 21) of the solid form obtained from this experiment was different from mono-hydrochloride salt Form A, and is designated as Form C of hydrochloride salt of Compound 1. The solid also demonstrated different profile of TGA, DSC, and DVS. The TGA profile showed multiple stages of weight loss upon heating prior to decomposition: 3.8% below 100° C. and another 4.0% from 100 to 200° C. The DSC spectrum showed a broad endothermic event at relatively low temperature (<125° C.), and another endothermic peak with onset and peak temperatures of 138.0° C. and 151.6° C., respectively, due to the melting of solid, followed by an exothermic peak due probably to decomposition. The dynamic vapor sorption (DVS) profile showed the solid was highly hygroscopic below 90% RH. The solid sample picked up moisture (~8.0% wt) slowly and steadily from dry up to 80% RH, followed by quick gain (~6.7%) from 80% RH to 90% RH. During the desorption, the water content rapidly released (~7.0%) from 90 to 80% RH, and then the rest water content was steadily freed while the relative humidity decreased to dry (0% RH).

Besylate Salt

In one experiment, 24.3 mg of Compound 1 free base was weighed into a 4-mL glass vial, and 1 mL of MEK was added. The mixture became a clear solution, and 0.5 mL of 0.1 N benzenesulfonic acid in MEK was added. Precipitation occurred immediately. Crystalline material was observed by microscope and confirmed by XRPD, namely Form A of besylate salt of Compound 1.

In one experiment, 255.3 mg of Compound 1 free base was weighed into a 4-mL glass vial, and 5 mL of acetone was added. The mixture became a clear solution, followed by addition of 5.0 mL of 0.1 N benzenesulfonic acid in MEK. Precipitation occurred immediately. Crystalline material was observed by microscope and confirmed by XRPD (FIG. 17). The solid was also characterized by thermal analyses using both TGA and DSC. The TGA profile (FIG. 18) showed weight loss was very minor (0.25%) upon heating up to 150° C. The DSC spectrum (FIG. 19) showed an endothermic peak with onset and peak temperatures of 164.5° C. and 175.4° C., respectively, due to the melting of solid.

6.7 Preparation and Polymorphism Screening of Hydrochloride Salt of Compound 1

The hydrochloride salt of Compound 1 was prepared from the free base of Compound 1 in three experiments. Initially, two small scale (0.1 g scale) experiments were performed (slurry in acetone for 1 day and slurry in THF for 1 day). The products from both experiments were confirmed to be hydrochloride salt polymorph Form A. To determine stoichiometry, both samples were tested for carbon, hydrogen, nitrogen, and chloride content. The elemental data (not shown) was consistent with a 1:1 API:acid salt. The hydrochloride salt was then made at 10 g scale (slurry in acetone for 2 days) and further characterized. Characterization data are summarized in the following table.

TABLE 12

Characterization of Large Scale Compound 1 HCl Salt

| | |
|---|---|
| XRPD | FIG. 5 |
| XRPD Result | HCl salt Form A |
| DSC/TG | FIG. 6 |
| DSC Result | endo 217.7° C., exo 227.0° C. |
| TG Result | 1.5% start to 200° C.<br>2.7% 200 to 230° C. |
| NMR Result | consistent with structure |

| | — | % C | % H | % N | % Cl |
|---|---|---|---|---|---|
| Elemental | theo[a] | 58.8 | 5.5 | 12.3 | 6.2 |
| Analysis Result | result | 57.9 | 5.4 | 11.8 | 5.8 |

[a]theoretical values for a 1:1 salt

The Compound 1 HCl salt solids were mixed with various solvents under various conditions in attempts to generate polymorphs. The results are listed in the following table. Only one polymorph (Form A of Compound 1 HCl salt) was identified in this study.

TABLE 13

| Polymorph Screening of Compound 1 hydrochloride salt | | | |
|---|---|---|---|
| Method | Solvent | Conditions[a] | XRPD Pattern[b] |
| cooling | DMAc | 200° C. → −15° C.; E | A |
| | DMSO | acet AS, 60° C.→−15° C.; E | A + NC |
| | | ACN AS, 60° C.→−15° C.; E | NC |
| | | anisole AS, 60° C.→−15° C.; E | A + NC |
| | | EtOH AS, 60° C.→−15° C.;' E | A + NC |
| | | EtOAc AS, 60° C.→−15° C.; E | A + NC |
| | | IPAc AS, 60° C.→−15° C.; E | A + NC |
| | | MTBE AS, 60° C.→−15° C.; E | A + NC |
| | | 2-PrOH AS, 60° C.→−15° C.; E | NC |
| | | THF AS, 60° C.→−15° C.; E | A + NC |
| | | tol AS, 60° C.→−15° C.; E | A + NC |
| | MeOH | 65° C. → −15° C.; E | A |
| | NMP | 165° C. → −15° C.; E | A + NC |
| | water | 100° C. → −15° C.; E | NC |
| | ACN/water (95/5) | 100° C. → −15° C.; E | A |
| | THF/water (95/5) | 100° C. → −15° C. | A |
| evaporation | DMAc | open vial, RT | A (LC) |
| | DMSO | open vial, RT | A |
| | MeOH | open vial, RT | A |
| | NMP | open vial, RT | A |
| | water | open vial, RT | A |
| | ACN/water (95/5) | open vial, RT | A |
| | THF/water (95/5) | open vial, RT | NC |
| precipitation | DMAc | acetone AS, 60° C.→−15° C.; E | A + NC |
| | | DCM AS, 60° C.→−15° C.; E | A + NC |
| | | EtOAc AS, 60° C.→−15° C.; E | A + NC |
| | | 2-PrOH AS, 60° C.→−15° C.; E | A + NC |
| | | THF AS, 60° C.→−15° C.; E | A + NC |
| | | toluene AS, 60° C.→−15° C.; E | A |
| | MeOH | acetone AS, 60° C.→−15° C.; E | A + NC |
| | | DCM AS, 60° C.→−15° C.; E | A + NC |
| | | EtOAc AS, 60° C.→−15° C.; E | A |
| | | $Et_2O$ AS, 60° C.→−15° C.; E | A |
| | | toluene AS, 60° C.→−15° C.; E | A |
| | NMP | acetone AS, 60° C.→−15° C.; E. $Et_2O$ triturate | A + NC |
| | | ACN AS, 60° C.→−15° C.; E. $Et_2O$ triturate | A + NC |
| | | DCM AS, 60° C.→−15° C.; E | A + NC |
| | | EtOAc AS, 60° C.→−15° C.; E. $Et_2O$ triturate | A + NC |
| | | 2-PrOH AS, 60° C.→−15° C.; E | A + NC |
| | | THF AS, 60° C.→−15° C.; E. $Et_2O$ triturate | NC |
| | water | acetone AS, 60° C.→−15° C.; E | NC |
| | | 2-PrOH AS, 60° C.→−15° C.; E | NC |
| | | THF AS, 60° C.→−15° C.; E | NC |
| | ACN/water (95/5) | acetone AS, 60° C.→−15° C.; E | A |
| | | 2-PrOH AS, 60° C.→−15° C.; E | A |
| | | THF AS, 60° C.→−15° C.; E | A |
| slurry | acetone | RT, 7 days | A |
| | | 50° C., 2 days | A |
| | acetonitrile | RT, 7 days | A |
| | | 50° C., 2 days | A |
| | anisole | RT, 7 days | A |
| | | 50° C., 2 days | A |
| | DCM | RT, 7 days | A |
| | | 50° C., 2 days | A |
| | DMAc | RT, 7 days | A |
| | | 50° C., 2 days | A |
| | EtOH | RT, 7 days | A |
| | | 50° C., 2 days | A |
| | EtOAc | RT, 7 days | A |
| | | 50° C., 2 days | A |
| | ethyl formate | RT, 7 days | A |
| | | 50° C., 2 days | A |
| | isopropyl acetate | RT, 7 days | A |
| | | 50° C., 2 days | A |
| | MeOH | RT, 7 days | A |
| | | 50° C., 2 days | A |
| | MEK | RT, 7 days | A |
| | | 50° C., 2 days | A |
| | MTBE | RT, 7 days | A |
| | | 50° C., 2 days | A |

TABLE 13-continued

| Polymorph Screening of Compound 1 hydrochloride salt | | | |
|---|---|---|---|
| Method | Solvent | Conditions[a] | XRPD Pattern[b] |
| | 2-MeTHF | RT, 7 days | A |
| | | 50° C., 2 days | A |
| | nitromethane | RT, 7 days | A |
| | | 50° C., 2 days | A |
| | NMP | RT, 7 days | A |
| | | 50° C., 2 days | A |
| | 2-propanol | RT, 7 days | A |
| | | 50° C., 2 days | A |
| | tetrahydrofuran | RT, 7 days | A |
| | | 50° C., 2 days | A |
| | toluene | RT, 7 days | A |
| | | 50° C., 2 days | A |
| | water | RT, 7 days | A |
| | | 50° C., 2 days | A |
| | acetone/water (95/5) | RT, 7 days | A |
| | | 50° C., 2 days | A |
| | ACN/water (95/5) | RT, 7 days | A |
| | | 50° C., 2 days | A |
| | 2-PrOH/water (95/5) | RT, 7 days | A |
| | | 50° C., 2 days | A |
| | THF/water (95/5) | RT, 7 days | A |
| | | 50° C., 2 days | A |
| heat/humidity | water vapor | RT, 59% RH | A |
| | | RT, 75% RH | A |
| | | RT, 97% RH | A |
| | | 40° C., 75% RH | A |
| | none | RT, 0% RH | A |

[a]AS = anti-solvent; NC = no crystallization; RH = relative humidity; RT = room temperature; E = evaporation
[b]NC = non-crystalline; pks = peaks; A, B, etc. = form

6.8 Preparation and Polymorphism Screening of Fumarate Salt of Compound 1

In one study, Form A of fumarate salt of Compound 1 was prepared from a precipitation experiment involving acetone and hexanes. The solids crystallized within 5 hours, and were allowed to stir at room temperature for 2 days.

In another study, the fumarate salt of Compound 1 was prepared from the free base of Compound 1 in several experiments. Initially, several small scale experiments were performed. Poorly crystalline material was obtained from slurries carried out at ambient temperature (250 mg scale, slurry in acetonitrile at room temperature for 1 day, or slurry in acetonitrile at room temperature for 6 days). Highly crystalline material was obtained by increasing the slurry temperature and the product was confirmed to be fumarate salt polymorph Form A (30 mg scale, slurry in acetonitrile at 50° C. for 1 day). The experiment was repeated at larger scale (3.2 g scale, slurry in acetonitrile at 50° C. for 3 days) and the resulting material was further characterized. Characterization data are summarized in the following table.

TABLE 14

| Characterization of Large Scale Compound 1 Fumarate Salt | |
|---|---|
| XRPD | FIG. 11 |
| XRPD Result | fumarate Form A |
| DSC/TG | FIG. 12 |
| DSC Result | endo 198.3° C. |
| TG Result | 0.5% start to 150° C.<br>7.9% 150 to 205° C. |
| NMR Result | consistent with structure<br>1:2 API:acid salt |

The Compound 1 fumarate salt solids were mixed with various solvents under various conditions in attempts to generate polymorphs. The results are listed in the following table. Only one polymorph (Form A of Compound 1 fumarate salt) was identified in this study.

TABLE 15

| Polymorph Screening of Compound 1 Fumarate salt | | | |
|---|---|---|---|
| Method | Solvent | Conditions[a] | XRPD Pattern[b] |
| cooling | DMSO | acetone AS, 60° C.→−15° C.; E | NC + pks |
| | | ACN AS, 60° C.→−15° C.; E | NC + pks |
| | | anisole AS, 60° C.→−15° C.; E | NC + pks |
| | | EtOH AS, 60° C.→−15° C.; E | NC |
| | | EtOAc AS, 60° C.→−15° C.; E | NC + pks |
| | | IPAc AS, 60° C.→−15° C.; E | NC + pks |
| | | MTBE AS, 60° C.→−15° C.; E | NC + pks |
| | | 2-MeTHF AS, 60° C.→−15° C.; E | NC + pks |
| | | 2-PrOH AS, 60° C.→−15° C.; E | NC + pks |
| | | toluene AS, 60° C.→−15° C.; E | NC + pks |

TABLE 15-continued

Polymorph Screening of Compound 1 Fumarate salt

| Method | Solvent | Conditions[a] | XRPD Pattern[b] |
|---|---|---|---|
| | MeOH | 65° C. → −15° C.; E | A (LC) |
| | THF | 65° C. → −15° C.; E | NC + pks |
| | water | 100° C. → −15° C.; E | NC |
| | acetone/water (95/5) | 100° C. → −15° C.; E | NC |
| | ACN/water (95/5) | 100° C. → −15° C.; E | NC + pks |
| | THF/water (95/5) | 100° C. → −15° C.; E | NC + pks |
| evaporation | DMAc | open vial, RT | NC |
| | DMSO | open vial, RT | NC + pks |
| | MeOH | open vial, RT | NC |
| | NMP | open vial, RT | NC |
| | THF | open vial, RT | NC + pk |
| | water | open vial, RT | NC + pk |
| | acetone/water (95/5) | open vial, RT | NC + pk |
| | ACN/water (95/5) | open vial, RT | NC + pk |
| | 2-PrOH/water (95/5) | open vial, RT | NC + pk |
| | THF/water (95/5) | open vial, RT | NC + pk |
| precipitation | DMAc | acetone AS, 60° C.→−15° C.; E | NC |
| | | DCM AS, 60° C.→−15° C.; E | NC + pks |
| | | EtOAc AS, 60° C.→−15° C.; E | NC + pks |
| | | MTBE AS, 60° C.→−15° C.; E | NC + pks |
| | | 2-PrOH AS, 60° C.→−15° C.; E | NC |
| | | toluene AS, 60° C.→−15° C.; E | NC + pks |
| | MeOH | acetone AS, 60° C.→−15° C.; E | A + NC |
| | | DCM AS, 60° C.→−15° C.; E | NC |
| | | EtOAc AS, 60° C.→−15° C.; E | NC + pk |
| | | $Et_2O$ AS, 60° C.→−15° C.; E | NC |
| | | toluene AS, 60° C.→−15° C.; E | A + NC |
| | NMP | acetone AS, 60° C.→−15° C.; E. $Et_2O$ triturate | NC + pks |
| | | ACN AS, 60° C.→−15° C.; E. $Et_2O$ triturate | NC + pks |
| | | DCM AS, 60° C.→−15° C.; E. $Et_2O$ triturate | NC + pks |
| | | EtOAc AS, 60° C.–>−15° C.; E. $Et_2O$ triturate | NC + pks |
| | | MTBE AS, 60° C.→−15° C.; E | NC + pks |
| | | 2-PrOH AS, 60° C.→−15° C.; E. $Et_2O$ triturate | NC + pks |
| | | toluene AS, 60° C.→−15° C.; E | NC + pks |
| | water | 2-PrOH AS, 60° C.→−15° C.; E | NC |
| | THF/water (95/5) | acetone AS, 60° C.→−15° C.; E | NC + pk |
| | | 2-PrOH AS, 60° C.→−15° C.; E | NC + pk |
| slurry | acetone | RT, 7 days | A |
| | | 50° C., 2 days | A |
| | acetonitrile | RT, 7 days | A |
| | | 50° C., 2 days | A |
| | anisole | RT, 7 days | A |
| | | 50° C., 2 days | A |
| | DCM | RT, 7 days | A |
| | | 50° C., 2 days | A |
| | EtOH | RT, 7 days | A |
| | | 50° C., 2 days | A |
| | EtOAc | RT, 7 days | A |
| | | 50° C., 2 days | A |
| | ethyl formate | RT, 7 days | A |
| | | 50° C., 2 days | A |
| | isopropyl acetate | RT, 7 days | A |
| | | 50° C., 2 days | A |
| | MeOH | RT, 7 days | A |
| | | 50° C., 2 days | A |
| | MEK | RT, 7 days | A |
| | | 50° C., 2 days | A |
| | MTBE | RT, 7 days | A |
| | | 50° C., 2 days | A |
| | 2-MeTHF | RT, 7 days | NC + pk |
| | | 50° C., 2 days | A |
| | nitromethane | RT, 7 days | A |
| | | 50° C., 2 days | A |
| | 2-propanol | RT, 7 days | A |
| | | 50° C., 2 days | A |
| | tetrahydrofuran | RT, 7 days | A |
| | | 50° C., 2 days | A |
| | toluene | RT, 7 days | A |
| | | 50° C., 2 days | A |

TABLE 15-continued

| Polymorph Screening of Compound 1 Fumarate salt | | | |
|---|---|---|---|
| Method | Solvent | Conditions[a] | XRPD Pattern[b] |
| | water | RT, 7 days | A |
| | | 50° C., 2 days | A |
| | acetone/water (95/5) | RT, 7 days | A |
| | | 50° C., 2 days | A |
| | ACN/water (95/5) | RT, 7 days | A |
| | | 50° C., 2 days | A |
| | 2-PrOH/water (95/5) | RT, 7 days | A |
| | | 50° C., 2 days | A |
| | THF/water (95/5) | RT, 7 days | A |
| | | 50° C., 2 days | A (LC) |
| heat/humidity | water vapor | RT, 59% RH | A |
| | | RT, 75% RH | A |
| | | RT, 97% RH | A |
| | | 40° C., 75% RH | A |
| | none | RT, 0% RH | A |

[a]AS = anti-solvent; E = evaporation; NC = no crystallization; RH = relative humidity; RT = room temperature
[b]NC = non-crystalline; pks = peaks; A, B, etc. = form

6.9 Preparation and Polymorphism Screening of Tosylate Salt of Compound 1

In one study, Form A of tosylate salt of Compound 1 was prepared from a precipitation experiment involving acetone and hexanes. The solids crystallized within 5 hours, and were allowed to stir at room temperature for 2 days.

In another study, the tosylate salt of Compound 1 was prepared from the free base of Compound 1 in several experiments. Initially, one small scale experiment was performed (250 mg scale, slurry in acetonitrile at room temperature for 1 day). The product was confirmed to be tosylate salt polymorph Form A. The experiment was repeated at larger scale (3.4 g scale, slurry in acetonitrile at room temperature for 3 days) and the resulting material was further characterized. Characterization data are summarized in the following table.

TABLE 16

| Characterization of Large Scale Compound 1 Tosylate Salt | |
|---|---|
| XRPD | FIG. 13 |
| XRPD Result | tosylate Form A |
| DSC/TG | FIG. 14 |
| DSC Result | endo 188.8° C. |
| TG Result | 1.0% start to 200° C. |
| NMR Result | consistent with structure |
| | 1:1 API:acid salt |

The Compound 1 tosylate salt solids were mixed with various solvents under various conditions in attempts to generate polymorphs. The results are listed in the following table. Two polymorphs were identified in this study: Form A of tosylate salt of Compound 1 (same form from Salts Screening No. 1) and a new Form D of tosylate salt of Compound 1. Form D was only obtained in one experiment as a mixture with non-crystalline material. An overlay plot of tosylate salt polymorphs Forms A, B, C, and D is shown in FIG. 22.

TABLE 17

| Polymorph Screening of Compound 1 Tosylate salt | | | |
|---|---|---|---|
| Method | Solvent | Conditions[a] | XRPD Pattern[b] |
| cooling | ACN | 80° C. → −15° C.; E | A |
| | DCM | 40° C. → −15° C.; E | A |
| | DMSO | acetone AS, 60° C.→−15° C.; E | NC |
| | | anisole AS, 60° C.→−15° C.; E | NC |
| | | EtOH AS, 60° C.→−15° C.; E | NC |
| | | EtOAc AS, 60° C.→−15° C. | NC |
| | | Ethyl formate AS, 60° C.→−15° C. | NC |
| | | Isopropyl acetate AS, 60° C.→−15° C. | NC |
| | | MTBE AS, 60° C.→−15° C. | NC |
| | | 2-PrOH AS, 60° C.→−15° C. | NC |
| | | THF AS, 60° C.→−15° C. | NC |
| | | toluene AS, 60° C.→−15° C. | NC |
| | MeOH | 65° C. → −15° C.; E | NC |
| | nitromethane | 100° C. → −15° C.; E | A |
| | water | 100° C. → −15° C.; E | A |
| | acetone/water (95/5) | 100° C. → −15° C.; E | NC |
| evaporation | ACN | open vial, RT | A + NC |
| | DCM | open vial, RT | NC + pks |
| | | | NC + pk |
| | | | NC |

TABLE 17-continued

Polymorph Screening of Compound 1 Tosylate salt

| Method | Solvent | Conditions[a] | XRPD Pattern[b] |
|---|---|---|---|
| | DMAc | open vial, RT | NC |
| | DMSO | open vial, RT | NC |
| | MeOH | open vial, RT | NC |
| | nitromethane | open vial, RT | NC |
| | NMP | open vial, RT | NC |
| | water | open vial, RT | NC + pks |
| | acetone/water (95/5) | open vial, RT | NC |
| | ACN/water (95/5) | open vial, RT | NC |
| | THF/water (95/5) | open vial, RT | NC |
| precipitation | DMAc | acetone AS, 60° C.→−15° C.; E | NC |
| | | anisole AS, 60° C.→−15° C.; E | D + NC |
| | | above sample, stressed, 80° C., 2 days | D + NC |
| | | EtOAc AS, 60° C.→−15° C.; E | NC |
| | | MTBE AS, 60° C.→−15° C. | NC |
| | | 2-PrOH AS, 60° C.→−15° C.; E | NC |
| | | toluene AS, 60° C.→−15° C.; E | NC |
| | MeOH | acetone AS, 60° C.→−15° C.; E | NC |
| | | EtOAc AS, 60° C.→−15° C.; E | A |
| | | $Et_2O$ AS, 60° C.→−15° C.; E | A (LC) |
| | | toluene AS, 60° C.→−15° C.; E | NC |
| | nitromethane | acetone AS, 60° C.→−15° C.; E | NC |
| | | $Et_2O$ AS, 60° C.→−15° C.; E | NC |
| | | 2-PrOH AS, 60° C.→−15° C.; E | NC |
| | NMP | acetone AS, 60° C.→−15° C.; E | NC |
| | | ACN AS, 60° C.→−15° C.; E | NC |
| | | EtOAc AS, 60° C.→−15° C.; E. $Et_2O$ triturate | NC + pk |
| | | MTBE AS, 60° C.→−15° C.; E. $Et_2O$ triturate | NC + pk |
| | | 2-PrOH AS, 60° C.→−15° C.; E | NC |
| | | toluene AS, 60° C.→−15° C.; E | NC |
| | water | 2-PrOH AS, 60° C.→−15° C.; E | NC + pks |
| | ACN/water (95/5) | 2-PrOH AS, 60° C.→−15° C.; E | A |
| | THF/water (95/5) | 2-PrOH AS, 60° C.→−15° C.; E | A + NC |
| slurry | acetone | RT, 7 days | A |
| | | 50° C., 2 days | A |
| | acetonitrile | RT, 7 days | A |
| | | 50° C., 2 days | A |
| | anisole | RT, 7 days | A |
| | | 50° C., 2 days | A |
| | DCM | RT, 7 days | A |
| | | 50° C., 2 days | A |
| | EtOH | RT, 7 days | A |
| | | 50° C., 2 days | A |
| | EtOAc | RT, 7 days | A |
| | | 50° C., 2 days | A |
| | ethyl formate | RT, 7 days | A |
| | | 50° C., 2 days | A |
| | isopropyl acetate | RT, 7 days | A |
| | | 50° C., 2 days | A |
| | MeOH | RT, 7 days | A |
| | | 50° C., 2 days | A |
| | MEK | RT, 7 days | A |
| | | 50° C., 2 days | A |
| | MTBE | RT, 7 days | A |
| | | 50° C., 2 days | A |
| | 2-MeTHF | RT, 7 days | A |
| | | 50° C., 2 days | A |
| | nitromethane | RT, 7 days | A |
| | | 50° C., 2 days | A |
| | 2-propanol | RT, 7 days | A |
| | | 50° C., 2 days | A |
| | tetrahydrofuran | RT, 7 days | A |
| | | 50° C., 2 days | A |
| | toluene | RT, 7 days | A |
| | | 50° C., 2 days | A |
| | water | RT, 7 days | A |
| | | 50° C., 2 days | A |
| | acetone/water (95/5) | RT, 7 days | A |
| | | 50° C., 2 days | A |
| | 2-PrOH/water (95/5) | RT, 7 days | NC + pks |
| | | 50° C., 2 days | A |

TABLE 17-continued

| Polymorph Screening of Compound 1 Tosylate salt | | | |
|---|---|---|---|
| Method | Solvent | Conditions[a] | XRPD Pattern[b] |
| heat/humidity | water vapor | RT, 59% RH | A |
| | | RT, 75% RH | A |
| | | RT, 97% RH | A |
| | | 40° C., 75% RH | A |
| | none | RT, 0% RH | A |

[a]AS = anti-solvent; NC = no crystallization; RH = relative humidity; RT = room temperature; E = evaporation
[b]NC = non-crystalline; pks = peaks; A, B, etc. = form

6.10 Evaluation of Forms (a) Evaluation of Form a of a Hydrochloride Salt of Compound 1

Hygroscopicity: Form A of a hydrochloride salt of Compound 1 was characterized by DVS (FIG. 7). It picked up water starting at very low humidities. Water sorption continued to occur at all humidities steadily (almost linearly) in uptake of about 3.0% w/w corresponding to about 1 mole of water. The adsorbed water was released in the desorption phase with slight hysteresis observed in the drying phase. The solid form remained as Form A after DVS.

Shear Sensitivity: Form A of a hydrochloride salt of Compound 1 was compressed under 700 and 1100 lbs for 1 minute and analyzed by XRPD. The solid form remained the same, with slightly broader diffraction peaks.

Solid State Stability: Solid state stability of Form A of a hydrochloride salt of Compound 1 was evaluated using Accelerated Stability Assessment Program (ASAP). Forced degradation storage conditions were used between 60-80° C. and 0-80% RH for up to 2 weeks. A photostress study under 2 times ICH conditions was also conducted in the solid state. The solid samples were analyzed for both chemical and chiral stability. At the end of the study, the crystalline form of the compound was verified by XRPD. No change of crystalline form was observed under the most stringent condition 80° C./70% RH after 10 days vs control. The results of the stability studies are summarized in the following table.

TABLE 18

| Solid State Stability of Form A of hydrochloride salt of Compound 1 at Different Storage Conditions | | | | | |
|---|---|---|---|---|---|
| Sample name | Timepoint (Days) | Temp (° C.) | RH (%) | LC Purity (%) | R-isomer % area |
| Heat/Humidity Control | NA | NA | NA | 98.44 | 1.26 |
| 60° C., 50% RH, 7 days | 7 | 60.01 | 49.01 | 98.51 | 1.26 |
| 60° C., 50% RH, 14 days | 14 | 60.01 | 49.01 | 98.47 | 1.28 |
| 70° C., 20% RH, 7 days | 7 | 70.17 | 19.08 | 98.28 | 1.26 |
| 70° C., 20% RH, 14 days | 14 | 70.17 | 19.08 | 98.50 | 1.26 |
| 70° C., 75% RH, 7 days | 7 | 70.09 | 75.67 | 98.48 | 1.34 |
| 70° C., 75% RH, 14 days | 14 | 70.09 | 75.67 | 98.24 | 1.49 |
| 80° C., 0% RH, 7 days | 7 | 80.19 | 0.15 | 91.18 | 1.27 |
| 80° C., 0% RH, 14 days | 14 | 80.19 | 0.15 | 86.98 | 1.28 |
| 80° C., 40% RH, 7 days | 7 | 79.84 | 41.16 | 98.32 | 1.27 |

TABLE 18-continued

| Solid State Stability of Form A of hydrochloride salt of Compound 1 at Different Storage Conditions | | | | | |
|---|---|---|---|---|---|
| Sample name | Timepoint (Days) | Temp (° C.) | RH (%) | LC Purity (%) | R-isomer % area |
| 80° C., 40% RH, 14 days | 14 | 79.84 | 41.16 | 98.29 | 1.30 |
| 80° C., 70% RH, 7 days | 7 | 79.56 | 69.13 | 98.43 | 1.36 |
| 80° C., 70% RH, 14 days | 14 | 79.56 | 69.13 | 98.21 | 1.45 |
| Photo Stressed Control | NA | NA | NA | 98.45 | 1.27 |
| 2 × ICH Photo Stressed | NA | NA | NA | 94.80 | 1.17 |

No significant changes (<5%) in assay were observed, except for the 80° C./0% RH condition after 1 week and 2 weeks. The loss of assay at 80° C./0% RH was attributed to the growth of a degradation product with a molecular weight corresponding to the free base+HCl. Compound 1 hydrochloride salt remained stable with respect to assay and degradation products under the other conditions. Changes in assay under photostability conditions were <4%. Additionally, no significant change was observed in chiral purity across all conditions, with a maximum change of 0.2% under high humidity conditions. These ASAP stability results confirmed that Form A of a hydrochloride salt of Compound 1 can be considered stable.

Crystal Habit: The SEM image of Form A of a hydrochloride salt of Compound 1 shows small rod primary particles as well as agglomerates (FIG. 8).

Long Term Solid State Stability: Form A of a hydrochloride salt of Compound 1 (packaged in double LDPE bags in HDPE container) was stored up to 3 months at 25° C./60% RH, 30° C./65% RH, and 40° C./75% RH storage conditions. The stability data listed in the table below demonstrate stability of Form A of a hydrochloride salt of Compound 1 stored at 25° C./60% RH, 30° C./65% RH and 40° C./75% RH conditions for 3 months. Therefore, a re-test period of 12 months is proposed when stored at or below 25° C.

TABLE 19

| Stability Results for Form A of a hydrochloride salt of Compound 1 in double LDPE bags in HDPE Container | | | |
|---|---|---|---|
| 25° C./60% RH | 0 Month | 1 Month | 3 Month |
| Appearance[1] | Conforms | Conforms | Conforms |
| Solid forms (XRPD)[2] | Conforms | Conforms | Conforms |
| Chromatographic Purity (%) | 98.6 | 98.5 | 98.5 |
| Chiral Purity (%) | 96.0 | 95.7 | 95.7 |

TABLE 19-continued

| Stability Results for Form A of a hydrochloride salt of Compound 1 in double LDPE bags in HDPE Container | | | |
|---|---|---|---|
| Water (%) | 1.4 | 1.7 | 1.9 |
| Total Related Impurities (%) | 1.41 | 1.50 | 1.55 |
| 30° C./65% RH | 0 Month | 1 Month | 3 Month |
| Appearance[1] | Conforms | Conforms | Conforms |
| Solid forms (XRPD)[2] | NT | NT | NT |
| Chromatographic Purity (%) | 98.6 | 98.4 | 98.4 |
| Chiral Purity (%) | 96.0 | 94.5 | 95.8 |
| Water (%) | 1.4 | 1.9 | 2.0 |
| Total Related Impurities (%) | 1.41 | 1.56 | 1.63 |
| 40° C./75% RH | 0 Month | 1 Month | 3 Month |
| Appearance[1] | Conforms | Conforms | Conforms |
| Solid forms (XRPD)[2] | Conforms | Conforms | Conforms |
| Chromatographic Purity (%) | 98.6 | 98.5 | 98.4 |
| Chiral Purity (%) | 96.0 | 96.0 | 96.1 |
| Water (%) | 1.4 | 1.8 | 2.0 |
| Total Related Impurities (%) | 1.41 | 1.52 | 1.60 |

[1]Yellow powder
[2]Consistent with Form A (b) Evaluation of Other Forms of Compound 1

Solid state stability of Compound 1 free base amorphous, tosylate Form A, besylate Form A, and fumarate Form A (as well as HCl Form A) was evaluated under stress storage conditions. The solid samples were analyzed for both chemical and chiral stability. At the end of the study, the crystalline form of Compound 1 was verified by XRPD. The results of the stability studies are summarized in the following table.

TABLE 20

Solid state stability of free base and salt forms

| | Free base | | | Besylate | | |
|---|---|---|---|---|---|---|
| Condition | Physical | Chemical (%) | Chiral (%) | Physical | Chemical (%) | Chiral (%) |
| Ambient | | 98.95 | 99.16 | Stable | 98.64 | 98.70 |
| 40° C. | | 98.44 | 99.03 | Stable | 98.56 | 98.71 |
| 40° C./80% RH | | 98.56 | 99.02 | Unstable | 97.69 | 98.66 |
| 60° C. | Unstable | 95.80 | 98.69 | Stable | 98.58 | 98.62 |
| 60° C./75% RH | Unstable | 98.10 | 83.04 | Unstable | 96.77 | 96.36 |
| 70° C. | Unstable | 85.68 | 95.57 | Stable | 97.76 | 98.64 |
| 70° C./80% RH | Unstable | 93.29 | 52.01 | Unstable | 96.93 | 95.11 |

| | Tosylate | | | Fumarate | | |
|---|---|---|---|---|---|---|
| Condition | Physical | Chemical (%) | Chiral (%) | Physical | Chemical (%) | Chiral (%) |
| Ambient | | 99.19 | 98.49 | | 98.77 | 95.82 |
| 40° C. | Stable | 99.18 | 98.52 | Stable | 98.64 | 95.39 |
| 40° C./80% RH | Stable | 98.84 | 98.48 | Stable | 98.69 | 94.55 |
| 60° C. | Stable | 99.01 | 98.46 | Stable | 97.43 | 95.54 |
| 60° C./75% RH | Stable | 96.76 | 98.10 | Stable | 98.19 | 93.14 |
| 70° C. | Stable | 98.58 | 98.43 | Stable | 95.94 | 95.11 |
| 70° C./80% RH | Stable | 95.73 | 97.64 | Stable | 93.79 | 91.52 |

| | HCl salt | | |
|---|---|---|---|
| Condition | Physical | Chemical (%) | Chiral (%) |
| Ambient | | 99.08 | 99.26 |
| 40° C. | Stable | 99.13 | 99.29 |
| 40° C./80% RH | Stable | 99.56 | 99.22 |
| 60° C. | Stable | 99.35 | 99.02 |
| 60° C./75% RH | Stable | 99.56 | 98.70 |
| 70° C. | Stable | 99.32 | 99.13 |
| 70° C./80% RH | Stable | 99.43 | 98.91 |

Solubility of Compound 1 free base amorphous, HCl Form A, fumarate Form A, and tosylate Form A in several solvents were estimated. The experiments were carried out by adding the test solvent in aliquots to weighed portions of solid. Whether dissolution had occurred was judged by visual inspection after addition of each solvent aliquot. Solubility numbers were calculated by dividing the total amount of solvent used to dissolve the sample by the weight of the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than or equal to" if dissolution occurred on addition of the first solvent aliquot. The results are listed in the following table.

TABLE 21

Estimated solubility of free base and salt forms

| Solvent | Free Base Solubility (mg/mL) | HCl Salt Solubility (mg/mL) | Fumarate Solubility (mg/mL) | Tosylate Solubility (mg/mL) |
|---|---|---|---|---|
| acetone | 52 | <1 | <1 | <1 |
| acetonitrile | 33 | <1 | <1 | 1 |
| anisole | 26 | <1 | <1 | <1 |
| dichloromethane | 59 | <1 | <1 | 1 |
| dimethylacetamide | 34 | 1 | 23 | 30 |
| dimethylsulfoxide | N/T | 38 | 36 | 34 |
| ethanol | 1 | <1 | <1 | <1 |
| ethyl acetate | 33 | <1 | <1 | <1 |
| ethyl formate | 30 | <1 | <1 | <1 |
| isopropyl acetate | 6 | <1 | <1 | <1 |
| methanol | 2 | 2 | 3 | 3 |
| methyl ethyl ketone | 29 | <1 | <1 | <1 |
| methyl tert-butyl ether | <1 | <1 | <1 | <1 |
| 2-methyl tetrahydrofuran | 30 | <1 | <1 | <1 |
| nitromethane | 34 | <1 | <1 | 4 |
| N-methyl pyrrolidone | 31 | 1 | 17 | 17 |
| 2-propanol | <1 | <1 | <1 | <1 |
| tetrahydrofuran | 28 | <1 | 1 | <1 |
| toluene | 3 | <1 | <1 | <1 |
| water | <1 | 2 | 2 | 2 |
| 95:5 acetone/water | 31 | <1 | 2 | 3 |
| 95:5 ACN/water | 27 | 3 | 2 | 17 |
| 95:5 2-PrOH/water | 2 | <1 | 1 | <1 |
| 95:5 THF/water | 20 | 1 | 8 | 16 |

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A process for preparing a solid form of a hydrochloride salt of Compound 1:

1

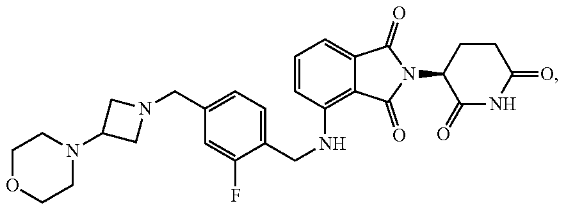

which is characterized by an XRPD pattern comprising peaks at 15.1, 16.3, and 20.7° 2θ±0.2° 2θ, and the process comprise slurrying Compound 1 free base and within 10% of 1 equivalent of hydrochloric acid in a solvent, wherein the solvent is acetone, acetonitrile, anisole, DCM, DMAc, EtOH, EtOAc, ethyl formate, isopropyl acetate, MeOH, MEK, MTBE, 2-MeTHF, nitromethane, NMP, 2-propanol, tetrahydrofuran, toluene, water, a mixture of acetone and water, a mixture of acetonitrile and water, a mixture of 2-PrOH and water, or a mixture of THF and water.

2. The process of claim 1, wherein the solvent is acetonitrile.

3. The process of claim 1, wherein the solvent is EtOAc.

4. The process of claim 1, wherein the solvent is a 95/5 v/v mixture of acetone and water.

5. The process of claim 1, wherein the slurrying is conducted at room temperature.

6. The process of claim 1, wherein the slurrying is conducted at 50° C.

7. The process of claim 1, wherein the slurrying is conducted for a time period of from 1 day to 7 days.

8. The process of claim 7, wherein the slurrying is conducted for 2 days.

9. The process of claim 7, wherein the slurrying is conducted for 7 days.

10. The process of claim 1, wherein the solvent is a 95/5 v/v mixture of acetonitrile and water.

11. The process of claim 1, wherein the solvent is a 95/5 v/v mixture of 2-PrOH and water, or a 95/5 v/v mixture of THF and water.

12. The process of claim 1, wherein the solvent is a 95/5 v/v mixture of THF and water.

13. The process of claim 1, wherein the solvent is acetone.

14. The process of claim 1, wherein the solvent is tetrahydrofuran.

* * * * *